US007122525B2

(12) United States Patent
Michaelis et al.

(10) Patent No.: US 7,122,525 B2
(45) Date of Patent: Oct. 17, 2006

(54) TARGETED THERAPEUTICS AND USES THEREOF

(75) Inventors: Arthur F. Michaelis, Devon, PA (US); Hawkins V. Maulding, Mendham, NJ (US); Chalom Sayada, Luxembourg (LU); Congxiang Zha, Schenectady, NY (US)

(73) Assignee: ActivBiotics, Inc., Lexington, MA (US)

( * ) Notice: Subject to any disclaimer, the term of this patent is extended or adjusted under 35 U.S.C. 154(b) by 287 days.

(21) Appl. No.: 10/302,409

(22) Filed: Nov. 21, 2002

(65) Prior Publication Data

US 2004/0063718 A1 Apr. 1, 2004

Related U.S. Application Data

(60) Provisional application No. 60/358,881, filed on Feb. 22, 2002, provisional application No. 60/332,264, filed on Nov. 21, 2001.

(51) Int. Cl.
*A61K 31/70* (2006.01)
*A61K 31/665* (2006.01)
*C07D 267/22* (2006.01)
*C07H 17/08* (2006.01)

(52) U.S. Cl. .................. 514/29; 514/100; 536/7.4; 540/458; 540/459

(58) Field of Classification Search ............... 536/7.4; 514/29, 100; 540/458, 459
See application file for complete search history.

(56) References Cited

U.S. PATENT DOCUMENTS

| | | | |
|---|---|---|---|
| 3,108,099 A | 10/1963 | Felder et al. | |
| 3,301,753 A | 1/1967 | Sensi et al. | |
| 3,338,888 A | 8/1967 | Bickel et al. | |
| 3,342,810 A | 9/1967 | Maggi et al. | |
| 3,884,673 A | 5/1975 | Olin | |
| 4,005,077 A | 1/1977 | Bickel et al. | |
| 4,017,481 A | 4/1977 | Marsili et al. | |
| 4,086,225 A | 4/1978 | Marsili et al. | |
| 4,164,499 A | 8/1979 | Rossetti et al. | |
| 4,165,317 A | 8/1979 | Rossetti et al. | |
| 4,188,321 A | 2/1980 | Maggi et al. | |
| 4,219,478 A | 8/1980 | Marsili et al. | |
| 4,226,765 A | 10/1980 | Marsili et al. | |
| 4,305,941 A | 12/1981 | Marsili et al. | |
| 4,341,785 A | 7/1982 | Marchi et al. | |
| 4,551,450 A | 11/1985 | Traxler | |
| 4,585,589 A | 4/1986 | Malabarba et al. | |
| 4,681,938 A | 7/1987 | Traxler | |
| 4,690,919 A | 9/1987 | Yamane et al. | |
| 4,859,661 A | 8/1989 | Kano et al. | |
| 4,876,258 A | 10/1989 | Kump et al. | |
| 4,962,111 A | 10/1990 | Welch et al. | |
| 4,965,261 A | 10/1990 | Kanoo et al. | |
| 4,983,602 A | 1/1991 | Yamane et al. | |
| 5,003,070 A | 3/1991 | Kump et al. | |
| 5,352,679 A | 10/1994 | Ferrieri et al. | |
| 5,547,683 A | 8/1996 | Yano et al. | |
| 5,643,912 A | 7/1997 | Cynamon et al. | |
| 5,786,349 A | 7/1998 | Yamashita et al. | |
| 5,786,350 A | 7/1998 | Occelli et al. | |
| 5,981,522 A | 11/1999 | Yamashita et al. | |
| 6,316,433 B1 | 11/2001 | Rose et al. | |
| 6,399,607 B1 | 6/2002 | Welch et al. | |
| 6,486,161 B1 | 11/2002 | Fujii et al. | |

*Primary Examiner*—Elli Peselev
(74) *Attorney, Agent, or Firm*—Clark & Elbing LLP

(57) ABSTRACT

The invention features a method of delivering a drug to a diseased cell by linking the drug to a rifamycin derivative, compositions that include drug-rifamycin conjugates of the invention, and methods for treating disease using those compositions.

19 Claims, 6 Drawing Sheets

Pyrazinoic Acid

Glycolic Acid

Rifamycin Derviative

Fig. 2 (1 of 2)
| drug (B) | structure |
|---|---|
| isoniazid | 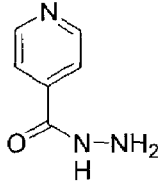 |
| ethambutol | 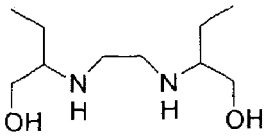 |
| azithromycin | 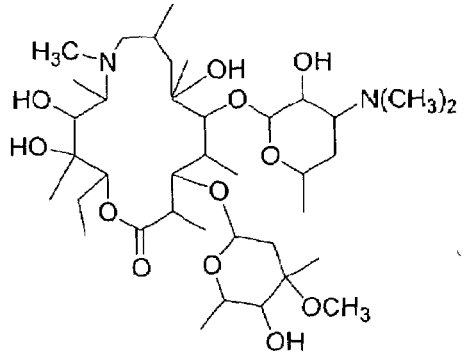 |
| p-aminosalicylic acid | 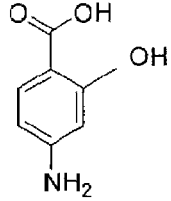 |
| ethionamide | 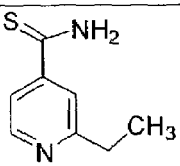 |
| pyrazinamide | 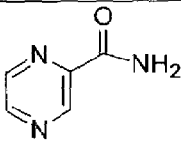 |
| cycloserine | 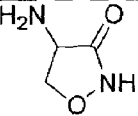 |

Fig. 2 (2 of 2)
| 4-pyridinemethanol | 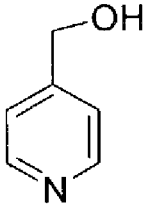 |
|---|---|
| 2-ethyl-4-pyridinemethanol | 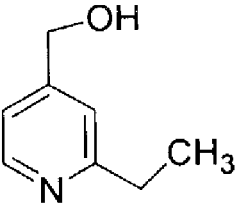 |
| isonicotinic acid | 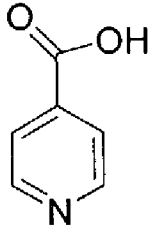 |
| 2-ethylisonicotinic acid | 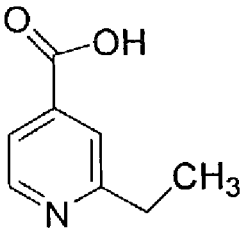 |

Fig. 3 (1 of 3)

| Formula Number | Structure |
|---|---|
| XX-a | 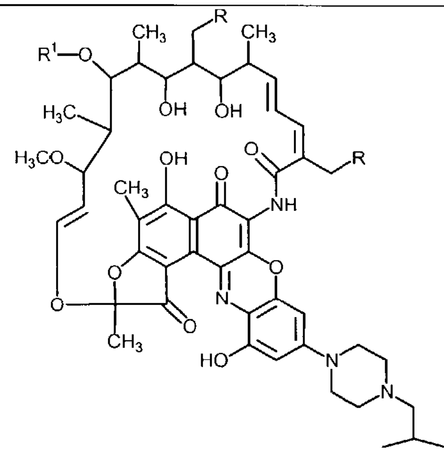 |
| XX-b | 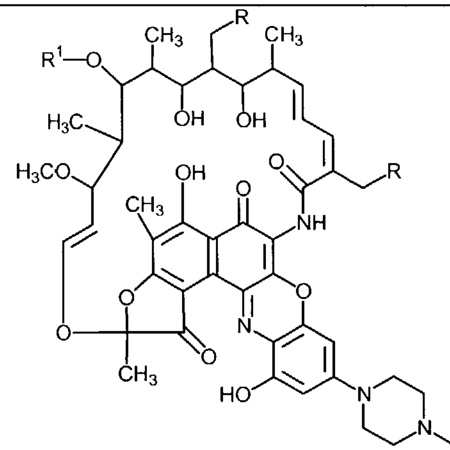 |
| XX-c | 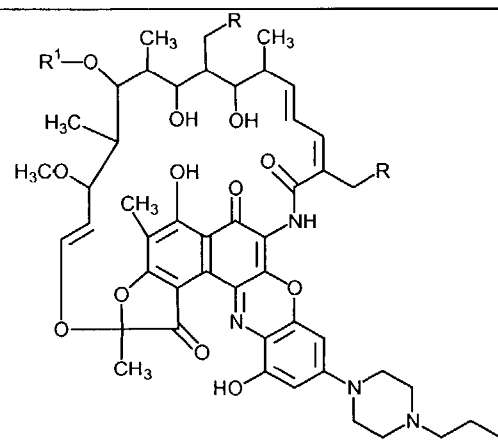 |

Fig. 3 (2 of 3)
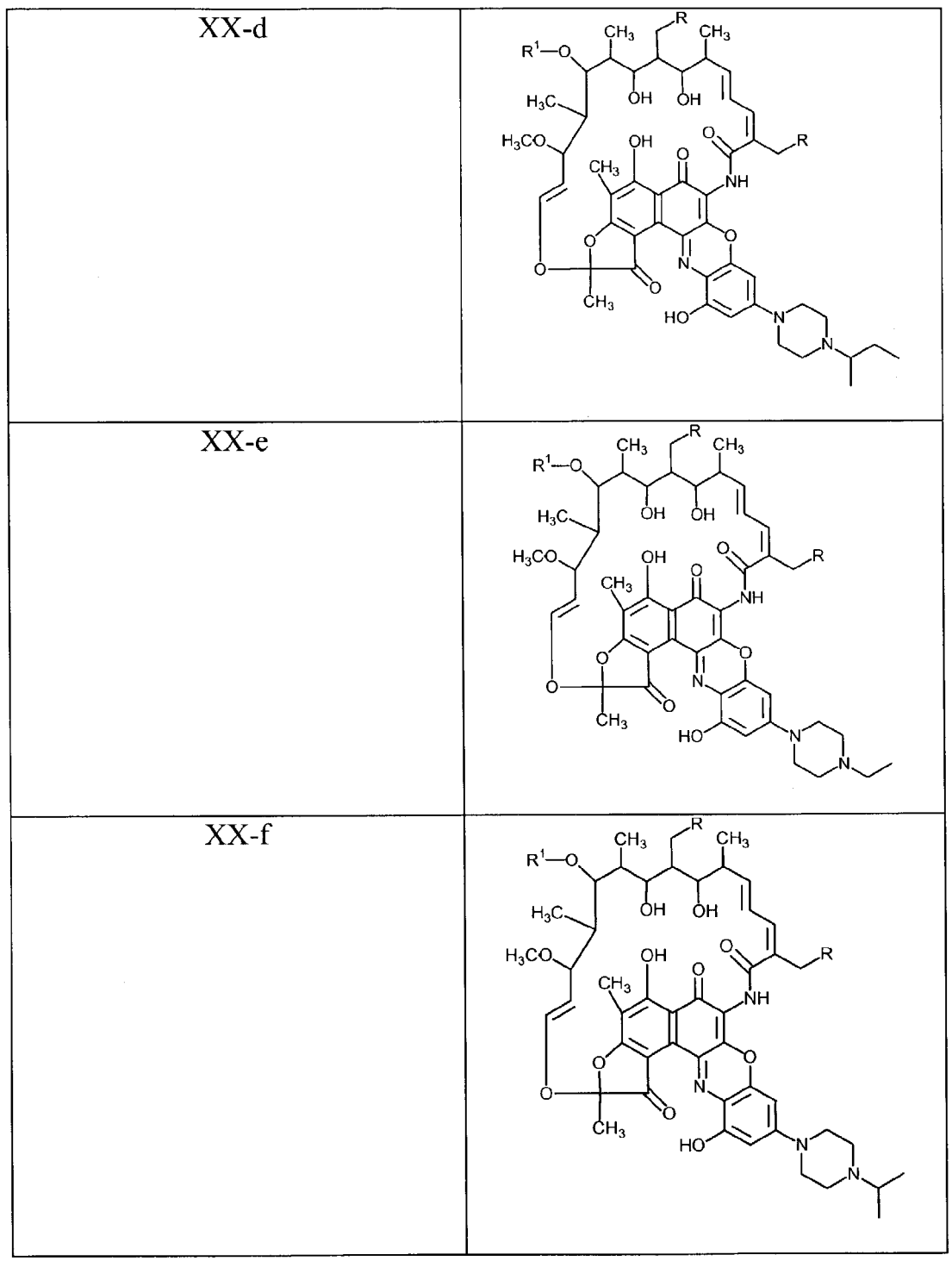

Fig. 3 (3 of 3)
| III-a | 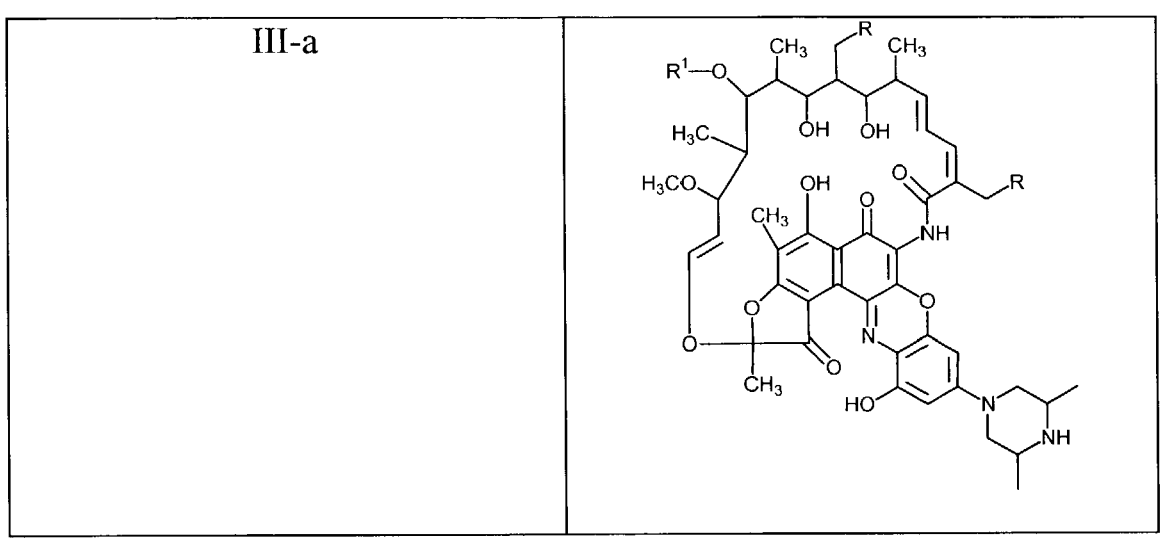 |

TARGETED THERAPEUTICS AND USES THEREOF

CROSS-REFERENCE TO RELATED APPLICATIONS

The application claims benefit of U.S. Provisional Application Nos. 60/332,264, filed Nov. 21, 2001, and 60/358,881, filed Feb. 22, 2002, each of which is hereby incorporated by reference.

BACKGROUND OF THE INVENTION

The present invention relates to the field of targeted drug delivery.

The efficacy of a drug may be improved by altering its biodistribution such that the drug is localized at the site of disease. The advantages include, for example, improved activity in the treatment or prevention of disease and, in some instances, reduced toxicity.

One general approach to altering biodistribution involves changing the formulation of a drug. For example, in a nanoparticulate formulation (e.g., liposome, biodegradable polymer, or solid lipid nanoparticle), a drug is directed to organs and tissues of the RES system (e.g., liver, spleen, lung, vascular macrophage). Alternatively, a drug's biodistribution can be altered by covalently linking it to a targeting moiety, e.g., a ligand for an endogenous receptor or a molecule that facilitates transport into cells and/or tissues. Examples of ligands for endogenous receptors include biotin, antibodies, and receptor-targeted peptides (e.g., RGD peptides and somatostatin). Examples of targeting moieties that can facilitate transport include small proteins and peptides that permeate plasma membranes (e.g., HIV-1 tat peptide). The biodistribution of the drug incorporated into a targeting moiety-drug conjugate is altered under the influence of the targeting moiety.

The literature describing the bioconjugate techniques involved in the preparation of targeting moiety-drug conjugates is extensive. In some instances, the conjugates are linked by biodegradable linkers, either to aid in the elimination of the drug or to improve the activity of the drug, once it has been delivered to the desired tissue.

Many diseases exist for which there are few effective treatments. For example, the number of drug resistant pathogens is continually increasing. Thus, improved methods are needed for the treatment and prevention of disease. Some of these new methods, as discussed above, focus on mechanisms of delivering drugs to diseased tissues. These include methods which modulate the biodistribution or membrane transport of drugs. Desirably, these new treatments enhance the efficacy of the drug without introducing adverse side-effects.

SUMMARY OF THE INVENTION

We have discovered that rifamycin derivatives can serve as targeting moieties for other therapeutic compounds. This discovery is based on our observation that the antimicrobial potency of rifamycin derivatives is related to both their effect at the site of action and to their biodistribution pattern, which locates the drug at sites of infection. It is possible to impart the advantageous biodistribution found among rifamycin derivatives to other drugs, in order to provide optimal activity for these latter drugs. Attaching a rifamycin derivative (A) to a therapeutic drug (B) via a linker (L) results in improved localization at the site of delivery for the therapeutic drug. In one example, (A) and (B) may be attached through a cleavable linker. In this case, cleavage of the linker at the site of delivery liberates the therapeutic drug from the linker. This results in an increase in the local concentration of the drug (B), enhancing its therapeutic effect. Thus, the invention features a method of increasing delivery of a drug to a diseased cell by linking the drug to a rifamycin derivative.

Accordingly, in a first aspect, the present invention features a rifamycin derivative (A) covalently tethered via a linker (L) to a therapeutic drug (B), as depicted in formula I:

wherein (A) is a rifamycin derivative of formula II:

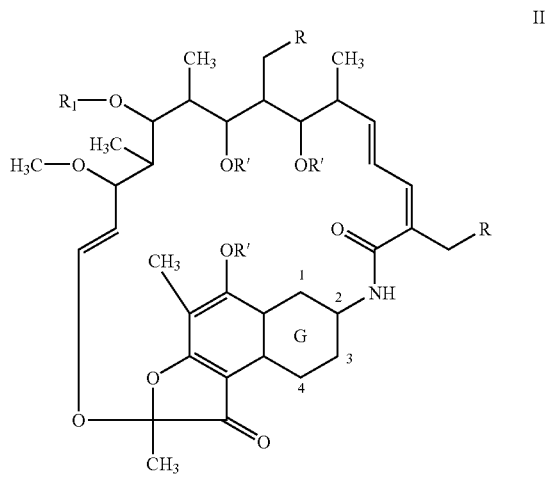

In formula II, each methine proton, methylene proton, and methyl proton is optionally substituted by —OH or —OR*, R represents a hydrogen atom, a hydroxyl group, or —OR*, $R_1$ represents a hydrogen atom, an acetyl group, or R*, and ring G is selected from formulas III–XI:

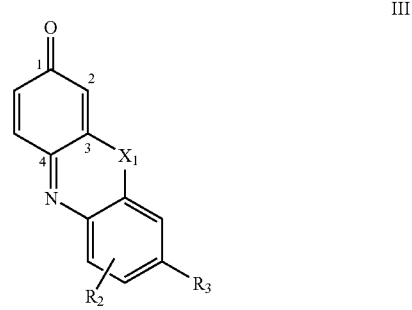

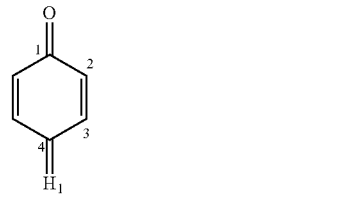

-continued

V
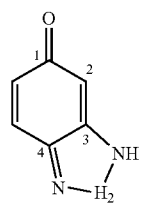

VI
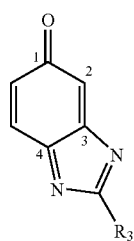

VII
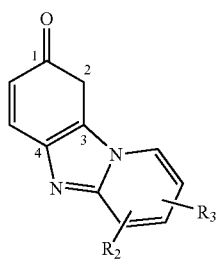

VIII
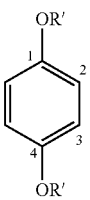

IX
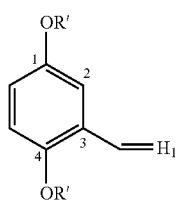

X
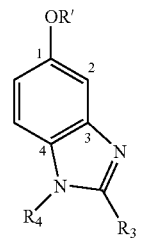

XI
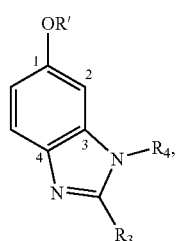

In the formulas above, R' represents a hydrogen atom or R*, $X_1$ represents an oxygen atom or a sulfur atom, $H_1$ represents an oxygen atom, N—$R_3$ or R*, and $H_2$ represents a group expressed by formulas XII or XIII:

XII
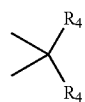

XIII
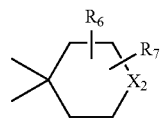

$R_2$ represents a hydroxyl group, a sulfhydryl group, a hydrogen atom, or an alkyl group having 1 to 3 carbon atoms. $R_3$ represents a hydrogen atom, an alkyl group having 1 to 10 carbon atoms, or a group expressed by one of formulas XIV–XVI:

XIV
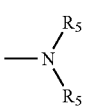

XV
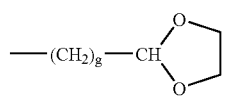

XVI
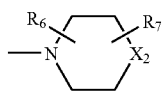

Each $R_4$ is, independently, a hydrogen atom or an alkyl group having 1 to 7 carbon atoms. Each $R_5$ is, independently, an allyl group having 1 to 7 carbon atoms, or two of $R_5$ in combination form a 3–8 membered cyclic system. In formula XV, g represents an integer between 1 and 3. $R_6$ and $R_7$ are each, independently, a hydrogen atom or an alkyl group having 1 to 3 carbon atoms. $X_2$ represents an oxygen atom, a sulfur atom, a carbonyl group, or a group expressed by one of formulas XVII–XIX:

XVII
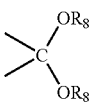

XVIII
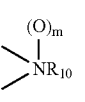

XIX
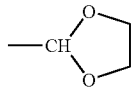

$R_8$ and $R_9$ are each, independently, a hydrogen atom, or an alkyl group having 1 to 3 carbon atoms, or $R_8$ and $R_9$, in combination with each other, represent —$(CH_2)_k$—, in which k represents an integer between 1 and 4. In formula XVIII, m represents 0 or 1. $R_{10}$ represents a hydrogen atom, an alkyl group having 1 to 6 carbon atoms, or —$(CH_2)_nX_3$, in which n represents an integer between 1 and 4. $X_3$ represents an alkoxy group having 1 to 3 carbon atoms, a vinyl group, or an ethynyl group. In all of the formulas above, R* is a bond in a linkage group between (A) and (L). (L) is a linker which forms linkage groups with rifamycin derivative (A) and therapeutic drug (B).

In particular embodiments, (B) is selected from the group consisting of isoniazid, ethambutol, azithromycin, pyrazinamide, p-aminosalicylic acid, ethionamide, cycloserine, 4-pyridinemethanol, 2-ethyl-4-pyridinemethanol, isonicotinic acid, and 2-ethyl-isonicotinic acid.

In some desirable embodiments, rifamycin derivative (A) is a compound described by formula XX:

XX

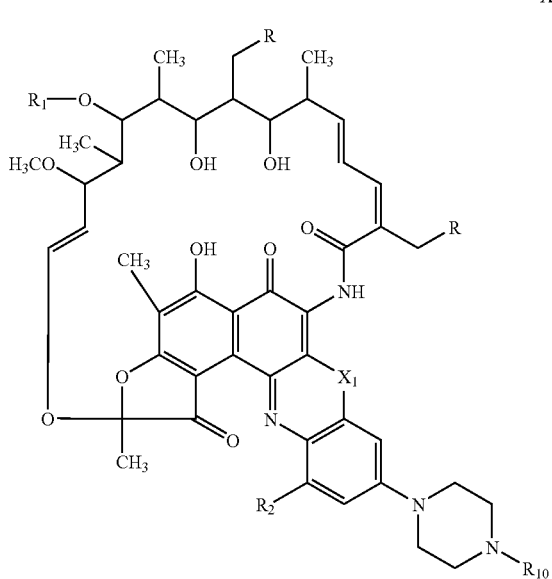

wherein R represents a hydrogen atom, a hydroxyl group or —OR*. $X_1$ represents an oxygen atom or a sulfur atom. $R_1$ represents a hydrogen atom, an acetyl group, or R*. $R_2$ represents a hydroxyl group, a sulfhydryl group, a hydrogen atom, or an alkyl group having 1 to 3 carbon atoms. $R_{10}$ represents a hydrogen atom, an alkyl group having 1 to 6 carbon atoms, or —$(CH_2)_nX_3$, in which n represents an integer between 1 and 4. $X_3$ represents an alkoxy group having 1 to 3 carbon atoms, a vinyl group, or an ethynyl group. R* is a bond in a linkage group formed with (L).

In still further embodiments, (A) is a compound described by formula XX wherein $X_1$ represents an oxygen atom; $R_2$ represents a hydroxyl group or a sulfhydryl group; $R_{10}$ is selected from the group consisting of methyl, ethyl, isopropyl, n-propyl, iso-butyl, (S)-sec-butyl, and (R)-sec-butyl; and R* is a bond in a linkage group formed with (L).

In various embodiments, linker (L) is described by formula XXI:

XXI

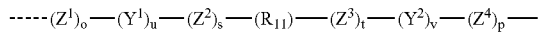

where each of $Z^1$, $Z^2$, $Z^3$, and $Z^4$ is independently selected from O, S, and $NR_{12}$ (where $R_{12}$ is hydrogen or an alkyl group); each of $Y^1$ and $Y^2$ is independently selected from carbonyl, thiocarbonyl, sulphonyl, phosphoryl, or similar acid-forming group; o, p, s, t, u, and v are each independently 0 or 1; and $R_{11}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_qCH_2CH_2$— in which q is 1 to 4, or a chemical bond linking —$(Z^1)_o$—$(Y^1)_u$—$(Z^2)_s$— to —$(Z^3)_t$—$(Y^2)_v$—$(Z^4)_p$—.

In further embodiments, linker (L) is described by any of formulas XXII–XXIV:

XXII

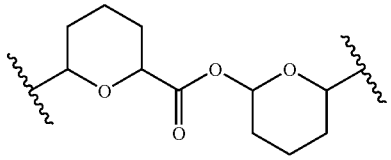

XXIII

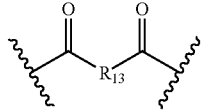

XXIV

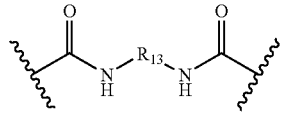

wherein the linker is covalently attached to both an oxygen atom of drug (B) and an oxygen atom of (A). Accordingly, linker (L) of formulas XXII–XXIV are attached to a rifamycin derivative (A) and drug (B) via dipyran, ester, or carbamate linkage groups. In these embodiments, $R_{13}$ represents a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_nCH_2CH_2$— in which n is 1 to 4, or a chemical bond linking two nitrogens or two carbonyls.

In further embodiments, (L) has the chemical formula XXV:

XXV

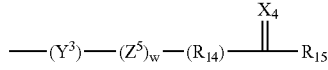

wherein $Z^5$ is selected from O, S, or $NR_{16}$; $R_{16}$ is hydrogen or an alkyl group; $R_{15}$ is selected from hydrogen, an alkyl, or a heteroalkyl; $Y^3$ is selected from a carbonyl, thiocarbonyl, sulphonyl, phosphoryl, or a similar acid-forming group covalently bound to an oxygen atom of rifamycin derivative (A); w is 0 or 1; $R_{14}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_nCH_2CH_2$—, in which n is 1 to 4, or a chemical bond linking —$(Y^3)$—$(Z^5)_w$— to

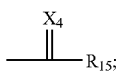

and $X_4$ is a hydrazone resulting from the condensation reaction of a drug B containing a hydrazide group and the precursor to linker XXV, in which $X_4$ is the oxygen atom of a ketone or aldehyde group.
In another aspect, the invention features compounds of formulas XXVI–XXXV:
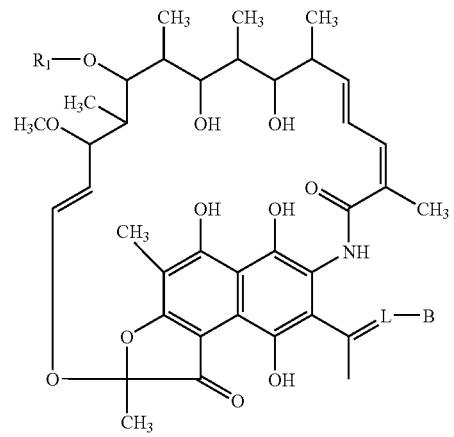
XXVI
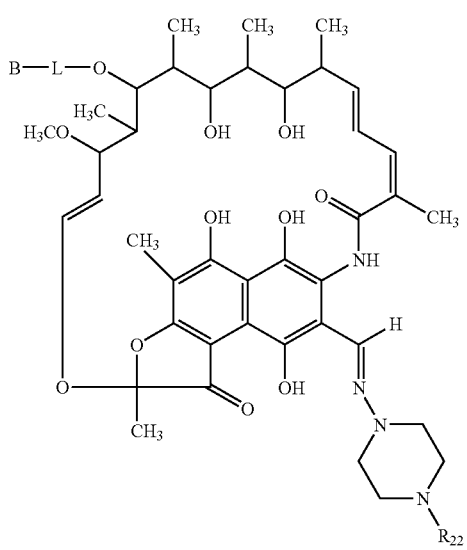
XXVII
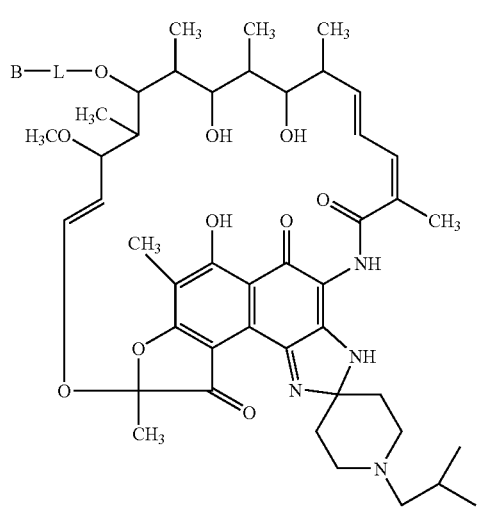
XXVIII
-continued
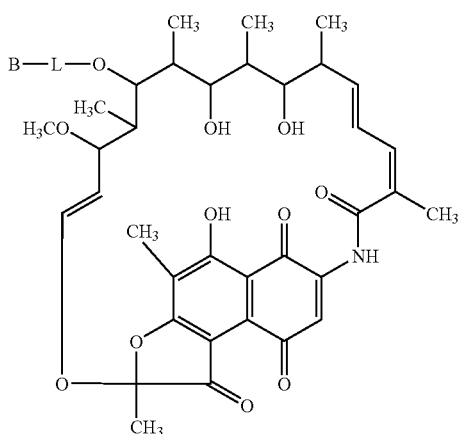
XXIX
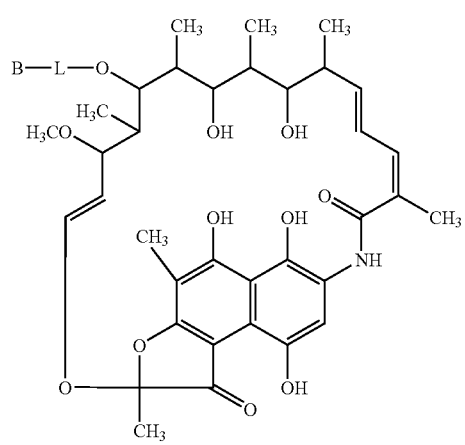
XXX
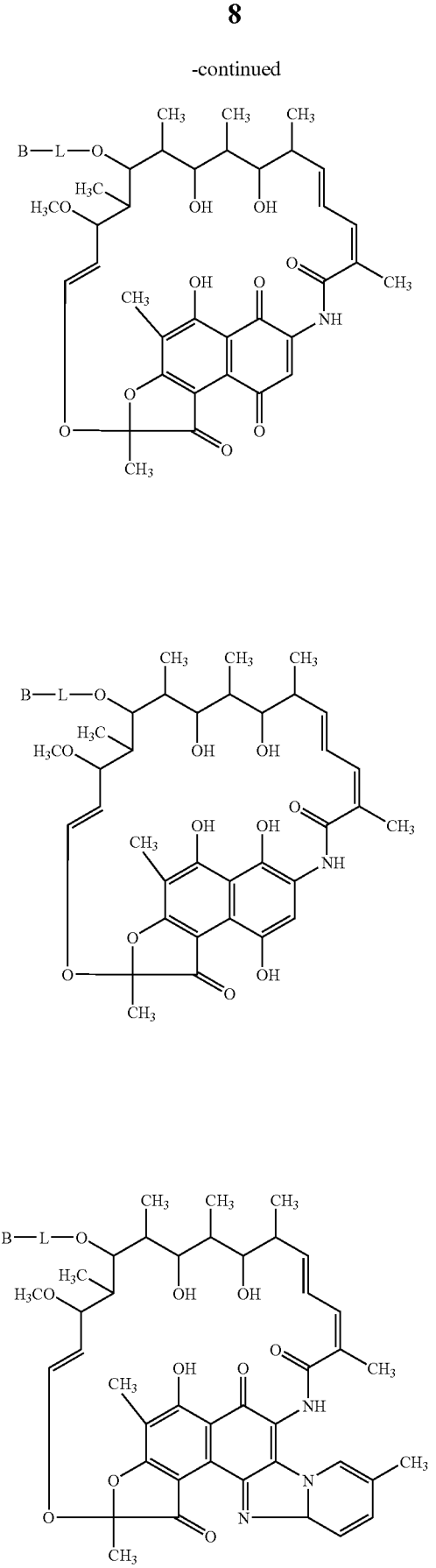
XXXI -continued
XXXII
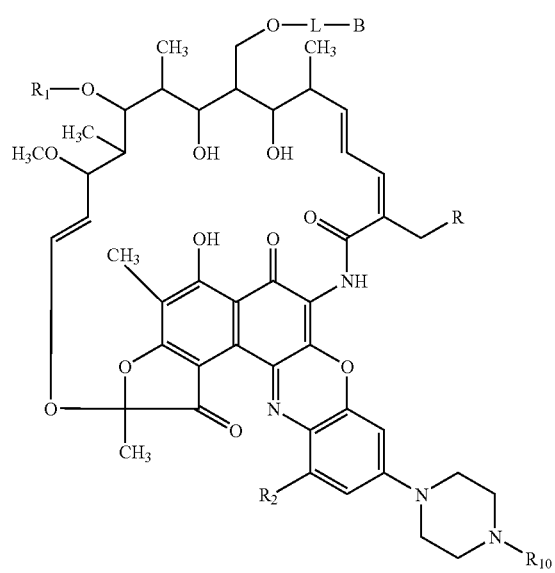
XXXIII
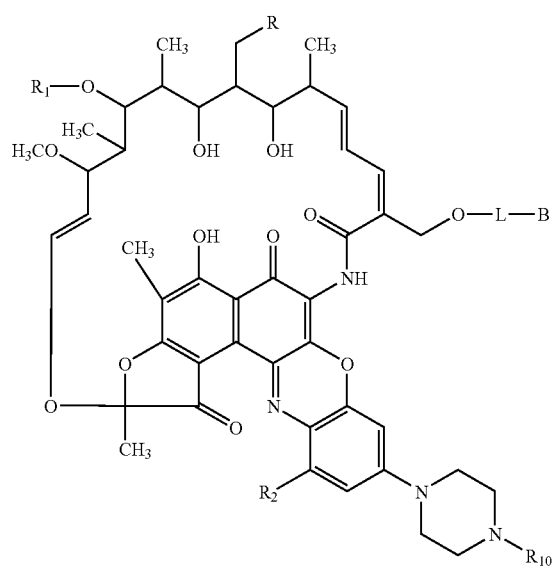
XXXIV
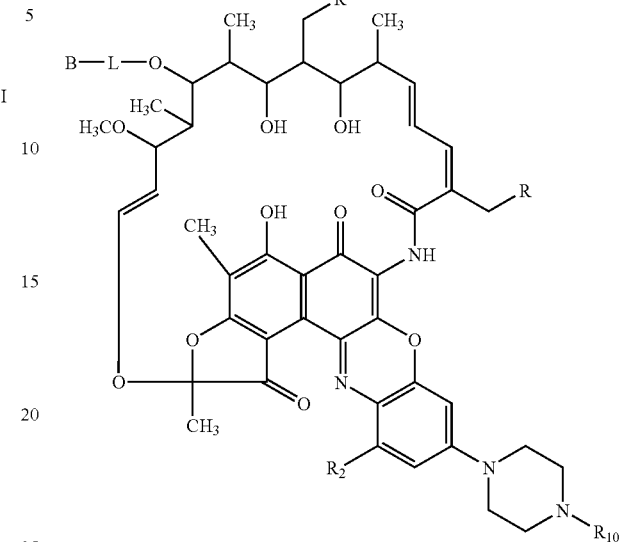
XXXV
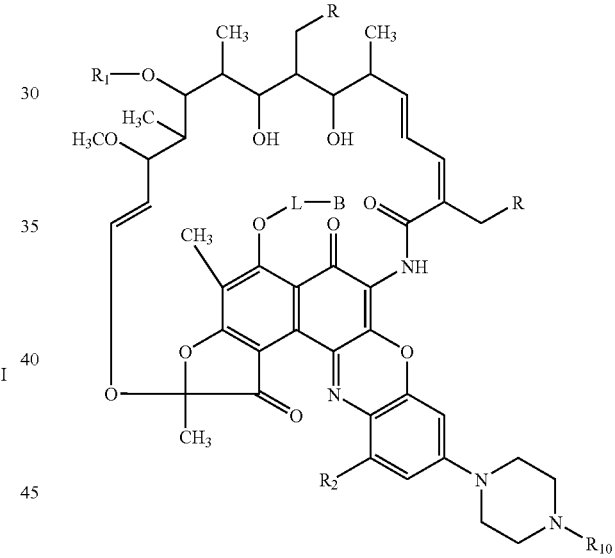
wherein L is a linker described by formulas XXI, XXII, XXIII, XXIV, or XXV and B is selected from one of formulas XXXVI–XLVII:
XXXVI
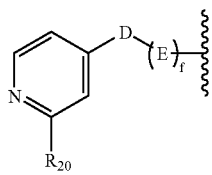
XXXVII
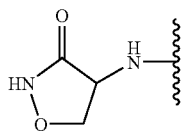

XXXVIII
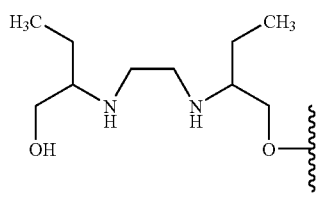
XXXIX
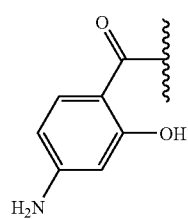
XL
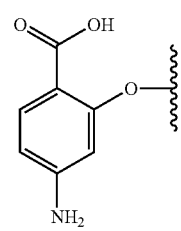
XLI
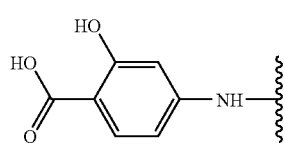
XLII
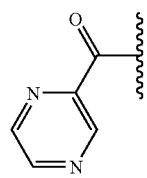
XLIII
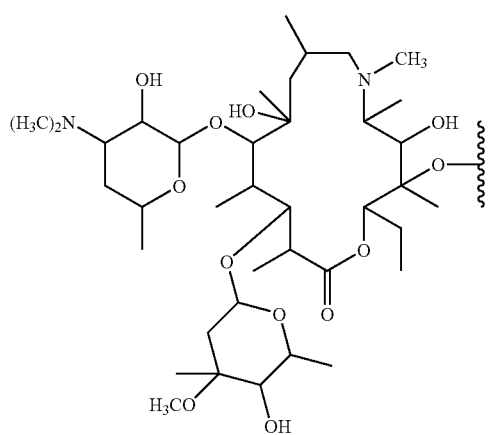
XLIV
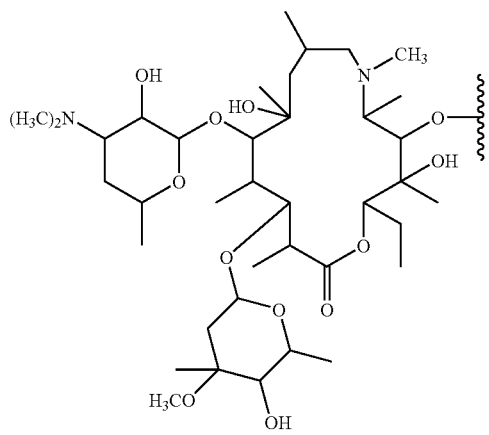
XLV
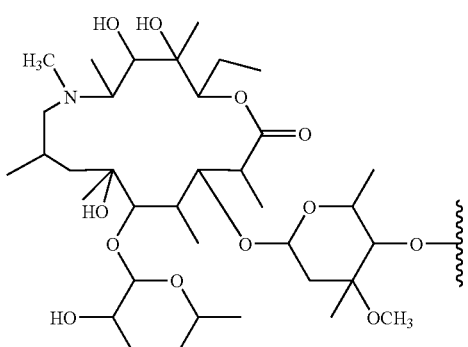
XLVI
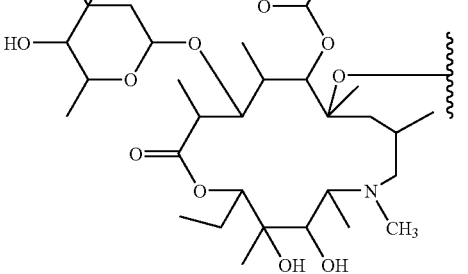
XLVII In formulas XXVI–XLVII, R represents a hydrogen atom, a hydroxyl group or —OR*, $R_1$ is —H, or —C(O)CH$_3$; $R_2$ represents a hydroxyl group or a sulfhydryl group; $R_{10}$ is selected from the group consisting of methyl, ethyl, iso-propyl, n-propyl, iso-butyl, (S)-sec-butyl, and (R)-sec-butyl; D is a carbonyl, thiocarbonyl, or methylene; E is —NR$_{21}$, —O—, —S—, —NH—NH—, or —NH—N=; f is 0 or 1; $R_{20}$ is H or ethyl; $R_{21}$ is H or alkyl; and $R_{22}$ is methyl or cyclo-pentyl. R* is a bond in a linkage group formed with (L).

In another aspect, the invention features compounds of formulas LXVI.

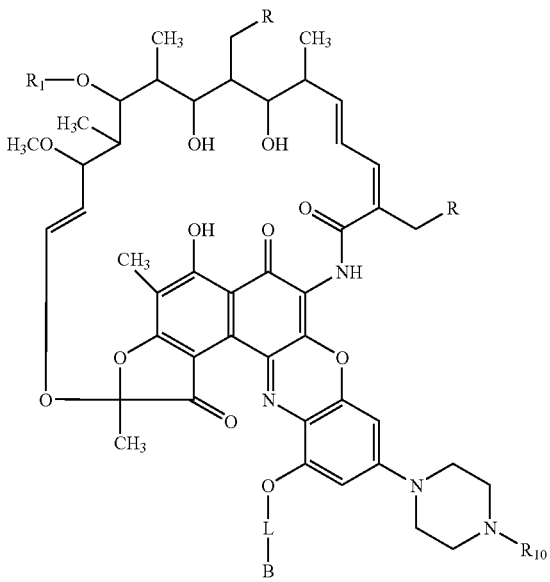

LXVI wherein R represents a hydrogen atom or a hydroxyl group. $R_1$ represents a hydrogen atom or an acetyl group. $R_{10}$ represents a hydrogen atom, an alkyl group having 1 to 6 carbon atoms, or —(CH$_2$)$_n$X$_3$ in which n represents an integer between 1 and 4. $X_3$ represents an alkoxy group having 1 to 3 carbon atoms, a vinyl group, or an ethynyl group. (L) is a linker and (B) is a therapeutic drug.

In particular embodiments, linker (L) is a chemical bond linking an oxygen atom of a rifamycin derivative of formulas XXVI–XXXV to a carbonyl or thiocarbonyl moiety present in drug B, such that the linkage group is an ester or thioester.

In another aspect, the invention features a method of preventing, stabilizing, or inhibiting the growth of microbes, or killing microbes. The method includes contacting microbes or a site susceptible to microbial growth with one or more compounds of the invention in amounts sufficient to prevent, stabilize, or inhibit the growth of the microbes, or kill the microbes.

In one embodiment of the above aspect, the step of contacting microbes or a site susceptible to microbial growth with the compound includes administering to a mammal the compound in an amount sufficient to treat, stabilize, or prevent the microbial infection.

The microbial infection to be treated or prevented by the compound of the invention can be an infection by a bacterium, such as *Acinetobacter calcoaceticus, A. haemolyticus, Aeromonas hydrophilia, Bacteroides fragilis, B. distasonis,* Bacteroides 3452A homology group, *B. vulgatus, B. ovalus, B. thetaiotaomicron, B. uniformis, B. eggerthii, B. splanchnicus, Branhamella catarrhalis, Campylobacter fetus, C. jejuni, C. coli, Citrobacter freundii, Clostridium difficile, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. macginleyi, C. matruchoti, C. mucifaciens, C. pilosum, C. propinquum, C. renale, C. riegelii, C. sanguinis, C. singulare, C. striatum, C. sundsvallense, C. thomssenii, C. urealyticum, C. xerosis, Enterobacter cloacae, E. aerogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Francisella tularensis, Gardnerella vaginalis, Helicobacter pylori, Kingella dentrificans, K. kingae, K. oralis, Klebsiella pneumoniae, K. oxytoca, Moraxella catarrhalis, M. atlantae, M. lacunata, M. nonliquefaciens, M. osloensis, M. phenylpyruvica, Morganella morganii, Parachlamydia acanthamoebae, Pasteurella multocida, P. haemolytica, Proteus mirabilis, Proteus vulgaris, Providencia alcalifaciens, P. rettgeri, P. stuartii, Serratia marcescens, Simkania negevensis, Streptococcus pneumoniae, S. agalactiae, S. pyogenes, Treponema pallidum, Vibrio cholerae,* and *V. parahaemolyticus*. Accordingly, the invention features a method of treating infections by the bacteria above, among others.

In another embodiment, the microbial infection to be treated or prevented by one or more compounds of the invention is an intracellular infection by a facultative or obligate intracellular microbe.

Compounds of the invention may be used to treat or prevent bacterial infections by facultative intracellular bacteria, such as *Bordetella pertussis, B. arapertussis, B. bronchiseptica, Burkholderia cepacia, Escherichia coli, Haemophilus actinomycetemcomitans, H. aegyptius, H. aphrophilus, H. ducreyi, H. felis, H. haemoglobinophilus, H. haemolyticus, H. influenzae, H. paragallinarum, H. parahaemolyticus, H. parainfluenzae, H. paraphrohaemolyticus, H. paraphrophilus, H. parasuis, H. piscium, H. segnis, H. somnnus, H. vaginalis, Legionella adelaidensis, L. anisa, L. beliardensis, L. birminghamensis, L. bozemanii, L. brunensis, L. cherrii, L. cincinnatiensis, Legionella drozanskii L. dumoffii, L. erythra, L. fairfieldensis, L. fallonii, L. feeleii, L. geestiana, L. gormanii, L. gratiana, L. gresilensis, L. hackeliae, L. israelensis, L. jordanis, L. lansingensis, Legionella londiniensis L. longbeachae, Legionella lytica L. maceachernii, L. micdadei, L. moravica, L. nautarum, L. oakridgensis, L. parisiensis, L. pittsburghensis, L. pneumophila, L. quateirensis, L. quinlivanii, L. rowbothamii, L. rubrilucens, L. sainthelensi, L. santicrucis, L. shakespearei, L. spiritensis, L. steigerwaltii, L. taurinensis, L. tucsonensis, L. wadsworthii, L. waltersii, L. worsleiensis, Listeria denitrificans, L. grayi, L. innocua, L. ivanovii, L. monocytogenes, L. seeligeri, L. welshimeri, Mycobacterium abscessus, M. africanum, M. agri, M. aichiense, M. alvei, M. asiaticum, M, aurum, M. austroafricanum, M. avium, M. bohemicum, M. bovis, M. branderi, M. brumae, M. celatum, M. chelonae, M. chitae, M. chlorophenolicum, M. chubuense, M. confluentis, M. conspicuum, M. cookii, M. diernhoferi, M. doricum, M. duvalii, M. elephantis, M. fallax, M. farcinogenes, M. flavescens, M. fortuitum, M. frederiksbergense, M. gadium, M. gastri, M. genavense, M. gilvum, M. goodii, M. gordonae, M. haemophilum, M. hassiacum, M. heckeshornense, M.*

*heidelbergense, M. hiberniae, M. immunogenum, M. intracellulare, M. interjectum, M. intermedium, M. kansasii, M. komossense, M. kubicae, M. lentiflavum, M. leprae, M. lepraemurium, M. luteum, M. madagascariense, M. mageritense, M. malmoense, M. marinum, M. microti, M. moriokaense, M. mucogenicum, M. murale, M. neoaurum, M. nonchromogenicum, M. novocastrense, M. obuense, M. parafortuitum, M. paratuberculosis, M. peregrinum, M. phage, M. phlei, M. porcinum, M. poriferae, M. pulveris, M. rhodesiae, M. scrofulaceum, M. senegalense, M. septicum, M. shimoidei, M. simiae, M. smegmatis, M. sphagni, M. szulgai, M. terrae, M. thermoresistibile, M. tokaiense, M. triplex, M. triviale, M. tuberculosis, M. tusciae, M. ulcerans, M. vaccae, M. wolinskyi, M. xenopi, Neisseria animalis, N. canis, N. cinerea, N. denitrificans, N. dentiae, N. elongata, N. flava, N. flavescens, N. gonorrhoeae, N. iguanae, N. lactamica, N. macacae, N. meningitidis, N. mucosa, N. ovis, N. perflava, N. pharyngis* var. *flava, N. polysaccharea, N. sicca, N. subflava, N. weaveri, Pseudomonas aeruginosa, P. alcaligenes, P. chlororaphis, P. luorescens, P. luteola, P. mendocina, P. monteilii, P. oryzihabitans, P. pertocinogena, P. pseudalcaligenes, P. putida, P. stutzeri, Salmonella bacteriophage, S. bongori, S. choleraesuis, S. enterica, S. enteritidis, S. paratyphi, S. typhi, S. typhimurium, S. typhimurium, S. typhimurium bacteriophage, S. typhimurium, S. typhimurium bacteriophage, Shigella boydii, S. dysenteriae, S. flexneri, S. sonnei, Staphylococcus arlettae, S. aureus, S. auricularis, S. bacteriophage, S. capitis, S. caprae, S. carnosus, S. caseolyticus, S. chromogenes, S. cohnii, S. delphini, S. epidermidis, S. equorum, S. felis, S. fleurettii, S. gallinarum, S. haemolyticus, S. hominis, S. hyicus, S. intermedius, S. kloosii, S. lentus, S. lugdunensis, S. lutrae, S. muscae, S. mutans, S. pasteuri, S. phage, S. piscifermentans, S. pulvereri, S. saccharolyticus, S. saprophyticus, S. schleijeri, S. sciuri, S. simulans, S. succinus, S. vitulinus, S. warneri, S. xylosus, Ureaplasma urealyticum, Yersinia aldovae, Y. bercovieri, Y. enterocolitica, Y. frederiksenii, Y. intermedia, Y. kristensenii, Y. mollaretii, Y. pestis, Y. philomiragia, Y. pseudotuberculosis, Y. rohdei,* and *Y. ruckeri*. Compounds of the invention may also be used to treat or prevent bacterial infections by obligate intracellular bacteria, such as *Anaplasma bovis, A. caudatum, A. centrale, A. marginale A. ovis, A. phagocytophila, A. platys, Bartonella bacilliformis, B. clarridgeiae, B. elizabethae, B. henselae, B. henselae phage, B. quintana, B. taylorii, B. vinsonii, Borrelia afzelii, B. andersonii, B. anserina, B. bissettii, B. burgdorferi, B. crocidurae, B. garinii, B. hermsii, B. japonica, B. miyamotoi, B. parkeri, B. recurrentis, B. turdi, B. turicatae, B. valaisiana, Brucella abortus, B. melitensis, Chlamydia pneumoniae, C. psittaci, C. trachomatis, Cowdria ruminantium, Coxiella burnetii, Ehrlichia canis, E. chaffeensis, E. equi, E. ewingii, E. muris, E. phagocytophila, E. platys, E. risticii, E. ruminantium, E. sennetsu, Haemobartonella canis, H. felis, H. muris, Mycoplasma arthriditis, M. buccale, M. faucium, M. fermentans, M. genitalium, M. hominis, M. laidlawii, M. lipophilum, M. orale, M. penetrans, M. pirum, M. pneumoniae, M. salivarium, M. spermatophilum, Rickettsia australis, R. conorii, R. felis, R. helvetica, R. japonica, R. massiliae, R. montanensis, R. peacockii, R. prowazekii, R. rhipicephali, R. rickettsii, R. sibirica,* and *R. typhi*. Accordingly, the invention features a method of treating infections caused by the obligate and facultative intracellular bacteria above, among others.

Compounds of the invention may be used to treat or prevent fungal infections by a facultative intracellular fungi, such as *Candida aaseri, C. acidothermophilum, C. acutus, C. albicans, C. anatomiae, C. apis, C. apis* var. *galacta, C. atlantica, C. atmospherica, C. auringiensis, C. bertae, C. berthtae* var. *chiloensis, C. berthetii, C. blankii, C. boidinii, C. boleticola, C. bombi, C. bombicola, C. buinensis, C. butyri, C. cacaoi, C. cantarellii, C. cariosilignicola, C. castellii, C. castrensis, C. catenulata, C. chilensis, C. chiropterorum, C. coipomensis, C. dendronema, C. deserticola, C. diddensiae, C. diversa, C. entomaea, C. entomophila, C. ergatensis, C. ernobii, C. ethanolica, C. ethanothermophilum, C. famata, C. fluviotilis, C. fragariorum, C. fragicola, C. riedrichii, C. fructus, C. geochares, C glabrata, C. glaebosa, C. gropengiesseri, C. guilliermondii, C. guilliermondii* var. *galactosa, C. guilliermondii* var. *soya, C. haemulonii, C. halophila/C. versatilis, C. holmii, C. humilis, C. hydrocarbofumarica, C. inconspicua, C. insectalens, C. insectamans, C. intermedia, C. javanica, C. kefyr, C. krissii, C. krusei, C krusoides, C. lambica, C. lusitaniae, C. magnoliae, C. maltosa, C. mamillae, C. maris, C. maritima, C. melibiosica, C. melinii, C. methylica, C. milleri, C. mogii, C. molischiana, C. montana, C. multis-gemmis, C. musae, C. naeodendra, C. nemodendra, C. nitratophila, C. norvegensis, C. norvegica, C. oleophila, C. oregonensis, C. osornensis, C. paludigena, C. parapsilosis, C. pararugosa, C. periphelosum, C. petrohuensis, C. petrophilum, C. philyla, C. pignaliae, C. pintolopesii* var. *pintolopesii, C. pintolopesii* var. *slooffiae, C. pinus, C. polymorpha, C. populi, C. pseudointermedia, C. quercitrasa, C. railenensis, C. rhagii, C. rugopelliculosa, C. rugosa, C. sake, C. salmanticensis, C. savonica, C. sequanensis, C. shehatae, C. silvae, C. silvicultrix, C. solani, C. sonorensis, C. sorbophila, C. spandovensis, C. sphaerica, C. stellata, C. succiphila, C. tenuis, C. terebra, C. tropicalis, C. utilis, C. valida, C. vanderwaltii, C. vartiovaarai, C. veronae, C. vini, C. wickerhamii, C. xestobii, C. zeylanoides,* and *Histoplasma capsulatum*. Accordingly, the invention features a method of treating an infection by the facultative intracellular fungi above, among others.

Obligate intracellular protozoans can also be treated by a compound of the invention. Obligate intracellular protozoans include, for example, *Brachiola vesicularum, B. connori, Encephalitozoon cuniculi, E. hellem, E. intestinalis, Enterocytozoon bieneusi, Leishmania aethiopica, L. amazonensis, L. braziliensis, L. chagasi, L. donovani, L. donovani chagasi, L. donovani donovani, L. donovani infantum, L. enriettii, L. guyanensis, L. infanturn, L. major, L. mexicana, L. panamensis, L. peruviana, L. pifanoi, L. tarentolae, L. tropica, Microsporidium ceylonensis, M. africanum, Nosema connori, N. ocularum, N. algerae, Plasmodium berghei, P. brasilianum, P. chabaudi, P. chabaudi adami, P. chabaudi chabaudi, P. cynomolgi, P. falciparum, P. fragile, P. gallinaceum, P. knowlesi, P. lophurae, P. malariae, P. ovale, P. reichenowi, P. simiovale, P. simium, P. vinckei petteri, P. vinckei vinckei, P. vivax, P. yoelii, P. yoelii nigeriensis, P. yoelii yoelii, Pleistophora anguillarum, P. hippoglossoideos, P. miirandellae, P. ovariae, P. typicalis, Septata intestinalis, Toxoplasma gondii, Trachipleistophora hominis, T. anthropophthera, Vittaforma corneae, Trypanosoma avium, T. brucei, T brucei brucei, T. brucei gambiense, T. brucei rhodesiense, T. cobitis, T. congolense, T. cruzi, T. cyclops, T. equiperdum, T. evansi, T. dionisii, T. godfreyi, T. grayi, T. lewisi, T. mega, T. microti, T. pestanai, T. rangeli, T. rotatorium, T. simiae, T. theileri, T. varani, T. vespertilionis,* and *T. vivax*. Accordingly, the invention features a method of treating infections by the obligate intracellular protozoa above, among others.

Compounds of the invention may also be used to treat or prevent viral infections.

The invention further features a method for treating or preventing the development of an atherosclerosis-associated disease in a patient by administering to the patient a compound of the invention, wherein therapeutic drug (B) is an anti-inflammatory agent, a statin, an antibacterial agent, a platelet aggregation inhibitor, a blood thinning agent, or a lipid lower agent, in an amount effective to treat or prevent the development of the atherosclerosis-associated disease in the patient.

Desirable anti-inflammatory agents include non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, and salsalte) and steroids (e.g., cortisone, dexamethasone, hydrocortisone, methylprednisolone, prednisolone, prednisone, triamcinolone).

Desirable statins include atorvastatin, rosuvastatin, lovastatin, simvastatin, pravastatin, cerivastatin, and fluvastatin.

The invention also features a method of reducing the level of C-reactive protein in a patient in need thereof by administering to the patient a compound of the invention, wherein therapeutic drug (B) is an anti-inflammatory agent, a statin, an antibacterial agent, a platelet aggregation inhibitor, a blood thinning agent, or a lipid lower agent, in an amount effective to reduce the level of C-reactive protein in the patient. Preferred anti-inflammatory agents and statins are listed above.

In another aspect, the invention features a pharmaceutical composition that includes a compound described herein in any pharmaceutically acceptable form, including isomers such as diastereomers and enantiomers, salts, solvates, and polymorphs thereof. In various embodiments, the composition includes a compound of the invention along with a pharmaceutically acceptable carrier or diluent. In still further embodiments, the pharmaceutical composition includes a compound with the chemical structure of formulas XXVI–XXXV.

In another aspect, the invention features a method of treating a microbial infection in an animal by co-administering a compound of the invention along with one or more antifungal agents, antiviral agents, antibacterial agents, or antiprotozoan agents, or combinations thereof.

In the generic descriptions of compounds of this invention, the number of atoms of a particular type in a substituent group is generally given as a range. For example, an alkyl group containing from 1 to 10 carbon atoms. Reference to such a range is intended to include specific references to groups having each of the integer number of atoms within the specified range. For example, an alkyl group from 1 to 10 carbon atoms includes each of $C_1$, $C_2$, $C_3$, $C_4$, $C_5$, $C_6$, $C_7$, $C_8$, $C_9$, and $C_{10}$. Other numbers of atoms and other types of atoms are indicated in a similar manner.

By "alkyl" is meant a branched or unbranched saturated hydrocarbon group, desirably having from 1 to 20 carbon atoms. An alkyl may optionally include monocyclic, bicyclic, or tricyclic rings, in which each ring desirably has three to six members. The alkyl group may be substituted or unsubstituted. Exemplary substituents include alkoxy, aryloxy, sulfhydryl, alkylthio, arylthio, halogen, hydroxyl, fluoroalkyl, perfluoralkyl, amino, aminoalkyl, disubstituted amino, quaternary amino, hydroxyalkyl, carboxyalkyl, and carboxyl groups.

By "alkene" is meant a branched or unbranched hydrocarbon group containing one or more double bonds, desirably having from 2 to 20 carbon atoms. An alkene may optionally include monocyclic, bicyclic, or tricyclic rings, in which each ring desirably has five or six members. The alkene group may be substituted or unsubstituted. Exemplary substituents include alkoxy, aryloxy, sulflhydryl, alkylthio, arylthio, halogen, hydroxyl, fluoroalkyl, perfluoralkyl, amino, aminoalkyl, disubstituted amino, quaternary amino, hydroxyalkyl, carboxyalkyl, and carboxyl groups.

By "alkyne" is meant a branched or unbranched hydrocarbon group containing one or more triple bonds, desirably having from 2 to 20 carbon atoms. An alkyne may optionally include monocyclic, bicyclic, or tricyclic rings, in which each ring desirably has five or six members. The alkyne group may be substituted or unsubstituted. Exemplary substituents include alkoxy, aryloxy, sulfhydryl, alkylthio, arylthio, halogen, hydroxyl, fluoroalkyl, perfluoralkyl, amino, aminoalkyl, disubstituted amino, quaternary amino, hydroxyalkyl, carboxyalkyl, and carboxyl groups.

By "heteroalkyl" is meant a branched or unbranched group in which one or more methylenes (—$CH_2$—) are replaced by nitrogen, oxygen, sulfur, carbonyl, thiocarbonyl, phosphoryl, sulfonyl, or NR, where R is an alkyl. Some examples include tertiary amines, ethers, thioethers, amides, thioamides, carbamates, thiocarbamates, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halogen, hydroxyl, fluoroalkyl, perfluoralkyl, amino, aminoalkyl, disubstituted amino, quaternary amino, hydroxyalkyl, carboxyalkyl, and carboxyl groups By "aromatic residue" is meant an aromatic group having a ring system with conjugated $\pi$ electrons (e.g., phenyl, or imidazole ). The ring of the aryl group is preferably 5 to 10 atoms. The aromatic ring may be exclusively composed of carbon atoms or may be composed of a mixture of carbon atoms and heteroatoms. Preferred heteroatoms include nitrogen, oxygen, sulfur, and phosphorous. Aryl groups may optionally include monocyclic, bicyclic, or tricyclic rings, where each ring has preferably five or six members. The aryl group may be substituted or unsubstituted. Exemplary substituents include alkyl, hydroxyl, alkoxy, aryloxy, sulflhydryl, alkylthio, arylthio, halogen, fluoroalkyl, carboxyl, carboxyalkyl, amino, aminoalkyl, monosubstituted amino, disubstituted amino, and quaternary amino groups.

The term "cyclic system" refers to a compound that contains one or more covalently closed ring structures, in which the atoms forming the backbone of the ring are composed of any combination of the following: carbon, oxygen, nitrogen, sulfur, and phosphorous. The cyclic system may be substituted or unsubstituted. Exemplary substituents include, without limitation, alkyl, hydroxyl, alkoxy, aryloxy, sulflhydryl, alkylthio, arylthio, halogen, fluoroalkyl, carboxyl, carboxyalkyl, amino, aminoalkyl, monosubstituted amino, disubstituted amino, and quaternary amino groups.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is an alkyl group.

By "hydroxyalkyl" is meant a chemical moiety with the formula —(R)—OH, wherein R is an alkyl group.

By "alkoxy" is meant a chemical substituent of the formula —OR, wherein R is an alkyl group.

By "aryloxy" is meant a chemical substituent of the formula —OR, wherein R is an aryl group.

By "alkylthio" is meant a chemical substituent of the formula —SR, wherein R is an alkyl group.

By "arylthio" is meant a chemical substituent of the formula —SR, wherein R is an aryl group.

By "quaternary amino" is meant a chemical substituent of the formula —(R)—N(R')(R")(R''')$^+$, wherein R, R', R", and R''' are each independently an alkyl, alkene, alkyne, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

The term "linkage group" refers to the covalent bond that results from the combination of reactive moieties of linker (L) with functional groups of (A) or (B). Examples of linkage groups include, without limitation, ester, carbamate, thioester, imine, disulfide, amide, ether, thioether, sulfonamide, isourea, isothiourea, imidoester, amidine, phosphoramidate, phosphodiester, thioether, and hydrazone.

By "cleavable" or "cleavable linker" is meant a linker (L) which is degraded in vivo, such that (A) and (B) are no longer covalently attached. Cleavable linkers contain linkage groups which are biodegradable or chemically sensitive or which incorporate enzymatic cleavage sites (i.e., an ester linkage susceptible to cleavage by esterase enzymes).

By "drug" is meant an agent having a beneficial effect on a specific disease in a living human or non-human mammal.

As used herein, the term "treating" refers to administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to ameliorate the disease and improve the patient's condition. Thus, in the claims and embodiments, treating is the administration to a mammal either for therapeutic or prophylactic purposes.

The term "microbial infection" refers to the invasion of the host mammal by pathogenic microbes (e.g., bacteria, fungi, yeasts, viruses, protozoa). This includes the excessive growth of microbes that are normally present in or on the body of a mammal. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the presence of a microbial population(s) is damaging the cells or other tissue of a mammal.

The term "microbes" includes, for example, bacteria, fungi, yeasts, viruses and protozoa.

By "intracellular pathogen" is meant an infection by any facultative or obligate intracellular microbe.

By "obligate intracellular pathogen" is meant a microbe which must use an intracellular location (e.g., a host cell) in order to replicate.

By "facultative intracellular pathogen" is meant a microbe which is able to survive within an intracellular location (e.g., a host cell), but does not require an intracellular environment to replicate.

The term "administration" or "administering" refers to a method of giving a dosage of a pharmaceutical composition to a mammal, where the method is, e.g., topical, oral, intravenous, intraperitoneal, or intramuscular. The preferred method of administration can vary depending on various factors, e.g., the components of the pharmaceutical composition, site of the potential or actual disease and severity of disease.

The term "mammal" specifically includes humans, cattle, pigs, sheep, horses, dogs, and cats, but also includes many other species.

By "atherosclerosis" is meant the progressive accumulation of smooth muscle cells, inflammatory cells, lipid products (e.g., lipoproteins, or cholesterol), cellular waste products, calcium, or other substances within the inner lining of an artery, resulting in the narrowing or obstruction of the blood vessel and the development of atherosclerosis-associated diseases. Atherosclerosis is typically manifested within large and medium-sized arteries, and is often characterized by a state of chronic inflammation within the arteries.

By "atherosclerosis-associated disease" is meant any disorder that is caused by or is associated with atherosclerosis. Typically, atherosclerosis of the coronary arteries commonly causes coronary artery disease, myocardial infarction, coronary thrombosis, and angina pectoris. Atherosclerosis of the arteries supplying the central nervous system frequently provokes strokes and transient cerebral ischemia. In the peripheral circulation, atherosclerosis causes intermittent claudication and gangrene and can jeopardize limb viability. Atherosclerosis of an artery of the splanchnic circulation can cause mesenteric ischemia. Atherosclerosis can also affect the kidneys directly (e.g., renal artery stenosis).

A patient who is being treated for an atherosclerosis-associated disease is one who a medical practitioner has diagnosed as having such a disease. Diagnosis may be by any suitable means. Methods for diagnosing atherosclerosis by measuring systemic inflammatory markers are described, for example, in U.S. Pat. No. 6,040,147, hereby incorporated by reference. Diagnosis may employ an electrocardiogram, chest X-ray, echocardiogram, cardiac catheterization, or measurement of blood levels of CPK, CPK-MB, myoglobin, troponin, homocysteine, or C-reactive protein. A patient in whom the development of an atherosclerosis-associated disease is being prevented is one who has not received such a diagnosis. One in the art will understand that these patients may have been subjected to the same tests (electrocardiogram, chest X-ray, etc.) or may have been identified, without examination, as one at high risk due to the presence of one or more risk factors (e.g., family history, hypertension, diabetes mellitus, high cholesterol levels). Thus, prophylactic administration of a compound of the invention is considered to be preventing the development of an atherosclerosis-associated disease.

An atherosclerosis-associated disease has been treated or prevented when one or more tests of the disease (e.g., any of the those described above) indicate that the patient's, condition has improved or the patient's risk is reduced. In one example, a reduction in C-reactive protein to normal levels indicates that an atherosclerosis-associated disease has been treated or prevented.

BRIEF DESCRIPTION OF THE DRAWINGS

FIG. 2 is a table of structures identifying exemplary therapeutic drugs or therapeutically active drug metabolites to be targeted by conjugation to a rifamycin derivative.

FIG. 3 is a table of rifamycin derivatives of formulas III and/or XX. R and $R_1$ are defined as in formula XX.

DETAILED DESCRIPTION

Figure 1:
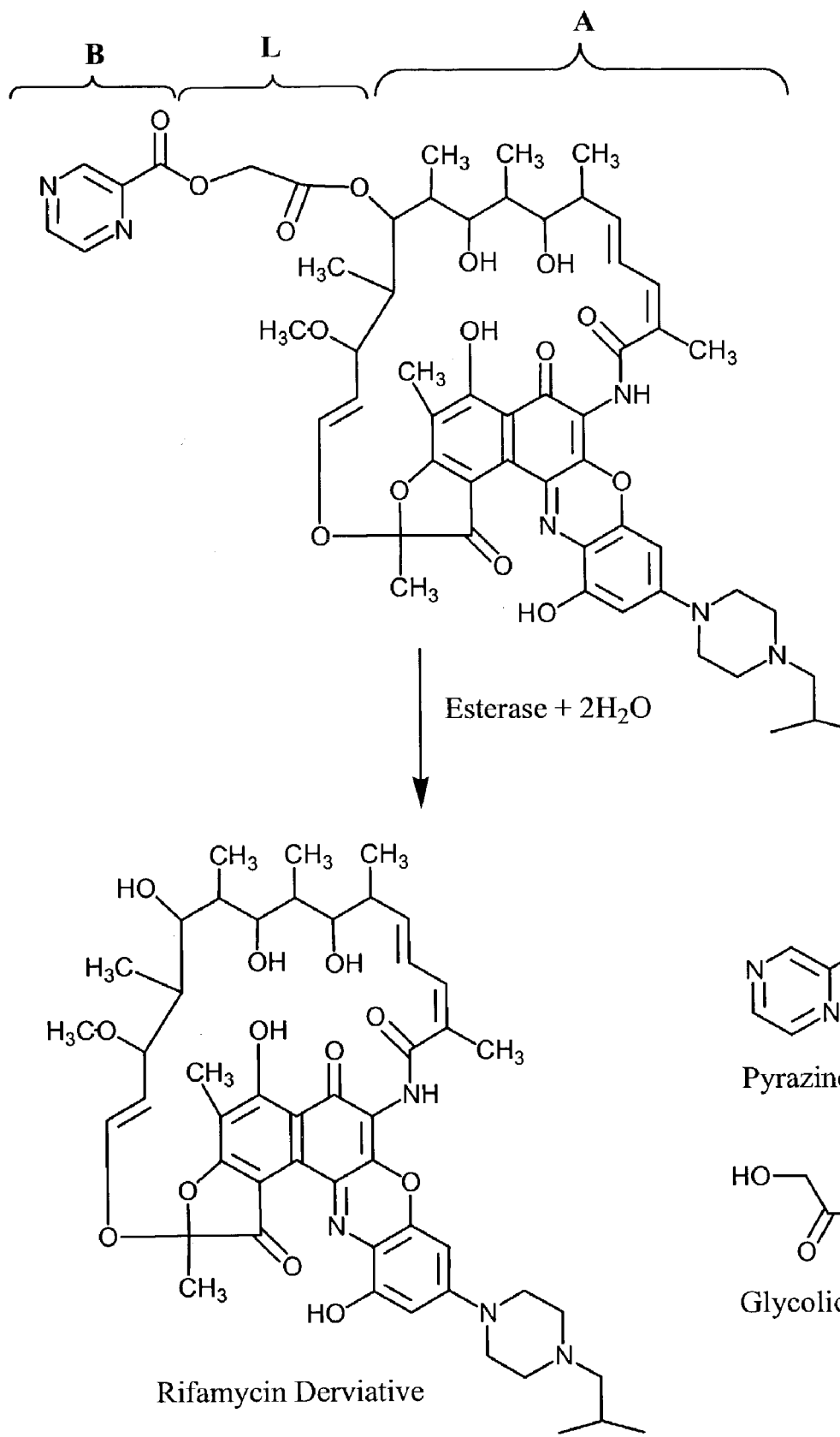
FIG. 1 is a schematic illustration depicting the enzymatic degradation of a rifamycin-PZA conjugate.

We have discovered that rifamycin derivatives can serve as targeting moieties for other therapeutic compounds. The compounds of the present invention have three characteristic components: a rifamycin derivative (A) covalently tethered via a linker (L) to a therapeutic drug (B). They are described by formula I.

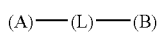

I wherein (A) is a rifamycin derivative of formula II:

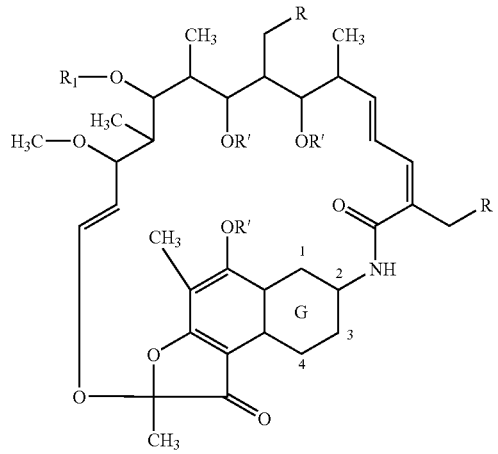

II

In formula II, each methine proton, methylene proton, and methyl proton is optionally substituted by —OH or —OR*, R represents a hydrogen atom, a hydroxyl group, or —OR*, $R_1$ represents a hydrogen atom, an acetyl group, or R*, and ring G is selected from formulas III–XI:

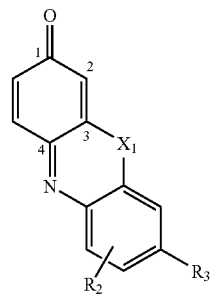

III

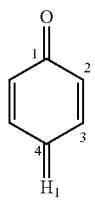

IV

-continued

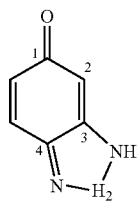

V

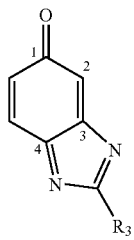

VI

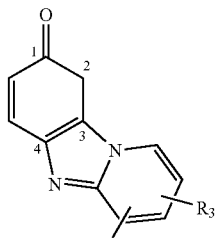

VII

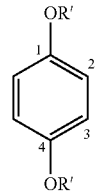

VIII

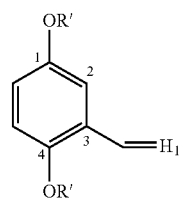

IX

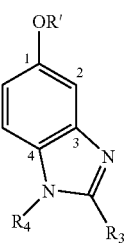

X

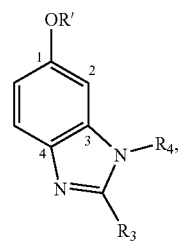

XI

In the formulas above, R' represents a hydrogen atom or R*, $X_1$ represents an oxygen atom or a sulfur atom, $H_1$ represents an oxygen atom, N—$R_3$ or R*, and $H_2$ represents a group expressed by formulas XII or XIII:

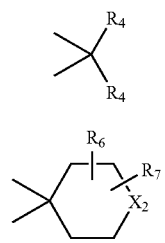

XII

XIII $R_2$ represents a hydroxyl group, a sulfhydryl group, a hydrogen atom, or an alkyl group having 1 to 3 carbon atoms. $R_3$ represents a hydrogen atom, an alkyl group having 1 to 10 carbon atoms, or a group expressed by one of formulas XIV–XVI:

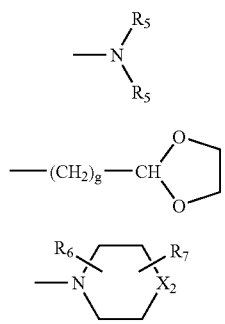

XIV

XV

XVI

Each $R_4$ is, independently, a hydrogen atom or an alkyl group having 1 to 7 carbon atoms. Each $R_5$ is, independently, an alkyl group having 1 to 7 carbon atoms, or two of $R_5$ in combination form a 3–8 membered cyclic system. In formula XV, g represents an integer between 1 and 3. $R_6$ and $R_7$ are each, independently, a hydrogen atom or an alkyl group having 1 to 3 carbon atoms. $X_2$ represents an oxygen atom, a sulfur atom, a carbonyl group, or a group expressed by one of formulas XVII–XIX:

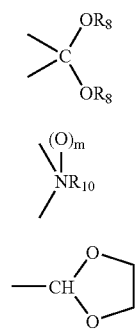

XVII

XVIII

XIX $R_8$ and $R_9$ are each, independently, a hydrogen atom, or an alkyl group having 1 to 3 carbon atoms, or $R_8$ and $R_9$, in combination with each other, represent —$(CH_2)_k$—, in which k represents an integer between 1 and 4. In formula XVIII, m represents 0 or 1. $R_{10}$ represents a hydrogen atom, an alkyl group having 1 to 6 carbon atoms, or —$(CH_2)_nX_3$, in which n represents an integer between 1 and 4. $X_3$ represents an alkoxy group having 1 to 3 carbon atoms, a vinyl group, or an ethynyl group. In all of the formulas above, R* is a bond in a linkage group between (A) and (L). (L) is a linker which forms linkage groups with rifamycin derivative (A) and therapeutic drug (B).

Therapeutic drug (B) can also be tethered to the ring system in the rifamycin derivative. Examples include compounds of formulas LXVI.

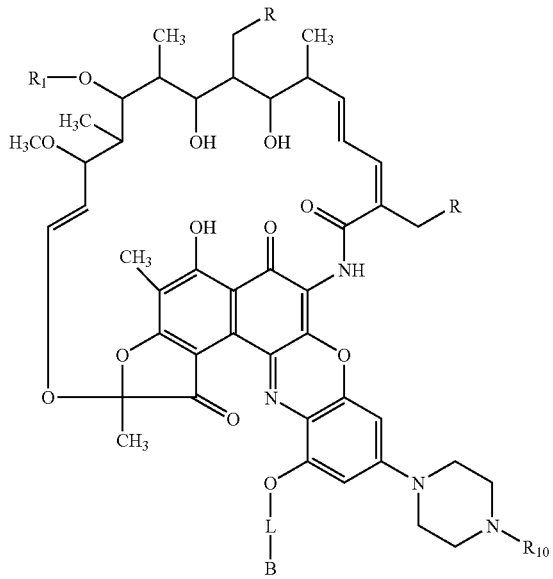

LXVI wherein R represents a hydrogen atom or a hydroxyl group. $R_1$ represents a hydrogen atom or an acetyl group. $R_{10}$ represents a hydrogen atom, an alkyl group having 1 to 6 carbon atoms, or —$(CH_2)_nX_3$ in which n represents an integer between 1 and 4. $X_3$ represents an alkoxy group having 1 to 3 carbon atoms, a vinyl group, or an ethynyl group. (L) is a linker and (B) is a therapeutic drug.

A description of how these compounds are prepared is provided below and in the examples.

Rifamycin Derivative (A)

The rifamycin derivatives of formula III can be synthesized by the methods disclosed in *Chem. Pharm. Bull.*, 41:148, 1993 and U.S. Pat. Nos. 4,690,919; 4,983,602; 5,786,349; 5,981,522; and 4,859,661, each of which is hereby incorporated by reference.

Figure 3:
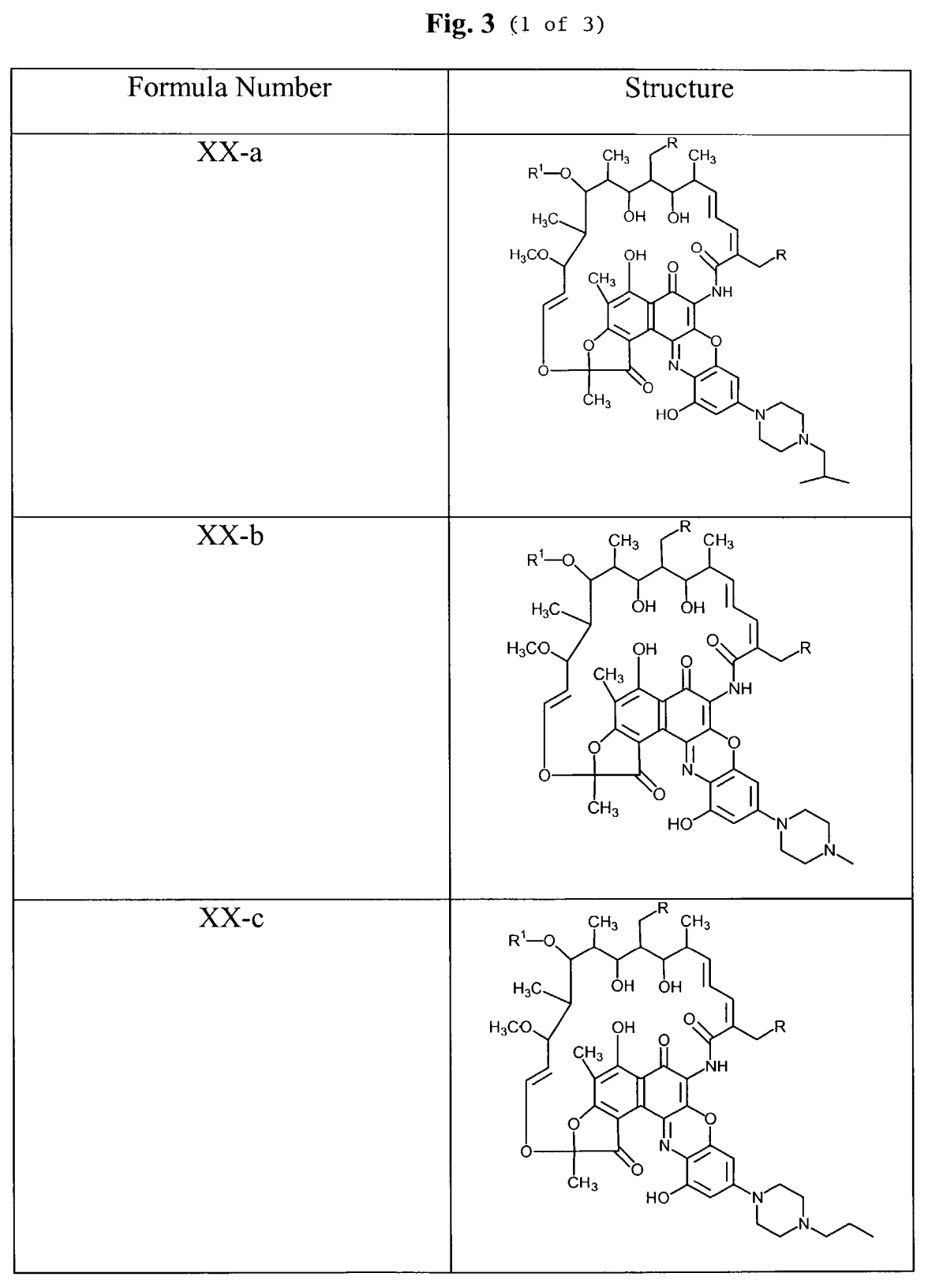

Rifamycin derivatives of the invention include those of formula XXa–XXf and IIIa (structures provided in FIG. 3), wherein $R_1$ or R has been chemically modified, where necessary, to allow —(L)—(B), —OH, or —O—(L)—(B) to be placed at these positions. The enzymatic oxidation of R for a compound of formula XXa ($R_1$ is acetyl, R is hydrogen) is described by Mae et al., *Xenobiotica*, 30:565 (2000); hereby incorporated by reference. A description of how these modifications are made is provided in Example 2.

The synthesis of rifamycin derivatives of formula XX in which $R_2$ is sulfhydryl or in which $X_1$ is a sulfur atom is provided in Example 13.

Rifamycin derivatives of formulas III–XI can be prepared from 3-formyl-rifamycin SV, formula XLVIII, 3-amino-4-deoxo-4-imino rifamycin S, formula XLIX, 3-halorifamycin S, formula L, rifamycin SV, formula LI, or rifamycin S, formula LII.

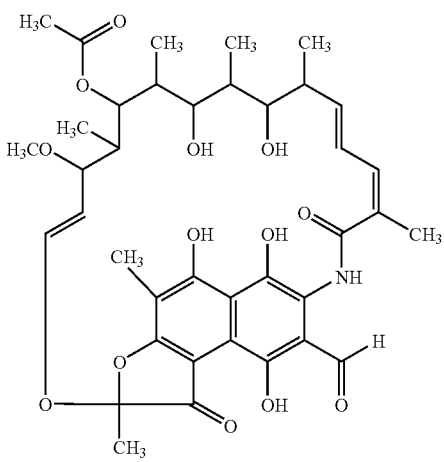

XLVIII

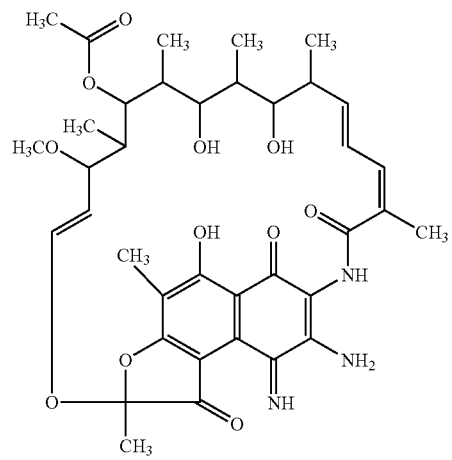

XLIX

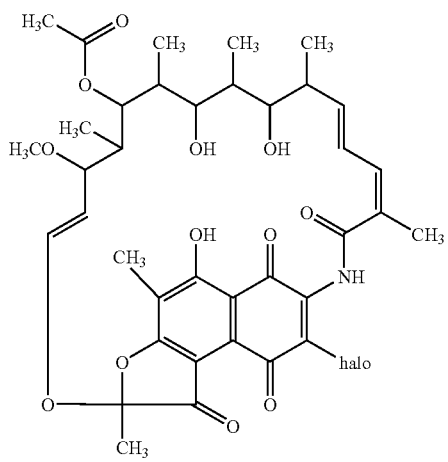

L

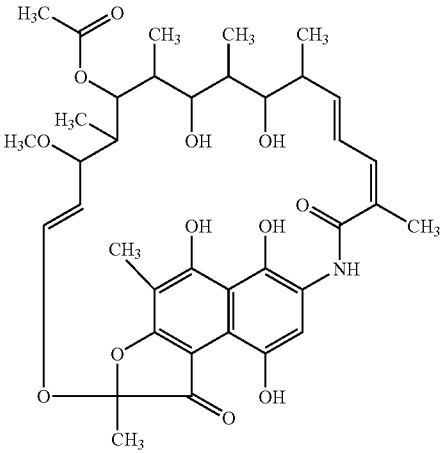

LI

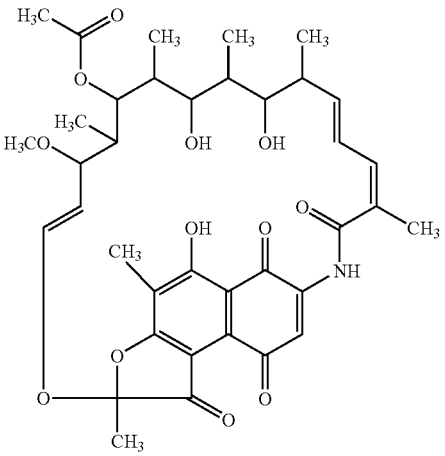

LII

The preparation of 3-formyl-rifamycin SV is described in U.S. Pat. No. 3,342,810. 3-formyl-rifamycin SV can be used in the preparation of rifamycin derivatives of formula IX, as described in U.S. Pat. Nos. 3,342,810, 4,551,450, 4,681,938, each of which is hereby incorporated by reference.

The preparation of 3-amino-4-deoxo-4-imino rifamycin S is described in U.S. Pat. No. 4,017,481. 3-amino-4-deoxo-4-imino rifamycin S can be used in the preparation of rifamycin derivatives of formula V, as described in U.S. Pat. Nos. 4,219,478, 4,164,499, and 4,226,765; the preparation of rifamycin derivatives of formula XI, as described in U.S. Pat. No. 4,165,317; and the preparation of rifamycin derivatives of formulas VI and X, as described in U.S. Pat. No. 4,305,941. Each of these patents is hereby incorporated by reference.

In 3-halorifamycin S, formula L, halo is a halogen atom (e.g., Br or I). 3-halorifamycin S can be used in the preparation of rifamycin derivatives of formula VII, as described in U.S. Pat. No. 4,341,785 and in the preparation of rifamycin derivatives of formula IV, as described in U.S. Pat. Nos. 4,876,258, 5,003,070 and 4,005,077. Each of these patents is hereby incorporated by reference.

The preparation of rifamycin S is described in U.S. Pat. Nos. 3,884,673 and 3,301,753. Rifamycin S can be used in the preparation of rifamycin derivatives of formulas III and IV, as described by U.S. Pat. Nos. 4,690,919 and 4,876,258, hereby incorporated by reference.

The preparation of rifamycin SV is described in U.S. Pat. Nos. 3,884,673 and 3,301,753. Rifamycin SV can be used to prepare rifamycin derivatives of formula VIII.

The Linker (L)

The linker component (L) of the present invention is, at its simplest, a bond between rifamycin derivative (A) and therapeutic drug (B). More generally, however, the linker provides a molecular skeleton covalently linking (A) and (B). That is, a linear, cyclic, or branched molecular skeleton, with pendant groups which bind covalently with (A) and (B).

Thus, the linking of (A) with (B) is achieved by covalent means, involving bond formation with one or more functional groups located on (A) and (B). Examples of chemically reactive functional groups which may be employed for this purpose include, without limitation, amino, hydroxyl, sulfhydryl, carboxyl, carbonyl, carbohydrate groups, vicinal dials, thioethers, 2-aminoalcohols, 2-aminothiols, guanidinyl, imidazolyl, and phenolic groups.

The covalent linking of (A) with (B) may therefore be effected using a linker (L) which contains reactive moieties capable of reaction with such functional groups present in (A) and (B). The product of this reaction is a linkage group which contains the newly formed bonds linking (L) with (A) and (L) with (B). For example, a hydroxyl group of (A) may react with a carboxylic acid group of (L), or an activated derivative thereof, vide infra, resulting in the formation of an ester linkage group.

Examples of moieties capable of reaction with sulfhydryl groups include α-haloacetyl compounds of the type $XCH_2CO-$ (where X=Br, Cl or I), which show particular reactivity for sulfhydryl groups, but which can also be used to modify imidazolyl, thioether, phenol, and amino groups as described by Gurd, *Methods Enzymol.* 11:532, 1967. N-Maleimide derivatives are also considered selective towards sulfhydryl groups, but may additionally be useful in coupling to amino groups under certain conditions. Reagents such as 2-iminothiolane (Traut et al., *Biochemistry* 12:3266, 1973), which introduce a thiol group through conversion of an amino group, may be considered as sulfhydryl reagents if linking occurs through the formation of disulphide bridges.

Examples of reactive moieties capable of reaction with amino groups include, for example, alkylating and acylating agents. Representative alkylating agents include:

(i) α-haloacetyl compounds, which show specificity towards amino groups in the absence of reactive thiol groups and are of the type $XCH_2CO-$ (where X=Cl, Br or I), for example, as described by Wong *Biochemistry* 24:5337, 1979;

(ii) N-maleimide derivatives, which may react with amino groups either through a Michael type reaction or through acylation by addition to the ring carbonyl group, for example, as described by Smyth et al., *J. Am. Chem. Soc.* 82:4600, 1960 and *Biochem. J.* 91:589, 1964;

(iii) aryl halides such as reactive nitrohaloaromatic compounds;

(iv) alkyl halides, as described, for example, by McKenzie et al., *J. Protein Chem.* 7:581, 1988;

(v) aldehydes and ketones capable of Schiff's base formation with amino groups, the adducts formed usually being stabilized through reduction to give a stable amine;

(vi) epoxide derivatives such as epichlorohydrin and bisoxiranes, which may react with amino, sulfhydryl, or phenolic hydroxyl groups;

(vii) chlorine-containing derivatives of s-triazines, which are very reactive towards nucleophiles such as amino, sufhydryl, and hydroxyl groups;

(viii) aziridines based on s-triazine compounds detailed above, e.g., as described by Ross, *J. Adv. Cancer Res.* 2:1, 1954, which react with nucleophiles such as amino groups by ring opening;

(ix) squaric acid diethyl esters as described by Tietze, *Chem. Ber.* 124:1215, 1991; and (x) α-haloalkyl ethers, which are more reactive alkylating agents than normal alkyl halides because of the activation caused by the ether oxygen atom, as described by Benneche et al., *Eur. J. Med. Chem.* 28:463, 1993.

Representative amino-reactive acylating agents include:

(i) isocyanates and isothiocyanates, particularly aromatic derivatives, which form stable urea and thiourea derivatives respectively;

(ii) sulfonyl chlorides, which have been described by Herzig et al., *Biopolymers* 2:349, 1964;

(iii) acid halides;

(iv) active esters such as nitrophenylesters or N-hydroxysuccinimidyl esters;

(v) acid anhydrides such as mixed, symmetrical, or N-carboxyanhydrides;

(vi) other useful reagents for amide bond formation, for example, as described by M. Bodansky, Principles of Peptide Synthesis, Springer-Verlag, 1984;

(vii) acylazides, e.g. wherein the azide group is generated from a preformed hydrazide derivative using sodium nitrite, as described by Wetz et al., *Anal. Biochem.* 58:347, 1974; and (viii) imidoesters, which form stable amidines on reaction with amino groups, for example, as described by Hunter and Ludwig, *J. Am. Chem. Soc.* 84:3491, 1962.

Aldehydes and ketones may be reacted with amines to form Schiff's bases, which may advantageously be stabilized through reductive amination. Alkoxylamino moieties readily react with ketones and aldehydes to produce stable alkoxamines, for example, as described by Webb et al., in *Bioconjugate Chem.* 1:96, 1990.

Examples of reactive moieties capable of reaction with carboxyl groups include diazo compounds such as diazoacetate esters and diazoacetamides, which react with high specificity to generate ester groups, for example, as described by Herriot, *Adv. Protein Chem.* 3:169, 1947. Carboxylic acid modifying reagents such as carbodiimides, which react through O-acylurea formation followed by amide bond formation, may also be employed.

It will be appreciated that functional groups in the rifamycin derivative (A) and/or the therapeutic drug (B) may, if desired, be converted to other functional groups prior to reaction, for example, to confer additional reactivity or selectivity. Examples of methods useful for this purpose include conversion of amines to carboxylic acids using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxylic acids using reagents such as α-haloacetates; conversion of thiols to amines using reagents such as ethylenimine or 2-bromoethylamine; conversion of carboxylic acids to amines using reagents such as carboduimides followed by diamines; and conversion of alcohols to thiols using reagents such as tosyl chloride followed by transesterification with thioacetate and hydrolysis to the thiol with sodium acetate.

So-called zero-length linkers, involving direct covalent joining of a reactive chemical group of (A) with a reactive chemical group of (B) without introducing additional linking material may, if desired, be used in accordance with the invention. Examples include compounds in which (L) represents a chemical bond linking an oxygen atom of a rifamycin derivative of formula II to a carbonyl or thiocarbonyl moiety present in drug B, such that the linkage group is an ester or thioester. For example, an ester linkage group between (A) and (B) is one possibility for (B) of formulas XXXVI, XXXIX, and XLII.

Most commonly, however, the linker will include two or more reactive moieties, as described above, connected by a spacer element. The presence of such a spacer permits bifunctional linkers to react with specific functional groups within (A) and (B), resulting in a covalent linkage between these two compounds. The reactive moieties in a linker (L) may be the same (homobifunctional linker) or different (heterobifunctional linker, or, where several dissimilar reactive moieties are present, heteromultifunctional linker), providing a diversity of potential reagents that may bring about covalent attachment between (A) and (B).

Spacer elements typically consist of chains which effectively separate (A) and (B) by a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, or $-(CH_2CH_2O)_nCH_2CH_2-$, in which n is 1 to 4.

The nature of extrinsic material introduced by the linking agent may have a critical bearing on the pharmacokinetics and/or activity of the ultimate product. Thus it may be desirable to introduce cleavable linkers, containing spacer arms which are biodegradable or chemically sensitive or which incorporate enzymatic cleavage sites.

Linkers may form linkage groups with biodegradable diester, diamide, or dicarbamate groups of formula XXI:

XXI

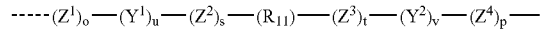

where, each of $Z^1$, $Z^2$, $Z^3$, and $Z^4$ is independently selected from O, S, and $NR_{12}$ (where $R_{12}$ is hydrogen or an alkyl group); each of $Y^1$ and $Y^2$ is independently selected from a carbonyl, thiocarbonyl, sulphonyl, phosphoryl or similar acid-forming group; o, p, s, t, u, and v are each independently 0 or 1; and $R_{11}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, $-(CH_2CH_2O)_qCH_2CH_2-$ in which q is 1 to 4, or a chemical bond linking $-(Z^1)_o-(Y^1)_u-(Z^2)_s-$ to $-(Z^3)_t-(Y^2)_v-(Z^4)_p-$.

Linkers designed to form hydrazone linkages have the chemical formula XXV:

XXV

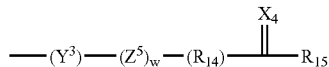

wherein $Z^5$ is selected from O, S, or $NR_{16}$; $R_{16}$ is hydrogen or an alkyl group; $R_{15}$ is selected from hydrogen, an alkyl, or a heteroalkyl; $Y^3$ is selected from a carbonyl, thiocarbonyl, sulphonyl, phosphoryl, or a similar acid-forming group covalently bound to an oxygen atom of rifamycin derivative (A); w is 0 or 1; $R_{14}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, $-(CH_2CH_2O)_nCH_2CH_2-$, in which n is 1 to 4, or a chemical bond linking $-(Y^3)-(Z^5)_w-$ to

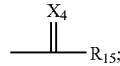

and $X_4$ is a hydrazone resulting from the condensation reaction of a drug B containing a hydrazide group and the precursor to linker XXV, in which $X_4$ is the oxygen atom of a ketone or aldehyde.

These cleavable linkers, as discussed in PCT Publication WO 92/17436 (hereby incorporated by reference), are readily biodegraded in vivo. In some cases, linkage groups are cleaved in the presence of esterases, but are stable in the absence of such enzymes. (A) and (B) may, therefore, advantageously be linked to permit their slow release by enzymes active near the site of disease.

Linkage groups are formed from reactive functional groups contained in (A) and/or (B). Reactive functional groups from (A) and/or (B) are selected from but not limited to carboxyl, aldehyde, amine (NHR), alcohols, hydrazide, and sulfhydryl groups.

Additionally, a group within (A) and/or (B) may readily be modified into a reactive group, such as those mentioned above. For example, an aldehyde may be oxidized to a carboxylic acid, in which case the "linkage group" can be derived from reactive groups selected from, for example, amino, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxyl, carboxy, carboxyalkyl, and carboxyaryl groups.

Therapeutic Drug (B)

(B) of formula I is any therapeutic drug or an active metabolite thereof. Representative and non-limiting examples of drugs useful in accordance with the invention include: antifungal agents such as ketoconazole, nystatin, griseofulvin, flucytosine, miconazole or amphotericin B; antituberculars such as p-aminosalicylic acid, isoniazid, capreomycin sulfate, cyclosexine, ethambutol, ethionamide, pyrazinamide, rifampin, or streptomycin sulphate; antivirals such as acyclovir, amantadine, azidothymidine, ribavirin or vidarabine; antibiotics such as azithromycin, dapsone, chloramphenicol, neomycin, cefaclor, cefadroxil, cephalexin, cephradine, erythromycin, clindamycin, lincomycin, amoxicillin, ampicillin, bacampicillin, carbenicillin, dicloxacillin, cyclacillin, picloxacillin, hetacillin, methicillin, nafcillin, penicillin, polymyxin, pyrazinamide, or tetracycline; antiinflammatories such as celecoxib, refecocoxib, diflunisal, ibuprofen, indomethacin, meclefenamate, mefenamic acid, naproxen, phenylbutazone, piroxicam, tolmetin, aspirin or salicylates; antiprotozoans such as chloroquine, metronidazole, quinine or meglumine antimonate; and pharmaceutically acceptable salts (e.g., acid addition salts such as the hydrochloride or hydrobromide or base salts such as sodium, calcium, or magnesium salts) or derivatives (e.g. acetates) thereof.

Additional therapeutic drugs and active metabolites of the invention are provided in FIG. 2. These include isoniazid, ethambutol, azithromycin, pyrazinamide, p-aminosalicylic acid, ethionamide, cycloserine, 4-pyridinemethanol, 2-ethyl-4-pyridinemethanol, isonicotinic acid, and 2-ethylisonicotinic acid.

Therapeutic drugs that can be used in the present invention include pyrazinamide such as those disclosed in U.S. Pat. Nos. 6,399,607, 5,643,912, 4,962,111, and 3,108,099, hereby incorporated by reference.

Compounds of Formula I

Some compounds of formula I will exhibit therapeutic activity in their conjugated form. That is, hydrolysis of the linker is not required for the compound to provide a beneficial therapeutic effect.

For cleavable conjugates, the attachment of (A) and (B) to linker (L) may be through an enzymatically degradable ester linkage. Therapeutic drugs suitable for use in this embodiment include any known therapeutic drug (B), or active analogues thereof, containing hydroxyl or carboxyl groups. These may be coupled to a linker containing a carboxyl or hydroxyl group through the formation of an ester linkage.

In some cases, it is expected that the conjugate will be therapeutically inactive, or exhibit reduced activity. In these cases, the drug will be activated by the in vivo cleavage of the linker. This is illustrated in FIG. 1, where the active form of the drug, pyrazinoic acid, is released with cleavage of the conjugate. Thus, the activity of the pyrazinoic acid is restored upon cleavage of the conjugate.

Pyrazinamide, PZA, is an important front-line tuberculosis (TB) drug, which can shorten TB therapy because of its activity against a population of semi-dormant organisms that are not affected by other TB drugs. It has been recognized since the 1950s that PZA has anti-tuberculosis activity at acid pH but not at neutral pH. It is also known that the role of acid pH is to enhance the uptake and accumulation of pyrazinoic acid (POA), the active form of PZA in the tubercle bacilli (Zhang et al., *J. Bacteriol.* 181:2044, 1999). The mechanism of TB resistance to PZA has been known since the 1960's. PZA-resistant TB strains lose pyrazinamidase and nicotinamidase enzyme activity (Scorpio et al., *Nat. Med.* 2:662, 1996; Scorpio et al., *Antimicrob. Agents Chemother.* 41:540, 1997). As a result, PZA accumulating in these resistant strains is not converted to the active (POA) form of the drug. Because PZA conjugates of the present invention do not rely upon intracellular pyrazinamidase and nicotinamidase enzyme activity for their activation, they are expected to circumvent the mechanism of resistance in PZA-resistant TB strains.

Drug (B) may also be selected from an in vivo activated metabolite. For example, ethionamide is an important component of second-line therapy for the treatment of multi-drug-resistant tuberculosis. An examination of drug metabolites formed by whole cells of *Mycobacterium tuberculosis* have shown that ETA is activated by S-oxidation before interacting with its cellular target (see DeBarber et al., *Proc. Natl. Acad. Sci. USA* 97:9677, 2000). ETA is metabolized by *Mycobacterium tuberculosis* to a 2-ethyl 4-pyridinemethanol by the catalase-peroxidase KatG. Ethionamide resistance is conferred to TB strains lacking catalase-peroxidase activity. A similar phenomenon has been observed for isoniazid, which is metabolized to the structurally similar 4-pyridinemethanol. Thus, a conjugate of formula I in which (B) is taken from the active metabolite rather than the parent drug, will allow these agents, in some instances, to be effective therapeutics in the treatment of bacteria resistant to the parent drug.

When therapeutic drug (B) is an anti-inflammatory agent, a statin, an antibacterial agent, a platelet aggregation inhibitor, a blood thinning agent, or a lipid lower agent, the resulting (A)—(L)—(B) conjugate is useful for treating or preventing the development of an atherosclerosis-associated disease. The conjugate, when administered to a patient suffering from atherosclerosis-associated disease, lowers the level of C-reactive protein in the patient.

Drug-rifamycin derivative conjugates, compounds of formula I, can be synthesized, for example, as described in Examples 1–18. Methods useful in the synthesis of compounds of formula I are described in the literature and are familiar to those skilled in the art.

Assays

Compounds of the invention can be assayed by using standard in vitro models or animal models to evaluate therapeutic activity of therapeutic drug (B), and active derivatives thereof. These assays are presently described in the literature and are familiar to those skilled in the art. These include but are not limited to assays for monitoring inflammation, microbial infection, and autoimmune diseases (e.g., atherosclerosis, MS, rheumatoid arthritis).

Inflammation, for example, is regulated by a large number of pro- and anti-inflammatory mediators, which include cytokines, eicosanoids, nitric oxide, and reactive oxygen species. Inflammation can be treated with relatively non-selective anti-inflammatory agents, such as corticosteroids and various non-steroidal anti-inflammatory drugs. More recently, drugs have been developed that specifically interfere with the action of selected pro-inflammatory mediators, such as TNFα and PGE2. Depending upon the identity of therapeutic drug (B), assays of inflammatory mediators and the activation state of inflammatory cells may include analysis of a wide variety of molecules known to be involved in inflammation (e.g., cytokines, metalloproteinases, heat shock proteins, cAMP, iNOS, and/or COX-2).

Compounds of the present invention can be screened for antimicrobial activity by measuring their minimum inhibitory concentration (MIC), using standard MIC in vitro assays (see, for example, Tomioka et al., *Antimicrob. Agents Chemother.* 37:67, 1993). Agents can be screened against *Chlamydophila pneumoniae, Chlamydia trachomatis, Mycobacterium tuberculosis* (including multiple drug resistant strains), *Mycobacterium avium* complex, and other intracellular infectious bacteria. Details of a standard MJC assay are provided in Example 18.

In addition, compounds can be evaluated using standard in vivo animal models of infection and autoimmune disease (e.g., atherosclerosis, MS, rheumatoid arthritis).

Therapy

The invention features a method of treating or preventing a disease or condition associated with a microbial infection by administering a compound of formula I, XX, or XXVI–XXXV. Compounds of the present invention may be administered by any appropriate route for treatment or prevention of a disease or condition associated with a microbial infection, inflammation, or infection derived autoimmune disease, among others. These may be administered to humans, domestic pets, livestock, or other animals with a pharmaceutically acceptable diluent, carrier, or excipient, in unit dosage form. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Formulations for intravenous administration can be prepared as described in U.S. Ser. No. 60/385,532, hereby incorporated by reference.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro A R., 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastrointestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Pharmaceutical formulations of compounds of formulas I, XX, or XXVI–XXXV of the invention described herein includes isomers such as diastereomers and enantiomers, mixtures of isomers, including racemic mixtures, salts, solvates, and polymorphs thereof.

The formulations can be administered to human patients in therapeutically effective amounts. For example, when B is an antimicrobial drug, an amount is administered which prevents, stabilizes, eliminates, or reduces a microbial infection. Typical dose ranges are from about 0.01 μg/kg to about 2 mg/kg of body weight per day. The exemplary dosage of drug to be administered is likely to depend on such variables as the type and extent of the disorder, the overall health status of the particular patient, the formulation of the compound excipients, and its route of administration. Standard clinical trials maybe used to optimize the dose and dosing frequency for any particular compound.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Protection and Deprotection of Reactive Groups (A)—(L)—(B) compounds can be prepared by selective protection and deprotection of alcohols, amines, sulfhydryls and carboxylic acid functional groups of rifamycin derivative (A), linker (L), and drug (B). For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxylic acids include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. An acetal can be used to protect the 21-hydroxy and 23-hydroxy positions of a rifamycin compound, as described in U.S. Pat. No. 5,786,350, hereby incorporated by reference. The general structure is provided below, wherein ring G is defined as in formula II.

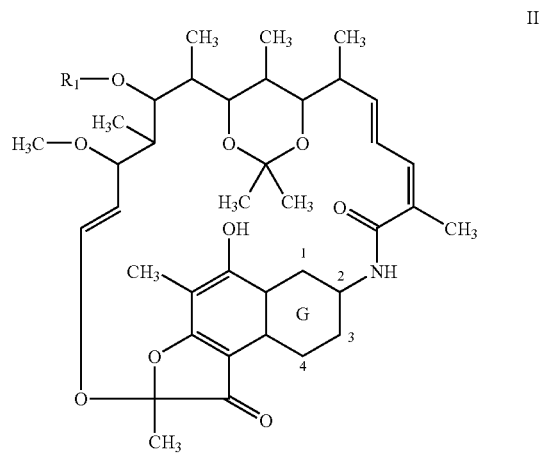

Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, sulfhydryl, and carboxylic acid functionalities and the conditions required for their removal are provided in detail in "T. W. Green and P. G. M. Wuts: Protective Groups in Organic Synthesis" ($2^{nd}$ ed., 1991, John Wiley & Sons) and "P. J. Kocienski: Protecting Groups" (1994 Georg Thieme Verlag); each of which is hereby incorporated by reference.

In the examples that follow, the use of protecting groups is indicated in a structure by the letter P, where P for any amine, aldehyde, carboxylic acid, sulfhydryl, or alcohol may be any of the protecting groups listed above.

EXAMPLE 2

Synthesis of 30-hydroxy and 32-hydroxy Precursor (A) Compounds

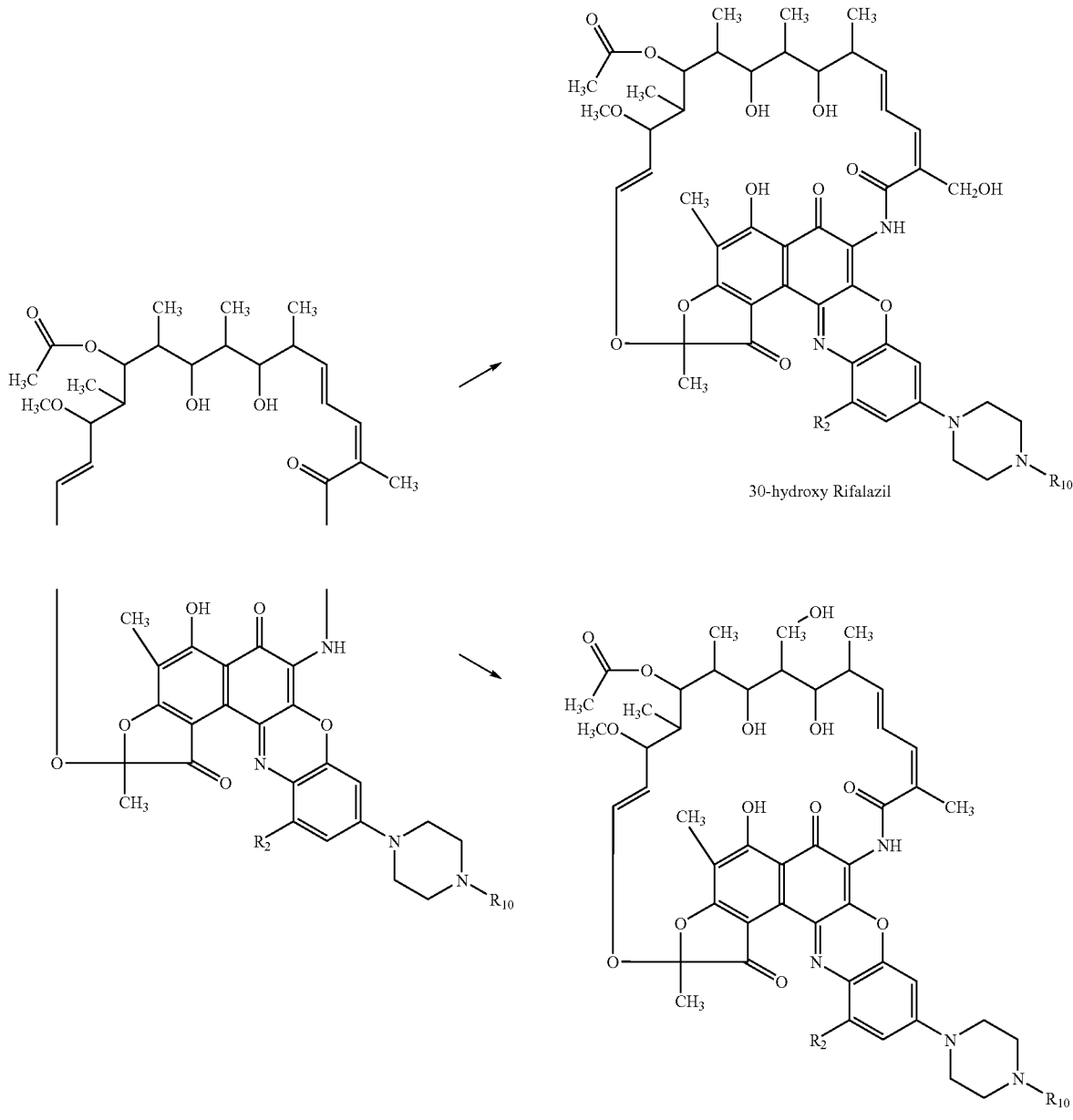

The selective oxidation of the 30 and 32 positions of Rifalazil from H to OH is shown in reaction scheme 1. This transformation can be achieved by enzymatic oxidation using the P450 enzyme CYP3A4 (Research Diagnostics, Inc., product number RDI-CYP3A4). Either the commercially available enzyme can be used or rifamycin derivatives can be incubated in liver microsomes as described in Mae et al., *Xenobiotica*, 30:565, 2000. When the latter method is used, inhibitors of B-esterase, such as diisopropylfluorophosphate, diethyl p-nitrophenylphosphate, or eserine, can be added to prevent enzymatic deacetylation of the rifamycin derivative. 30-Hydroxy Rifalizil and 32-hydroxy Rifalazil can be separated using the hplc techniques described in Mae et al., *Xenobiotica*, 30(6):565, 2000.

Selective protection of the primary alcohol produced by the enzymatic oxidation of (A) as shown in reaction scheme 1, can be accomplished using trityl, tert-butyldimethylsilyl, or tert-butyldiphenyl silyl protecting groups, which are selective for primary alcohols under controlled conditions (see, *J. Am. Chem. Soc.* 84:430, 1962, *J. Am. Chem. Soc.* 94:6190, 1972, and *Tet. Lett.*, 30:19, 1989). This is followed by the protection of the other hydroxyl groups of (A) using a non-silyl protecting group (Example 1) and the removal of the silyl protecting group at the primary alcohol by addition of tetrabutyl ammonium fluoride. The resulting compound has the formula LIII or LIV, where $R_{10}$ and $R_2$ are defined as in formula XX. In examples where $R_2$ is hydroxyl or sulfhydryl this group is also protected.

Alternatively, all of the alcohols may be protected using silyl protecting groups. The primary alcohol can then be preferentially deprotected using mild conditions. The resulting compound has the formula LIII or LIV.

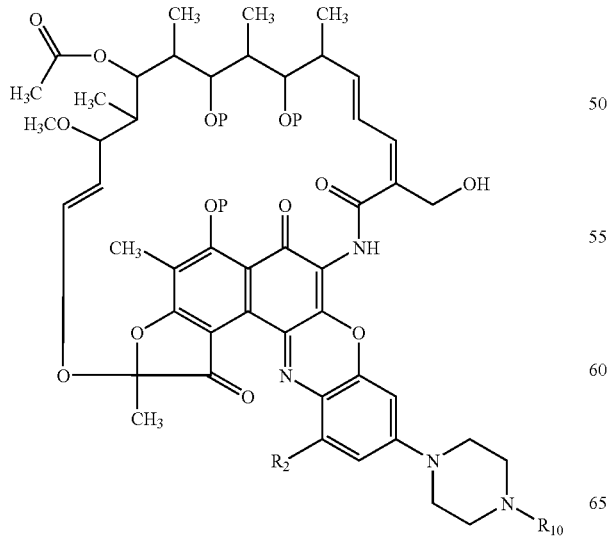

LIII

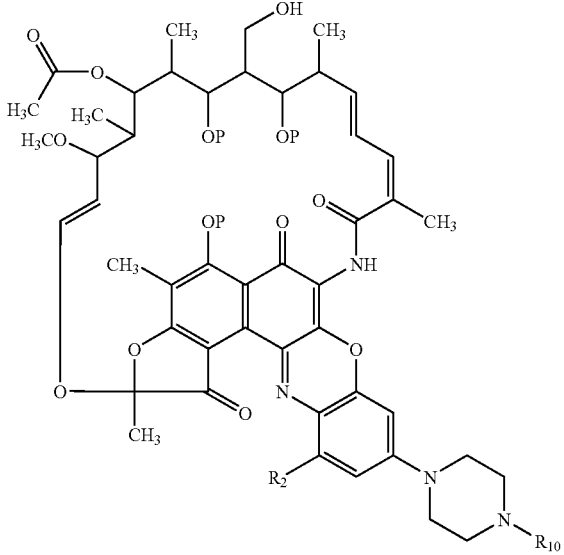

LIV

EXAMPLE 3

Synthesis of 36-deacetylated Precursor (A) Compounds reaction scheme 2

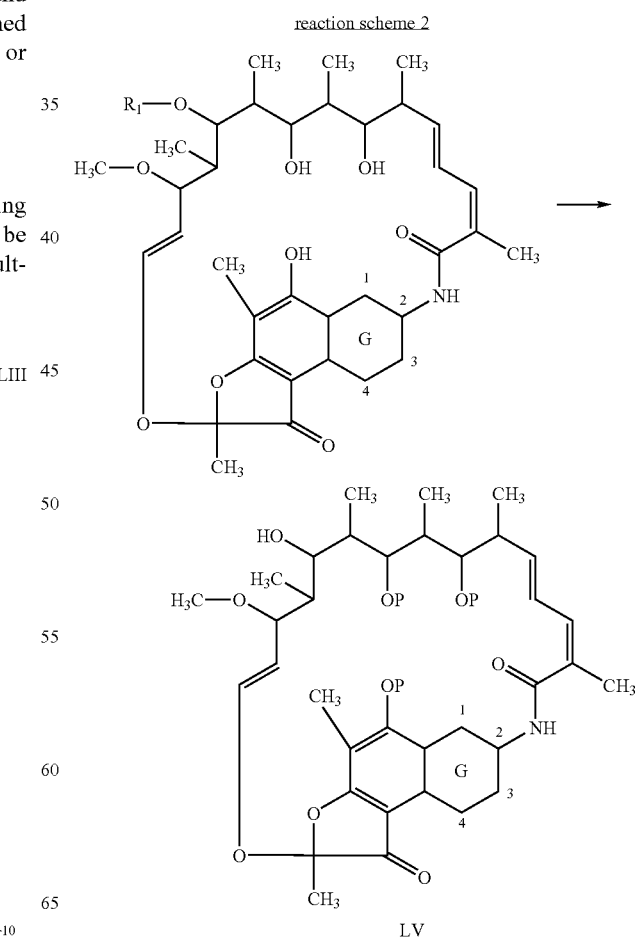

LV

The deacetylation of (A), where $R_1$ is converted from acetyl to H is shown in reaction scheme 2. The hydroxyls of (A) can be protected as described in Example 1. Protecting groups are chosen that are not removed during the deacetylation step, such as methoxymethyl ethers, methoxyethoxymethyl ethers, benzyloxymethyl ethers, or any other protecting group compatible with strong bases or nucleophiles. After protection of the hydroxyl groups, the acetyl group can be removed under any one of several conditions known in the art including: KCN/EtOH/reflux, $K_2CO_3$/MeOH/reflux, $NH_3$/MeOH, LiOH/THF/$H_2O$, or enzymatic hydrolysis (e.g., lipase). A method for deacetylating rifamycin S is disclosed by U.S. Pat. No. 4,188,321, hereby incorporated by reference. Hydroxy protected 36-deacetylated rifamycin derivatives have the formula LV, wherein ring G is defined as in formula II.

EXAMPLE 4

Synthesis of 36-α($X_5$)-acetyl Rifamycin Derivatives

It is also possible to replace the acetyl group at position 36 with a chemically reactive group using the synthetic methods disclosed in U.S. Pat. No. 5,786,350, hereby incorporated by reference. Compounds prepared by this method are described by formula LVI, wherein ring G has one of formulas III–VIII, X, or XI and $X_5$ is selected from hydroxyl, sulfhydryl, bromine, or iodine.

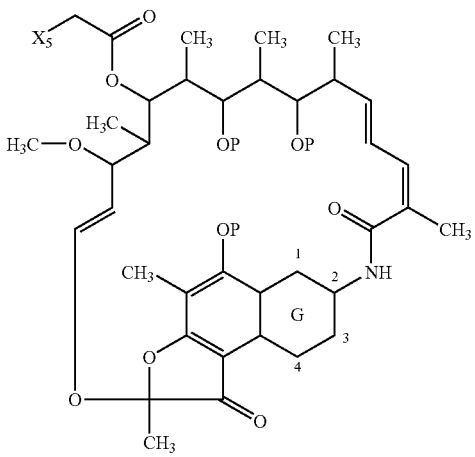

LVI $X_5$ can be covalently attached directly to therapeutic drug (B) or to —(L)—(B). For example, when $X_5$ is hydroxyl an ester linkage group can be formed between $X_5$ and a carboxylic acid group of drug (B).

Starting materials of formula LVI wherein ring G is described by formula IX must be prepared from a 3-formyl rifamycin derivative of formula LVII, wherein the aldehyde is protected as a cyclic acetal. A compound of formula LVII is conjugated to linker and drug B followed by deprotection of the alcohols and aldehyde to produce the 3-formyl rifamycin of formula LVIII, wherein (B), L, and $X_5$ are defined as described above.

Compounds of formula LVIII are readily converted to rifamycin derivatives of formula IX using methods described in U.S. Pat. Nos. 3,342,810, 4,551,450, 4,681,938, each of which is hereby incorporated by reference.

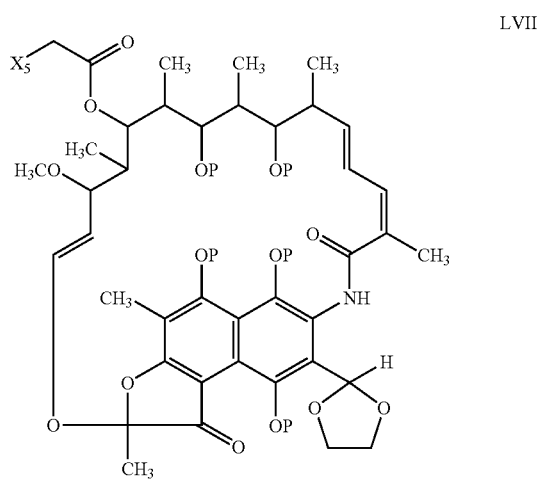

LVII

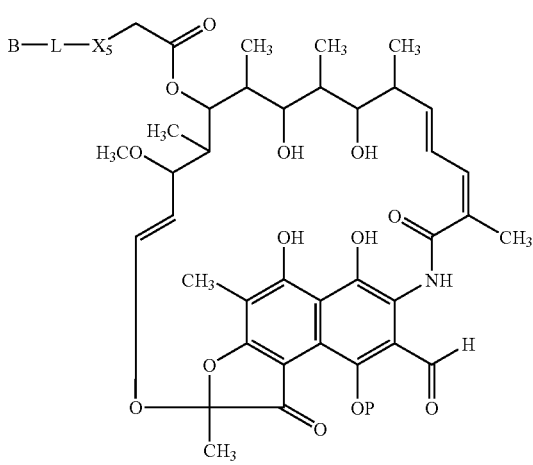

LVIII

The methods described in Example 4 can be used to synthesize (A)—(L)—(B) conjugates of formulas XXVII–XXXI, and XXXIV.

EXAMPLE 5

Synthesis of Isoniazid Conjugates

Isoniazid conjugates of formulas XXVIII–XXXV can be prepared using intermediates LIII–LVI. First, isoniazid (Aldrich, catalogue number 1-1,753-2) is condensed with a linker of formula XXV, as shown in reaction scheme 3, using pyruvic acid (Aldrich, catalogue number 10,736-0). The conversion of aldehydes and ketones to hydrazones can be accomplished as described by, for example, J. March, Advanced Organic Chemistry: Reactions, Mechanisms and Structure, John Wiley & Sons, Inc. pp. 904–905, 1992. The hydrazone is formed with the reaction scheme 3

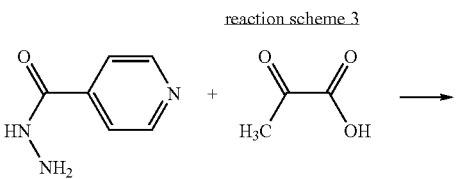

-continued

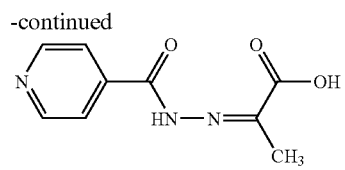

acid portion of the linker undisturbed. The carboxylic acid can be activated, for example, by formation of an active ester, such as nitrophenylesters, N-hydroxysuccinimidyl esters, or others as described in *Chem. Soc. Rev.* 12:129, 1983 and *Angew. Chem. Int. Ed. Engl.* 17:569, 1978 (hereby incorporated by reference). The activated acid can then be reacted with a compound of formulas LIII–LVI, resulting in the formation of an ester linkage. In the example shown below, a compound of formula XXa (see FIG. 3) is conjugated to isoniazid. The product of reaction scheme 4 undergoes deprotection of the hydroxyl protecting reaction scheme 4

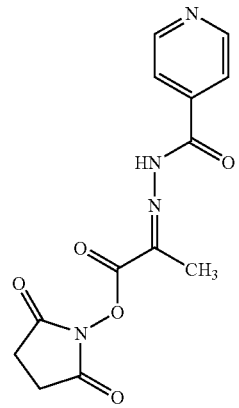

+

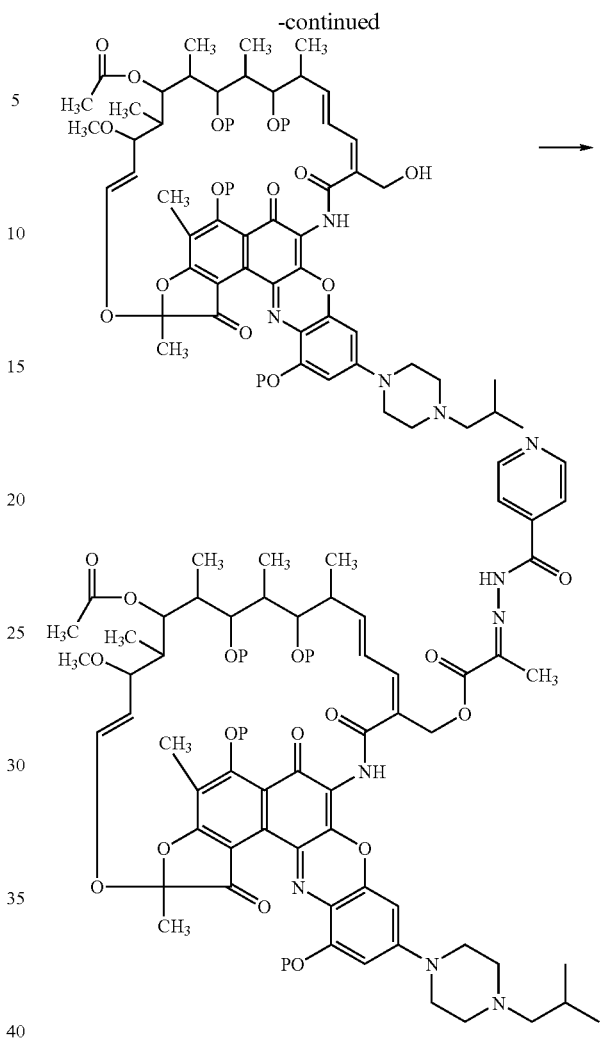

groups to yield the desired product. For the reactions involving compounds of formula LIII or LV (see FIG. 3), the resulting products are shown below.

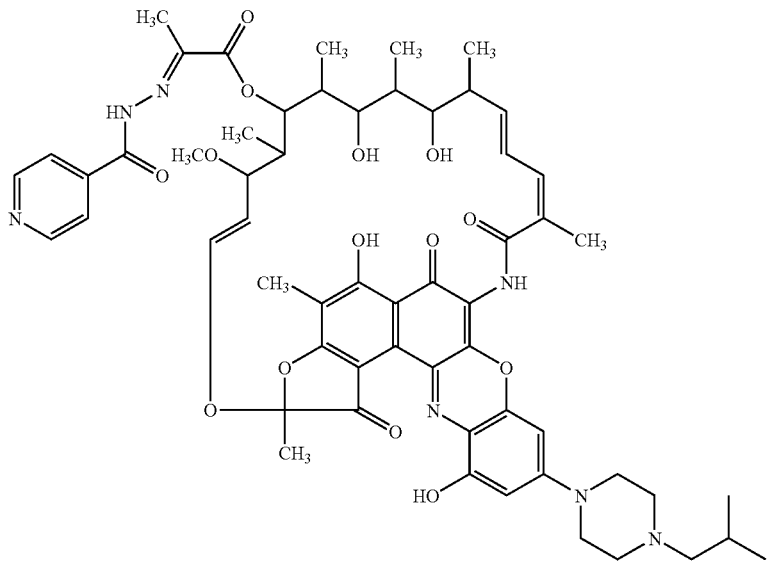

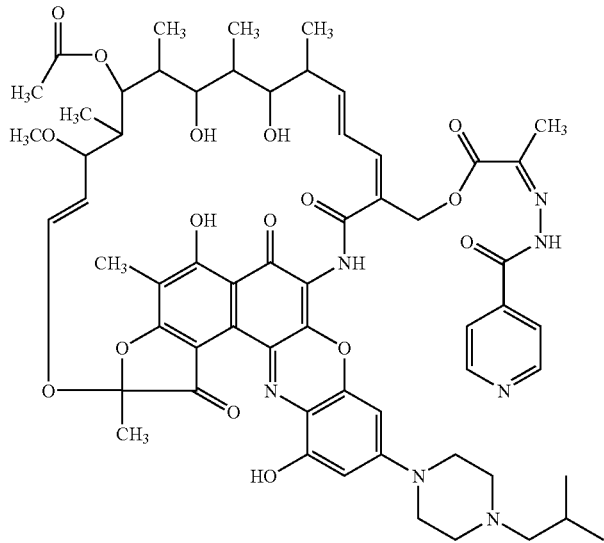

This approach may be adapted to any ketone-acid or aldehyde-acid linker of formula XXV. The methods described in Example 5 can be used to synthesize isoniazid conjugates of formulas XXVIII–XXXV.

EXAMPLE 6

Synthesis of PZA Conjugates

The acid of 2-pyrazinecarboxylic acid (Aldrich, catalogue number P5,610-0) can be activated, vide supra, and reacted with the free hydroxyl group of intermediate of formulas LIII–LVI. This can be followed by removal of the hydroxyl protecting groups. Products of reactions involving compounds of formula XXa (see FIG. 3) are shown below.

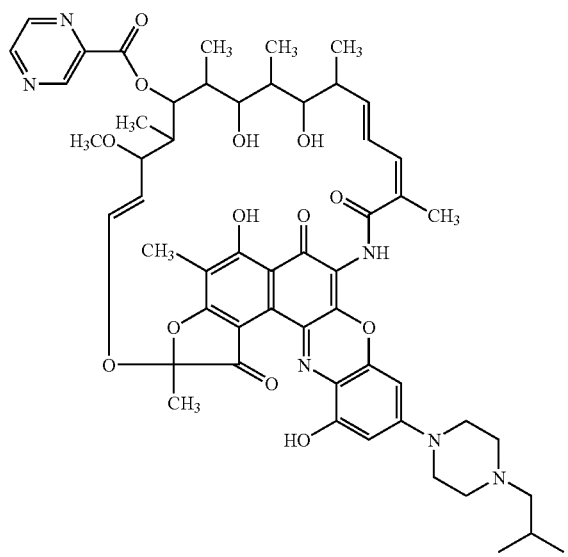

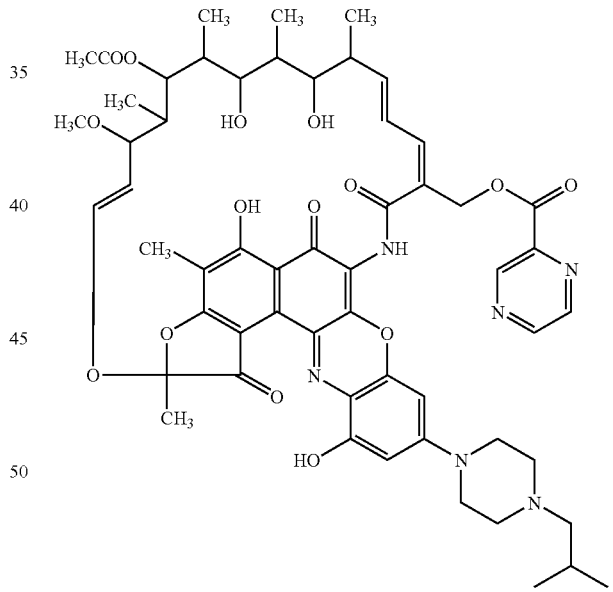

PZA conjugates of formula XXVII–XXXV, where the linker (L) is not a zero-length linker, are prepared in a similar manner. First, 2-pyrazinecarboxylic acid can be activated, vide supra, and reacted with glycolic acid (Aldrich, catalogue number 12,473-7), which has been protected at the carboxylic acid group, see Example 1, as shown in reaction scheme 5. Subsequently, the product of

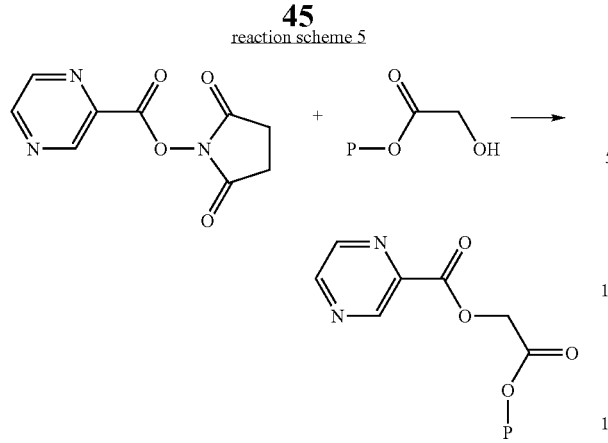

reaction scheme 5 can be deprotected, followed by activation of the carboxylic acid and reaction with an intermediate of formulas LIII–LVI. Further removal of the hydroxyl protecting groups produces conjugates of formula I. For reactions involving compounds of formula XXa (see FIG. 3), the resulting products are shown below.

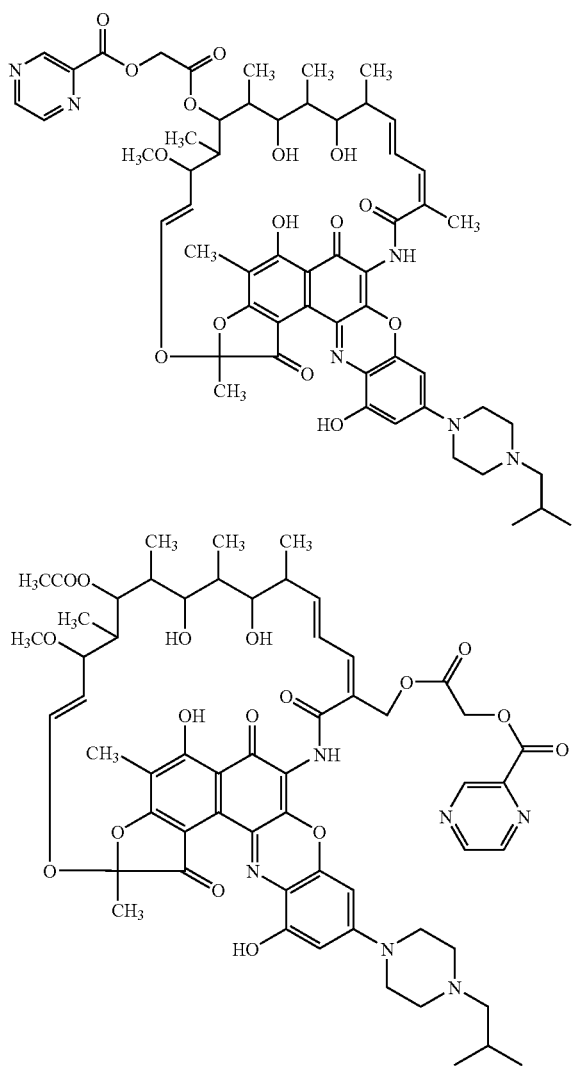

The foregoing approach may be adapted to any alcohol-acid linker of formula XXI. The methods described in Example 6 can be used to synthesize 2-pyrazinecarboxylic acid conjugates of formulas XXVIII–XXXV.

EXAMPLE 7

Synthesis of Ethambutol Conjugates

The reactive functionalities of ethambutol (HCl salt, Fragchem, product number 4) can be protected as shown in reaction scheme 6. The free alcohol of the ethambutol derivative can be reacted with the monoprotected activated acid, vide supra, of oxalic acid (Aldrich, catalogue number 24,117-2).

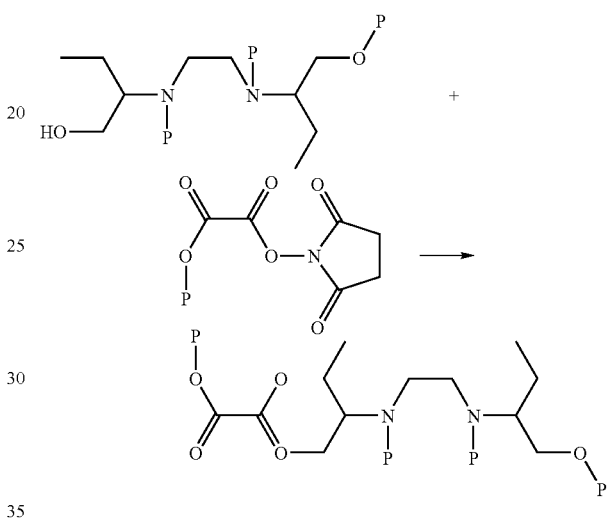

Subsequently, the acid protecting group in the product of reaction scheme 6 can be deprotected, followed by activation of the carboxylic acid and reaction with intermediate of formulas LIII–LVI. Removal of the hydroxyl and amine protecting groups, produces ethambutol conjugates of formulas XXVIII–XXXV. For reactions involving compounds of formula XXa (see FIG. 3), the resulting products are shown below.

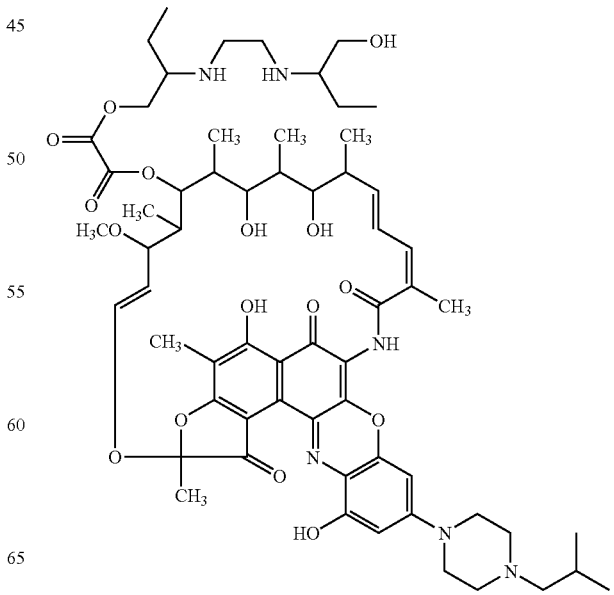

-continued

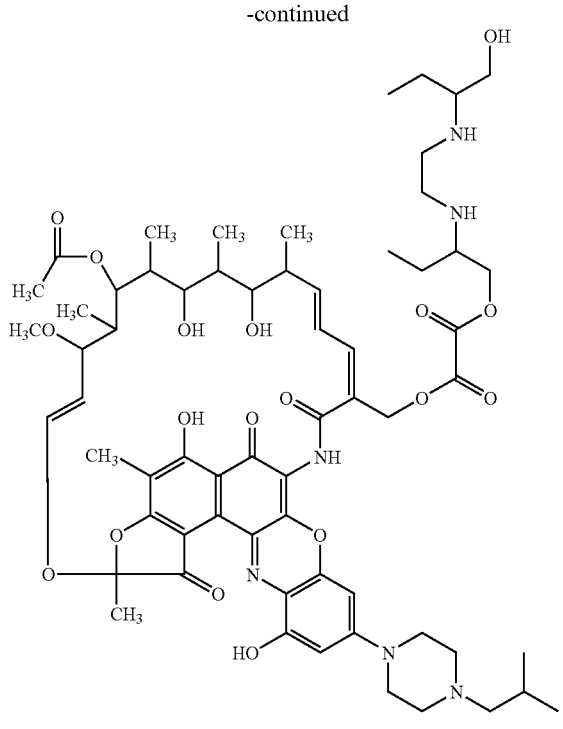

This approach may be adapted to any di-acid linker of formula XXIII. The methods described in Example 7 can be used to synthesize ethambutol conjugates of formulas XXVIII–XXXV.

EXAMPLE 8

Synthesis of Cycloserine Conjugates

The amine of cycloserine (R or S stereochemistry, Aldrich, catalogue numbers 85,857-9 and 86,199-5) can be reacted with the monoprotected activated acid of oxalic acid, vide supra, as shown in reaction scheme 7.

reaction scheme 7

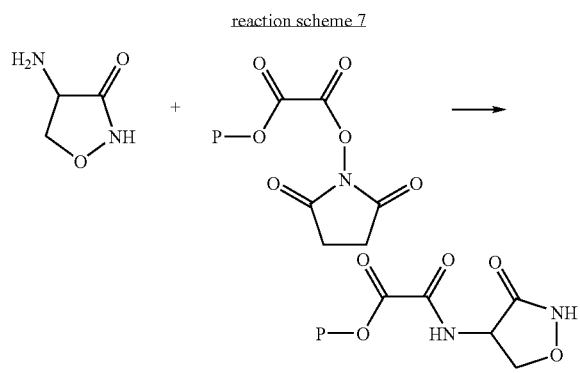

Subsequently, the acid protecting group in the product of reaction scheme 7 can be deprotected, followed by activation of the carboxylic acid and reaction with an intermediate of formulas LIII–LVI. Removal of the hydroxyl protecting groups produces cycloserine conjugates of formulas XXVII-I–XXXV. For reactions involving compounds of formula XXa (see FIG. 3), the resulting products are shown below.

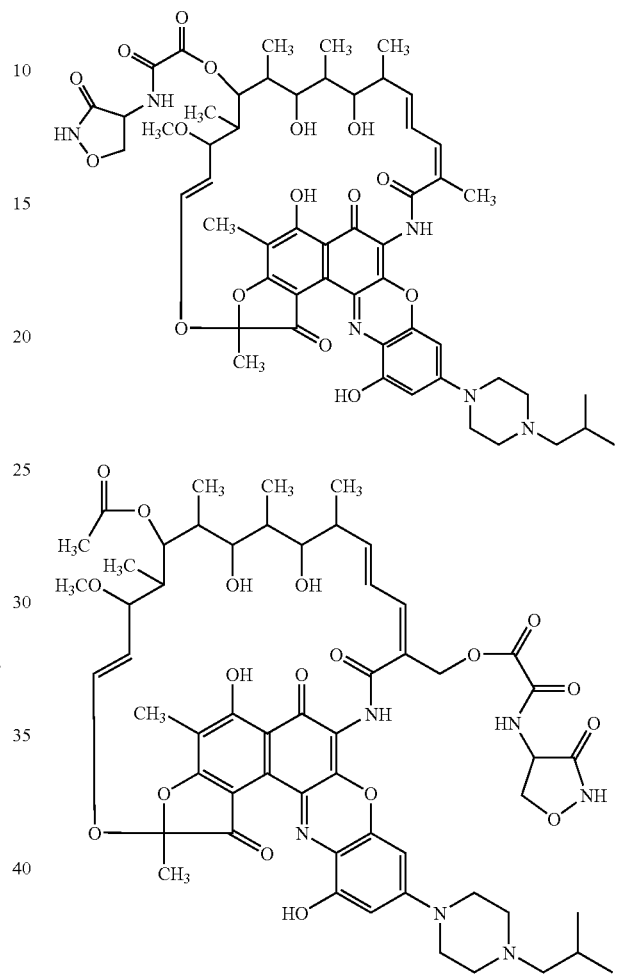

This approach may be adapted to any di-acid linker of formula XXIII.

Compounds of formulas XXVIII–XXXV in which cycloserine attaches to the linker via a carbamate linkage can be prepared in a similar manner. First, monoprotected glycolic acid is condensed with a bifunctional carbonic acid such as phosgene or carbonyl duimidazole to form a diester carbonate as shown in reaction scheme 8. The diester carbonate is then condensed with cycloserine to form the carbamate linkage as shown in reaction scheme 9.

reaction scheme 8

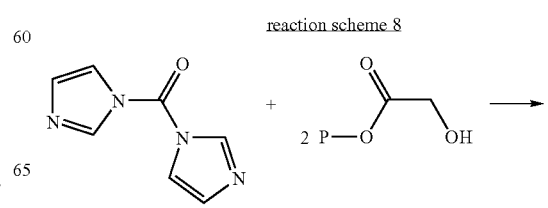

-continued

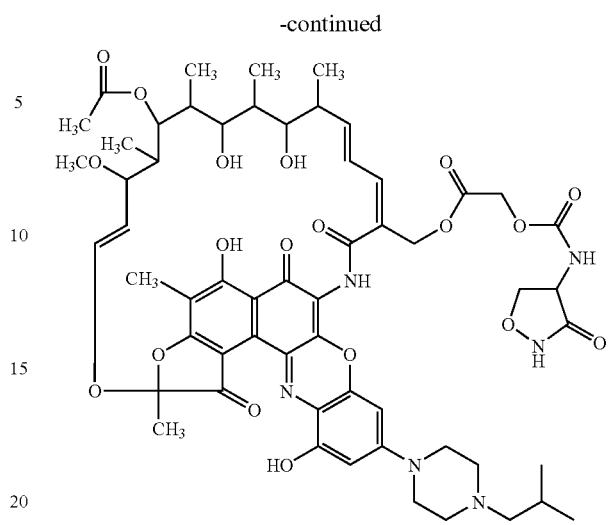

reaction scheme 9

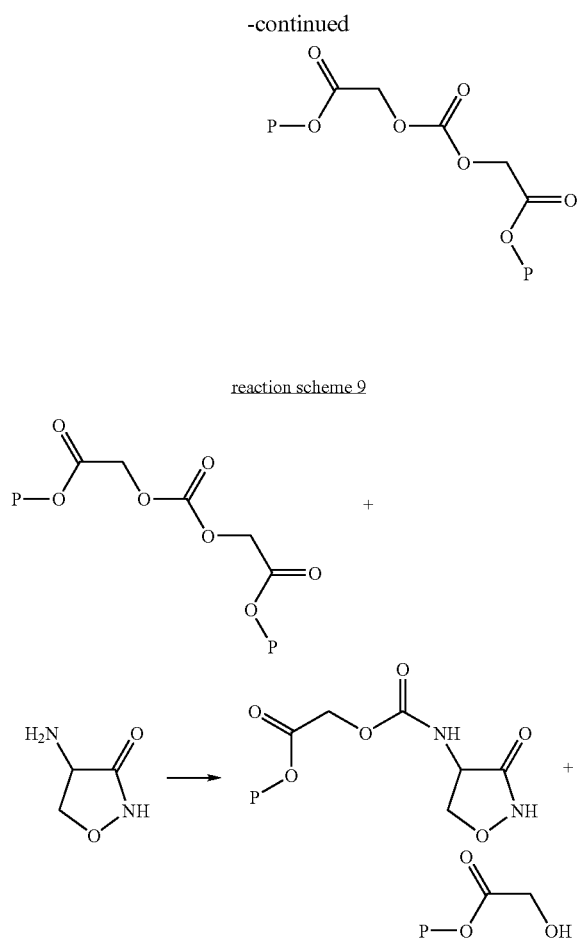

Subsequently, the acid protecting group of the cycloserine carbamate glycolic acid conjugate product of reaction scheme 9 can be deprotected, followed by activation of the carboxylic acid, reaction with an intermediate of formulas LIII–LVI, and removal of the remaining protecting groups. For reactions involving compounds of formula XXa (see FIG. 3), the resulting products are shown below.

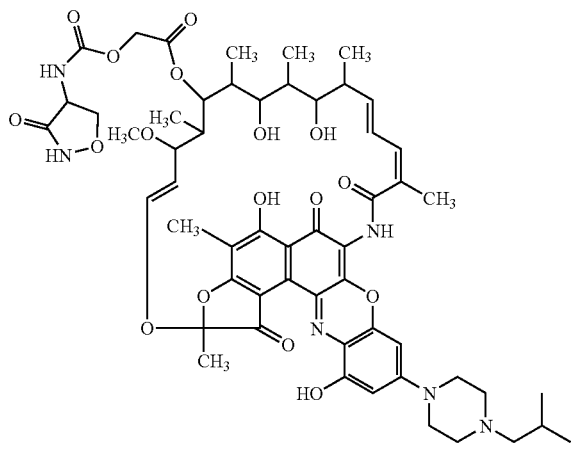

This approach may be adapted to any alcohol-acid linker of formula XXI. The methods described in Example 8 can be used to synthesize cycloserine conjugates of formulas XXVIII–XXXV.

EXAMPLE 9

Synthesis of 4-Pyridinemethanol Conjugates

Using a method analogous to that of Example 7, the alcohol of 4-pyridinemethanol (Aldrich, catalogue number 15,162-9 ) can be reacted with the monoprotected activated acid of oxalic acid, as shown in reaction scheme 10.

reaction scheme 10

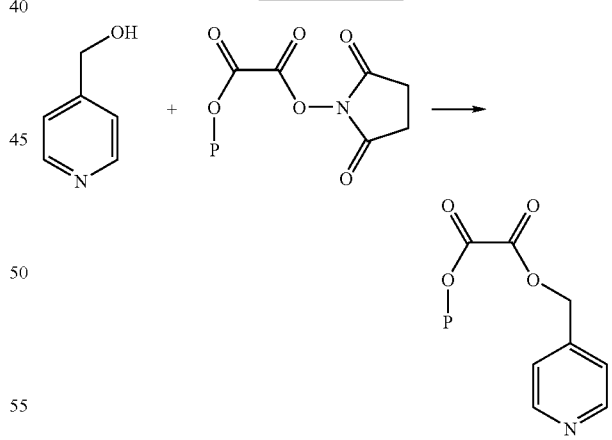

Subsequently, the acid protecting group in the product of reaction scheme 10 can be deprotected, followed by activation of the carboxylic acid and reaction with an intermediate of formulas LIII–LVI. Removal of the hydroxyl protecting groups, produces 4-pyridinemethanol conjugates of formulas XXVIII–XXXV. For reactions involving compounds of formula XXa (see FIG. 3), the resulting products are shown below.

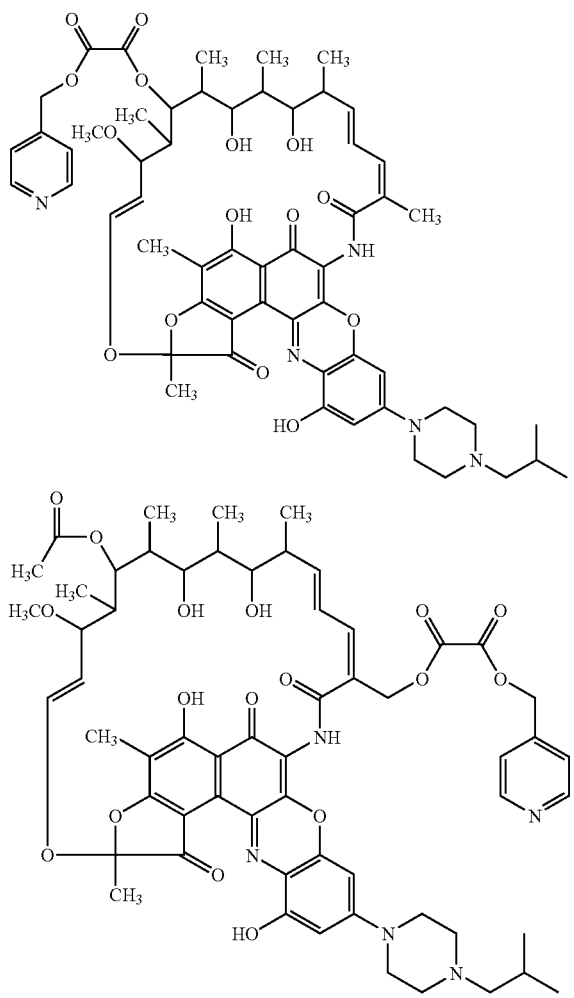

This approach may be adapted to any di-acid linker of formula XXIII. The methods described in Example 9 can be used to synthesize 4-pyridinemethanol conjugates of formulas XXVIII–XXXV.

EXAMPLE 10

Synthesis of 2-Ethyl-4-Pyridinemethanol Conjugates

Ethionamide (H&S Chemical Company, Inc., catalog number 001583) can be hydrolyzed under acidic conditions to produce 2-ethyl-4-pyridinecarboxylic acid, which can be subsequently reduced to an alcohol as shown in reaction scheme 11.

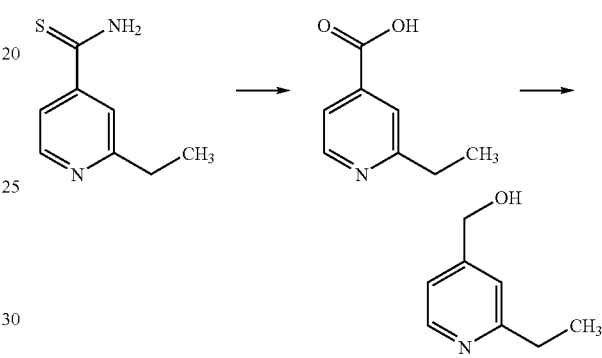

The reduction of the acid to the alcohol may be accomplished using $LiAlH_4$ or another suitable reducing agent, see "Gaylord: Reduction with Complex Metal Hydrides" (1956, pp. 322–373, Wiley).

2-Ethyl-4-pyridinemethanol conjugates can be prepared according to the method described in Example 9. The reaction produces compounds of formulas XXVIII–XXXV. For reactions involving compounds of formula XXa (see FIG. 3), the resulting products are shown below.

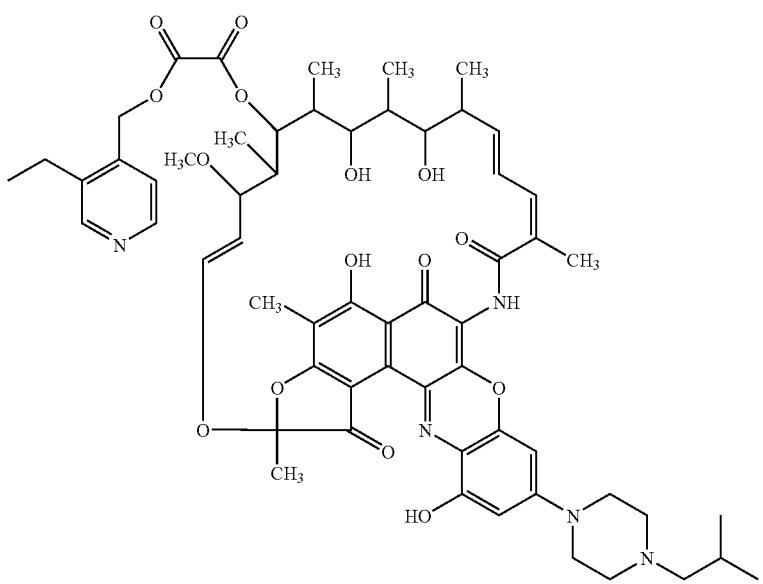

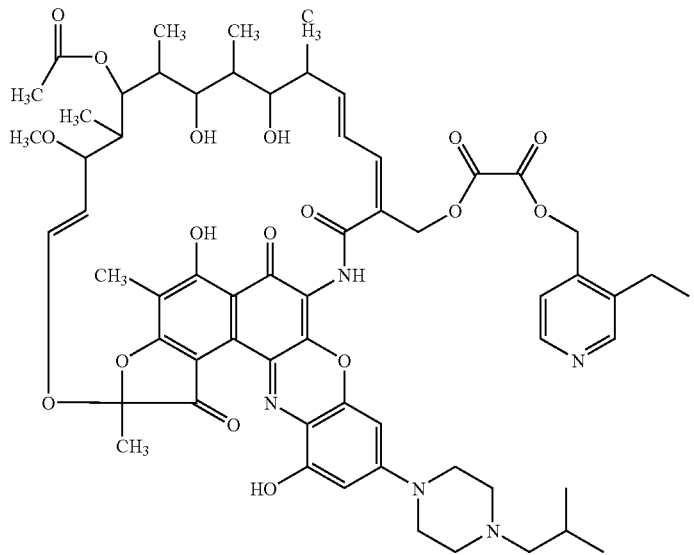

This approach may be adapted to any di-acid linker of formula XXIII. The methods described in Example 10 can be used to synthesize 2-ethyl-4-pyridinemethanol conjugates of formulas XXVIII–XXXV.

EXAMPLE 11

Synthesis of p-Aminosalicylic Acid Conjugates

4-Aminosalicylic acid (Aldrich, catalog number A7,960-4) can be protected as described in Example 1 to yield the following intermediates.

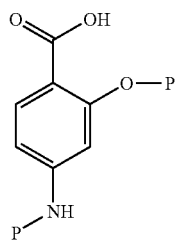

LIX

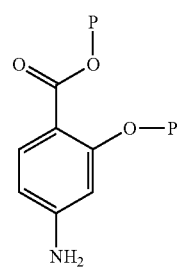

LX

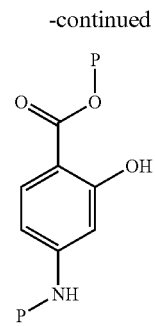

LXI

Conjugates of LXI can be prepared according to the method described in Example 9. The reaction produces compounds of formulas XXVIII–XXXV. For reactions involving compounds of formula XXa (see FIG. 3), the resulting products are shown below.

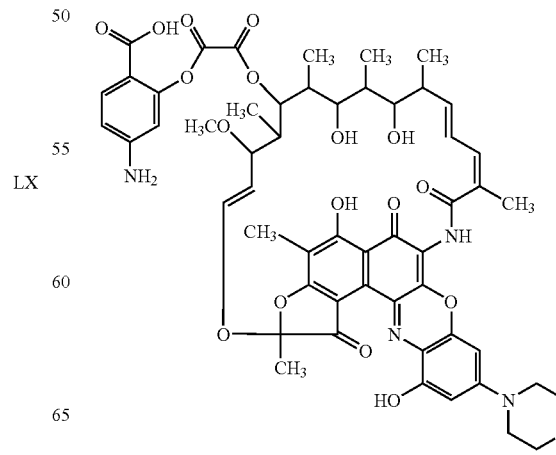

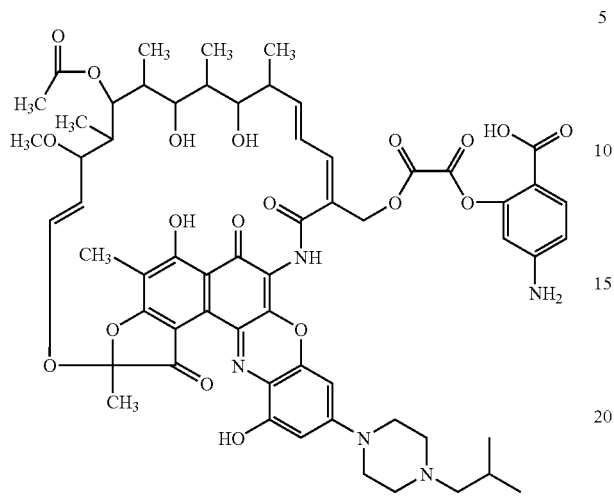
Conjugates of LX can be prepared according to the method described in Example 8. The reaction produces compounds of formulas XXVIII–XXXV. For reactions involving compounds of formula XXa (see FIG. 3), the resulting products are shown below.
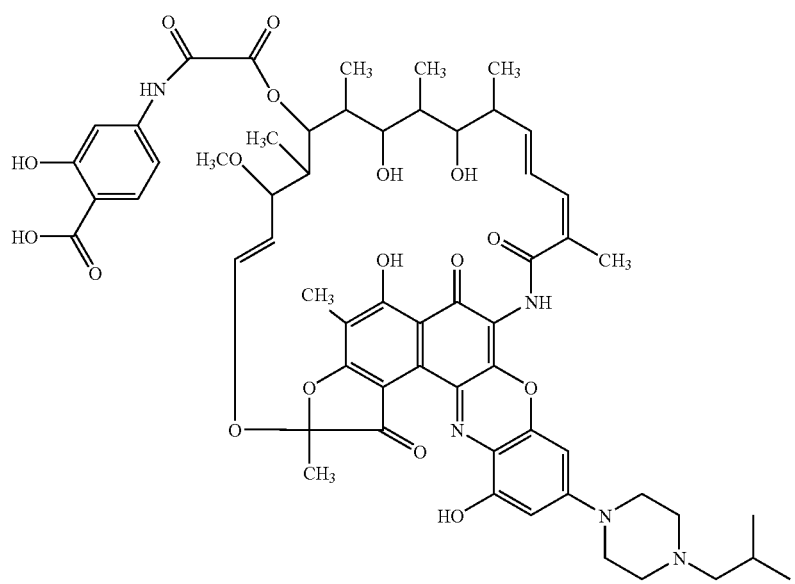

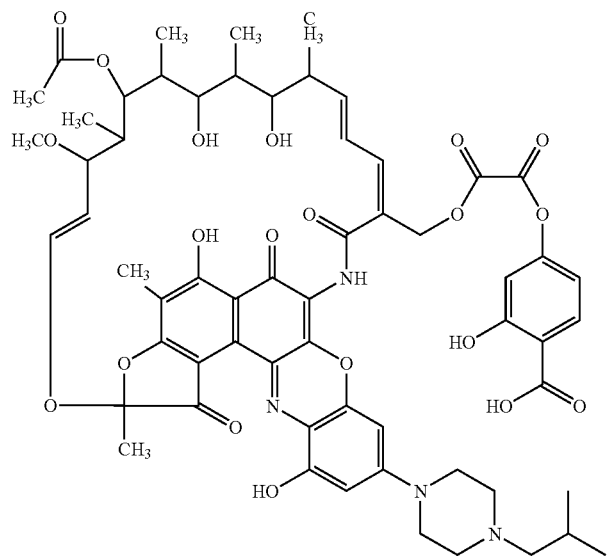
Conjugates of LIX can be prepared according to the method described in Example 8. The reaction produces compounds of formulas XXVIII–XXXV. For reactions involving compounds of formula XXa (see FIG. 3), the resulting products are shown below.
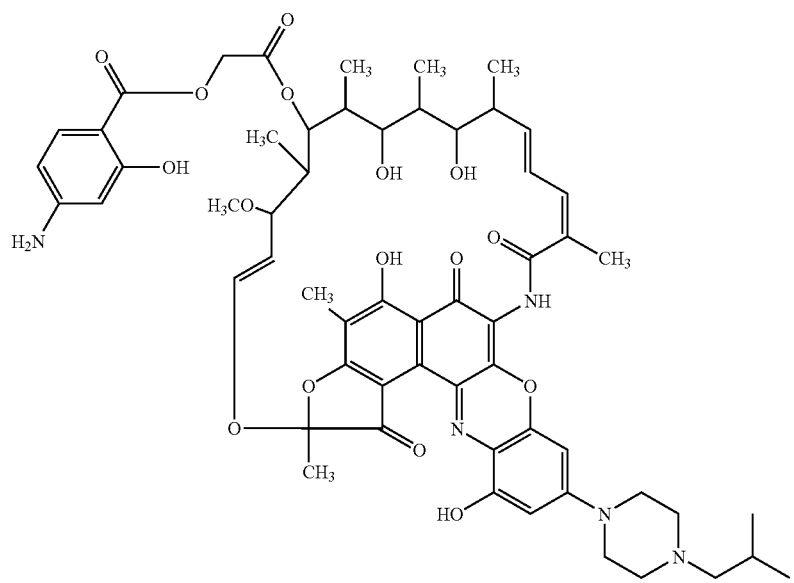

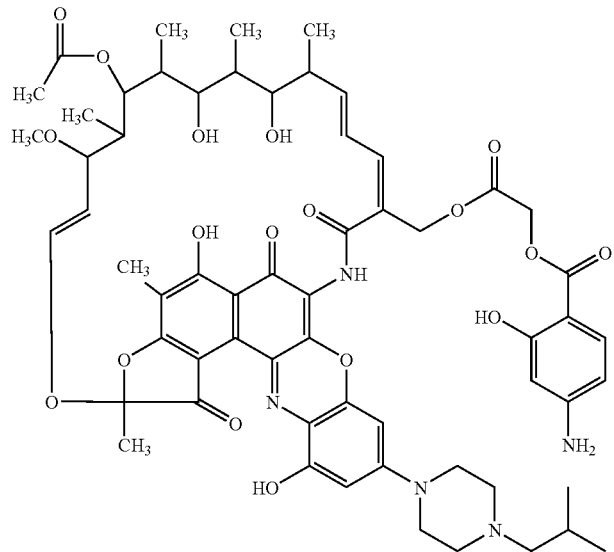

These approaches may be adapted to any di-acid or alcohol-acid linkers of formulas XXI or XXIII. The methods described in Example 11 can be used to synthesize aminosalicylic acid conjugates of formulas XXVIII–XXXV.

EXAMPLE 12

Synthesis of Isonicotinic Acid and 2-Ethyl-Isonicotinic Acid Conjugates

Isonicotinic acid (Aldrich, catalogue number I-1,750-8) and 2-ethyl-isonicotinic acid, an intermediate of reaction scheme 8, conjugates of formulas XXVIII–XXXV can be prepared using the method described in Example 6. For reactions involving compounds of formula XXa (see FIG. 3), the resulting products are shown below.

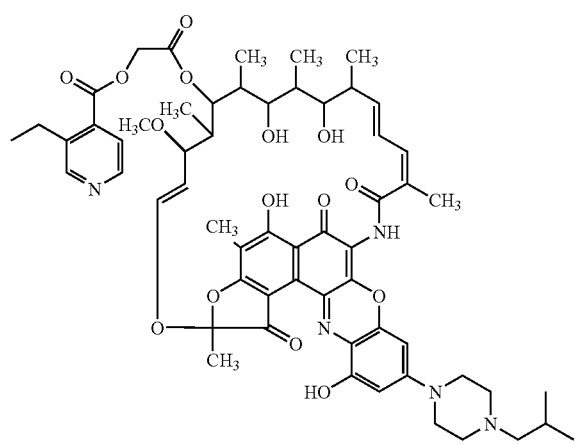

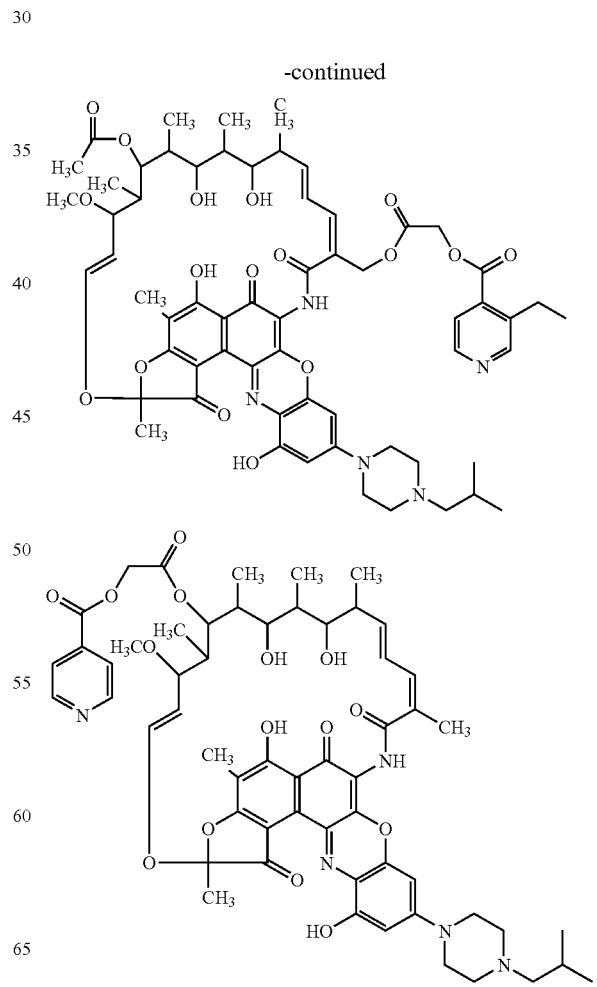

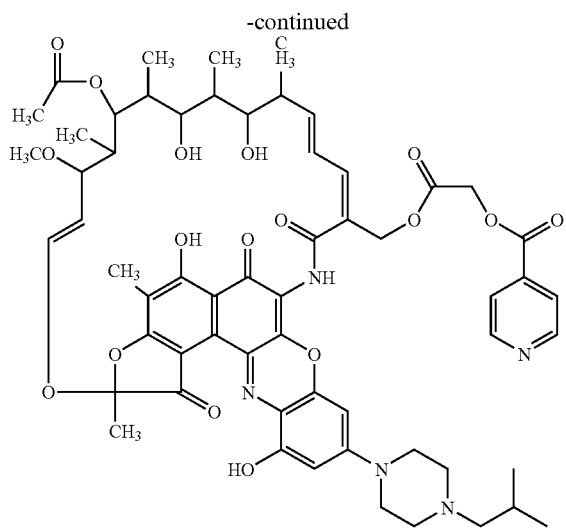

The methods described in Example 12 can be used to synthesize isonicotinic acid conjugates of formulas XXVIII–XXXV.

EXAMPLE 13

Synthesis of Azithromycin Conjugates

Azithromycin conjugates can be prepared using a slightly modified version of the method of Example 7. First, a protected rifamycin compound of formulas LIII–LVI can be linked to oxalic acid (e.g., reaction scheme 7), followed by deprotection of the oxalic acid protecting group. For reactions involving compounds of formula XXa (see FIG. 3), the products are shown below.

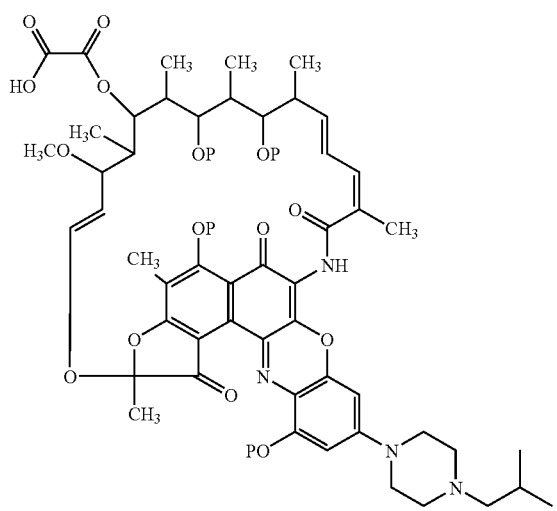

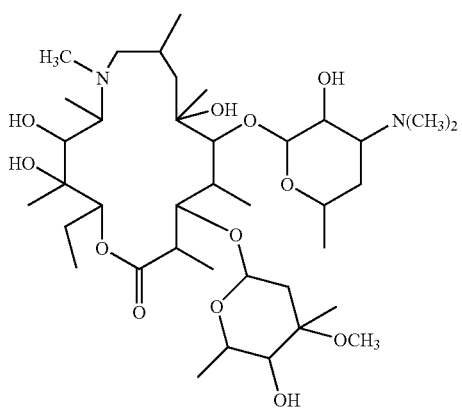

This intermediate contains an unprotected acid which is then activated and added to a solution containing a large excess of azithromycin (structure provided below). Each reaction can produce up to five products, one for each free hydroxyl of azithromycin. These five compounds have the formula of one of XLIII–XLVII. The compounds can be separated by affinity chromatography. Each isolated material can be identified using NMR techniques, and individually tested for antimicrobial activity.

This approach may be adapted to any di-acid linker of formulas XXIII. The methods described in Example 13 can be used to synthesize azithromycin conjugates of formulas XXVIII–XXXV.

EXAMPLE 14

Synthesis of Sulfhydryl Benzoxazinorifamycin Derivatives of Formula XX

Precursor Sufhydryl Amino Phenol

Rifamycin derivatives having the formula XX in which $R_2$ is sulfhydryl are prepared by reacting rifamycin S (LKT Laboratories, Inc., catalogue number DR32202) with a compound having the formula LXII.

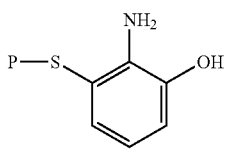

LXII

Compounds of formula LXII are prepared from 2-aminoresorcinol (Chem Service, Inc., catalogue number 1895B) as shown in reaction scheme 12, in which protecting groups, P, are selected from Example 1. The unprotected hydroxyl can be activated using standard techniques (e.g., conversion to a tosylate, brosylate, reaction scheme 12

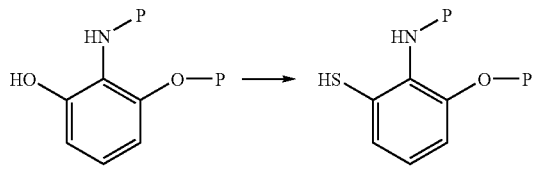

mesylate, triflate or other reactive leaving group see, for example, "J. March, Advanced Organic Chemistry: Reactions, Mechanisms and Structure" (1992, pp. 352–354, John Wiley & Sons, Inc.). The conversion of the activated alcohol to a sulfhydryl group can be achieved by either addition of sulfide (e.g., NaSH, $Na_2S$), addition of disulfide (e.g., $Na_2S_2$) followed by reduction of the disulfide to a sulfhydryl group, or transesterification of the activated alcohol with thioacetate followed by hydrolysis to the sulfhydryl with sodium acetate. The reaction product is converted into a compound of formula LXII using standard protection and deprotection chemistry (see Example 1).

Synthesis of Sulfhydryl Benzoxazinorifamycin

In a typical reaction, a compound of formula LXII is added in small portions to a solution of rifamycin S in chloroform containing several equivalents of triethylamine. This is followed by the addition of manganese dioxide and the reaction stirred until reaching completion. The resulting compound has the formula LXIII, shown below.

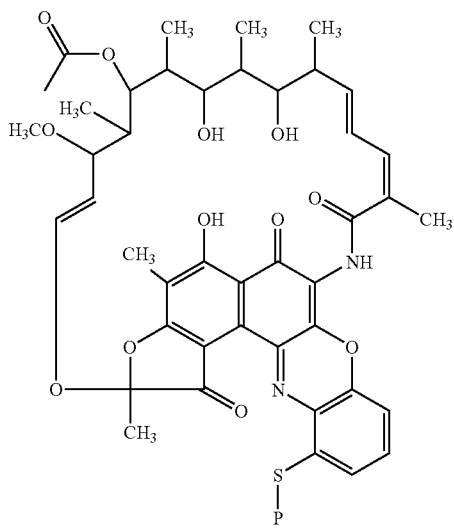

LXIII

Synthesis of Sulfhydryl Benzoxazinorifamycin Derivatives of Formula XX

The sulfhydryl benzoxazinorifamycin product is further modified, using the methods disclosed in U.S. Pat. No. 4,690,919. A compound represented by formula LXIII is dissolved in DMSO, mixed with N-isobutylpiperazine and manganese dioxide, and the reaction mixture stirred at room temperature for three hours. The resulting product is shown below. The

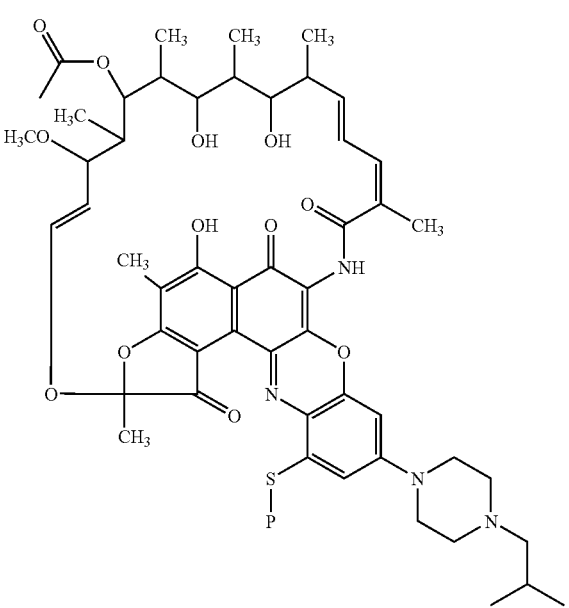

sulfhydryl protecting group can be removed, resulting in a compound of formula XX.

Compounds in which $R_3$ of formula XX is selected from other groups can be prepared by the method described above.

Synthesis of Compounds of Formula XX in which $X_1$ is Sulfur

Compounds for which $X_1$ of formula XX is a sulfur atom are prepared by the method described above, but using starting materials, LXIV or LXV, shown below.

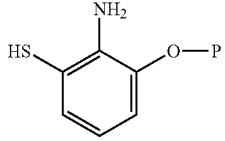

LXIV

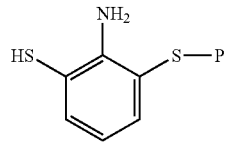

LXV

These materials can be prepared from 2-aminoresorcinol. For example, a compound of formula LXV can be prepared by converting both hydroxyls of 2-aminoresorcinol to sulfhydryls using the techniques described above, followed by the deprotection and/or protection of functional groups.

A compound of formula LXIV or LXV can be combined with rifamycin S, vide supra, to produce the sulfhydryl benzoxazinorifamycin intermediates shown below. To these intermediates can be added $R_3$, as defined in formula XX,

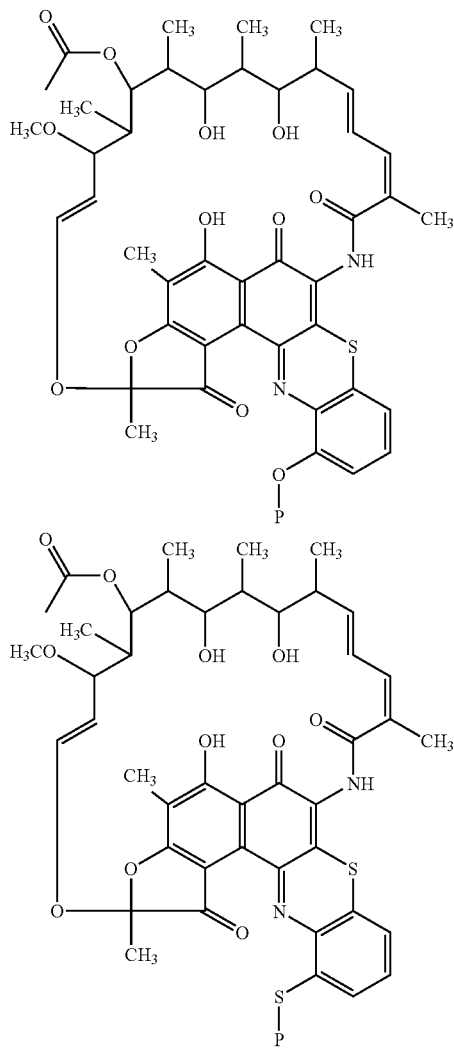

using the methods disclosed in U.S. Pat. No. 4,690,919 and described above.

EXAMPLE 15

Synthesis of Drug-Rifamycin Derivative Conjugates of Formula XXXV

Conjugates of formula XXXV can be prepared using the methods described in U.S. Pat. No. 4,585,589, hereby incorporated by reference. For example, the acid halide of pyrazinoic acid can be reacted with Rifalazil. Using the conditions described in U.S. Pat. No. 4,585,589, the phenolic hydroxyl group can be selectively acylated, as shown in reaction scheme 13, which includes protection and deprotection of the remaining hydroxyl groups in the compound.

reaction scheme 13

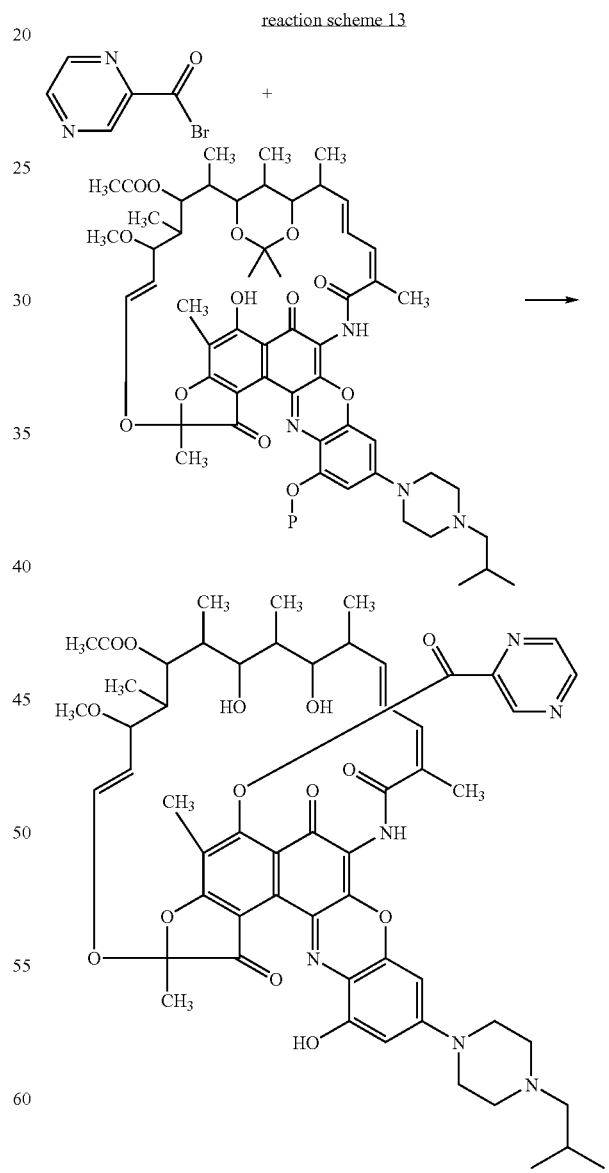

Any (A)—(L)—(B) conjugate of formula XXXV in which rifamycin derivative (A) is attached to linker (L) via an ester linkage group can be prepared in this manner.

EXAMPLE 16

Synthesis of ABI 0027

ABI 0027 is a zero-length linker conjugate of rifalazil and isonicotinic acid. Conjugation to rifalazil modifies the biodistribution of isonicotinic acid in a manner that can enhance its antimicrobial activity.

The preparation of ABI 0027 is shown below in reaction scheme 14. The details for the synthesis of each intermediate compound of reaction scheme 14 are also provided below.

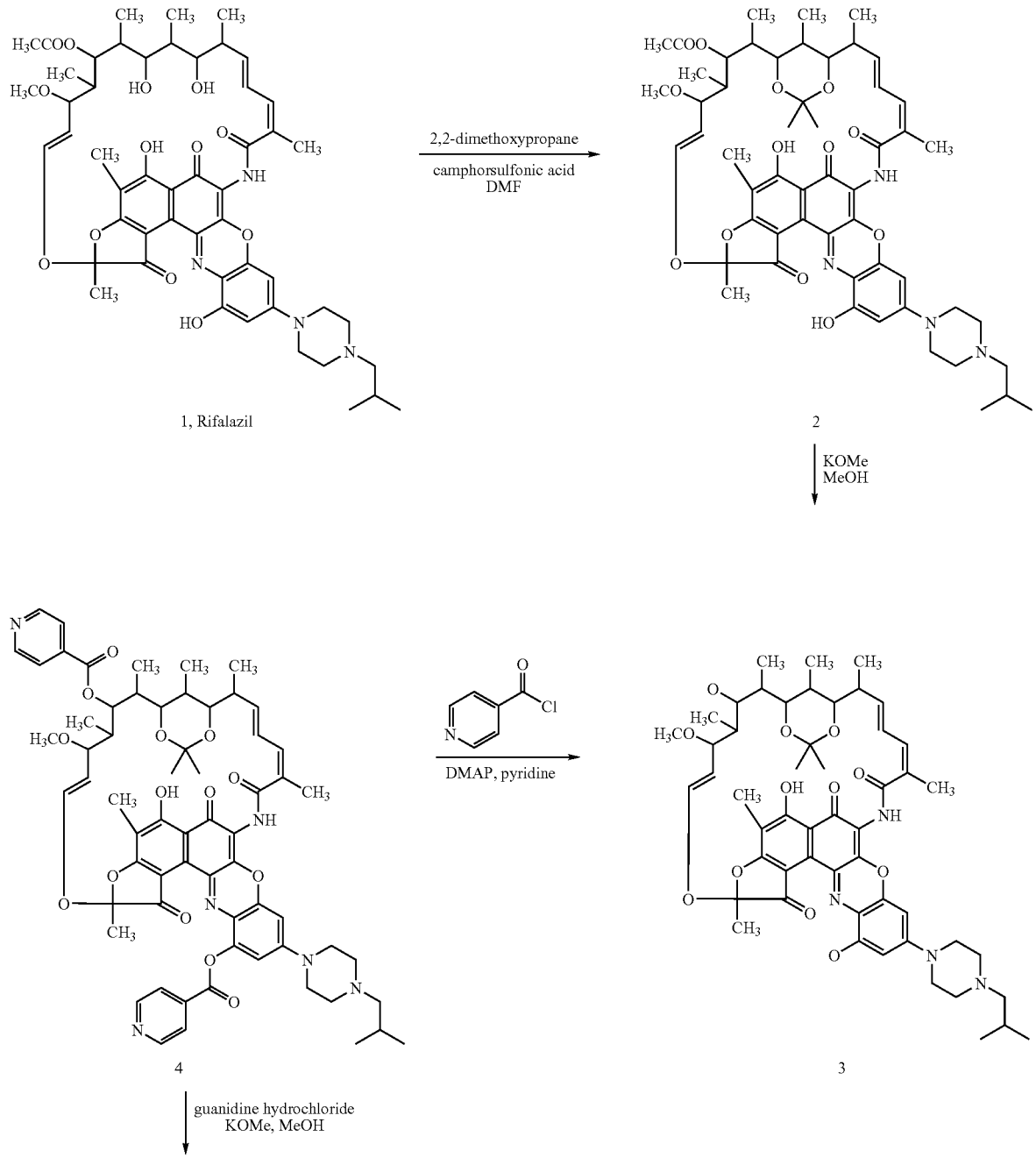

reaction scheme 14

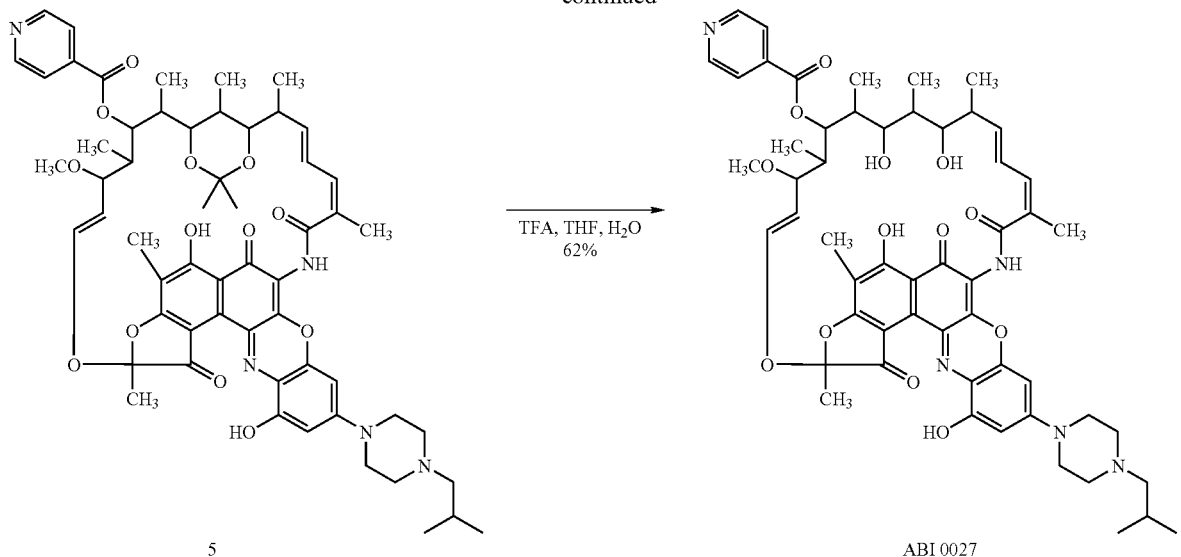

Preparation of Compound 2

To a solution of Rifalazil (9.5 g, 10 mmol) in DMF (100 mL) was added 2,2-dimethoxypropane (60 mL, 484 mmol) and camphorsulfonic acid (CSA, 0.20 g, 0.79 mmol) at room temperature under nitrogen. The resulting solution was heated at 85° C. for 14 hours. The reaction was cooled to about 50° C., and another portion of 2,2-dimethoxypropane (20 mL, 161 mmol) was added to the reaction. The solution was then heated at 85° C. for another 12 hours. The reaction was then cooled to room temperature and diluted with ethyl acetate (800 mL). For handling convenience, the solution was divided into two portions. Each portion was washed with $H_2O$ (2×500 mL) and the combined water layer was extracted once with ethyl acetate (200 mL). The combined organic layer was dried with sodium sulfate and concentrated under vacuum. The blue solid residue was purified by flash column chromatography (silica gel, 1:3 acetone:hexanes, $R_f$=0.50) to give 4.2 g (42%) of compound 2. ESI MS 981 (M+1).

Preparation of Compound 3

To a 500 mL flask charged with 200 mL of ether was added potassium methoxide (10 g, 127 mmol) at 0° C. under nitrogen. Methanol (5 mL) was added to this suspension and the mixture was stirred for 5 minutes at 0° C. Compound 2 (5.0 g, 5.01 mmol) was added to the mixture and the system was allowed to warm to room temperature, with stirring, overnight. The reaction was poured into a saturated ammonium chloride solution (100 mL). The resulting mixture was diluted with water (200 mL) and extracted with dichloromethane (2×500 mL). The combined organic layer was dried with sodium sulfate and the residue was purified by column chromatography (silica gel, 1:3 acetone:hexanes, $R_f$=0.40) to give 4.2 g (85%) of compound 3. ESI MS 940 (M+1).

Preparation of Compound 4

To a solution of compound 3 (723 mg, 0.769 mmol) in pyridine (10 mL) was added isonicotinoyl chloride hydrochloride (685 mg, 5.39 mmol) then dimethylaminopyridine (DMAP, 200 mg) at room temperature. The resulting mixture was stirred at 85° C. for 2 hours. The mixture was then cooled to room temperature and diluted with ethyl acetate (200 mL). The resulting solution was washed with $H_2O$ (2×200 mL), dried with sodium sulfate and concentrated to give 4 as a blue solid (700 mg, 79% based on 2 substitutions).

Preparation of Compound 5

To a solution of guanidine hydrochloride (137 mg, 1.43 mmol) in methanol (20 mL) was added potassium methoxide (100 mg, 1.43 mmol). The resulting mixture was stirred for 10 minutes at room temperature. To this mixture was added compound 4 (600 mg, 0.478 mmol based on 2 substitutions) and the resulting mixture was stirred for 1.5 h at room temperature. The reaction was then diluted with $H_2O$ (200 mL) and extracted with ethyl acetate (2×300 mL). The combined organic layer was dried with sodium sulfate and concentrated under vacuum. The residue was purified by flash column chromatography (silica gel, gradient of 1% to 2% methanol in dichloromethane) to give compound 5 as a blue solid. $R_f$=0.70 in 1:1 acetone:hexanes. ESI MS 1044 (M+1).

Preparation of Compound ABI 0027

A mixture of THF/$H_2O$/TFA (20:5:1 by volume) (10 mL) was added into a flask containing compound 5 (250 mg) at 0° C. The mixture was allowed to warm to room temperature and then stirred for 24 hours at room temperature. The mixture was then diluted with dichloromethane (100 mL), washed with $H_2O$ (2×200 mL) and dried with sodium sulfate. The solvent was removed under vacuum to give a crude product which was purified by flash column chromatography (silica gel, 2.5% methanol in dichloromethane) to yield 149 mg of ABI 0027 (62%). The pure compound is a blue solid with $R_f$=0.40 in 5:95 methanol:dichloromethane. ESI MS 1004 (M+1).

EXAMPLE 17

Synthesis of ABI 0029

ABI 0029 is a zero-length linker conjugate of rifalazil and isonicotinic acid. Conjugation to rifalazil modifies the biodistribution of isonicotinic acid in a manner that can enhance its antimicrobial activity.

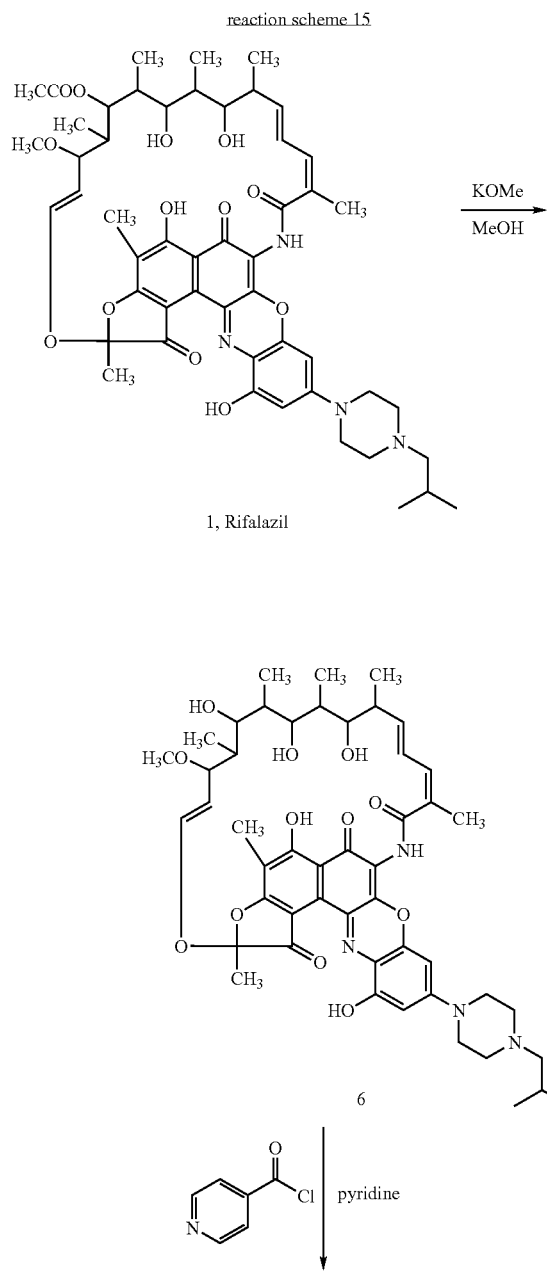

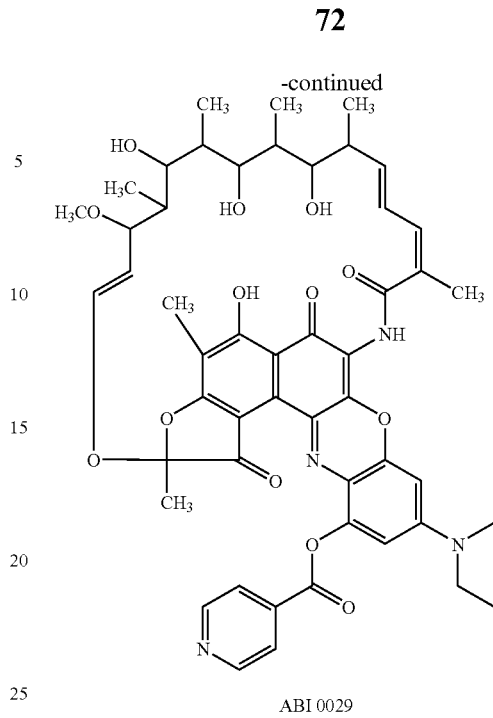

ABI 0029

The preparation of ABI 0029 is shown above in reaction scheme 15. Details for the synthesis of each intermediate compound of reaction scheme 15 are provided below.

Preparation of Compound 6

Potassium methoxide (447 mg, 6.39 mmol) was added to a solution of Rifalazil (2.0 g, 2.1 mmol) in methanol (20 mL) at room temperature and then stirred overnight. The reaction was then diluted with water (1000 mL) and extracted with dichloromethane (2×200 mL). The combined organic layer was dried with sodium sulfate and concentrated under vacuum. Purification by column chromatography (silica gel, 2.5% methanol in dichloromethane, $R_f$=0.40 in 5% methanol in dichloromethane) provided compound 6 as a blue solid (1.72 g, 90%). ESI MS 867 (M−MeOH+1).

Preparation of Compound ABI 0029

To a solution of compound 6 (853 mg, 0.949 mmol) in pyridine was added isonicotinoyl chloride (169 mg, 0.949 mmol) and DMAP (23 mg, 0.190 mmol) at room temperature. The resulting solution was stirred at room temperature for 2 hours then diluted with dichloromethane (200 mL), washed with water (2×200 mL) and dried with sodium sulfate. Column chromatography purification (silica gel, 2.5% methanol in dichloromethane, $R_f$=0.30 in 5% methanol in dichloromethane) gave ABI 0029 (120 mg, 12%) as a blue solid. ESI MS 1004 (M+1).

EXAMPLE 18

MIC Assay

MICs of candidate compounds of the invention can be determined, for example, by the method of Lee et al., *Am. Rev. Respir. Dis.* 136:349 1987. To a BACTEC 12B vial (4 mL of 7H12B medium), 0.1 mL of a 10-fold dilution of subculture of the test organisms in 7H9 medium (optical density at 540 nm, 0.1) can be inoculated and cultured at 37° C. until a growth index (GI) of 999 is reached. Then the broth culture can be removed and diluted 100-fold, and 0.1 mL of the dilution can be inoculated into a BACTEC 12B vial with or without a candidate compound. The candidate compound containing vials can hold 0.1 mL of candidate compound solution appropriately diluted to obtain the desired concentration. A 1% control vial, 0.1 mL of the 100-fold dilution of the inoculum described above, can be inoculated into 12B vial without candidate compound. The 12B vials can be incubated at 37° C., and GI readings recorded daily, using a BACTEC 460 TB instrument (Johnston Laboratories, Townsend, Md.), until the control vial reaches a GI greater than 30. When the final readings in the GI of the candidate containing vials are lower than those of the 1% control, the drug is considered to have inhibited more than 99% of the bacterial population, and this concentration is defined as the MIC.

Other Embodiments

All publications and patent applications, and patents mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

What we claim is:

1. A compound of formula I:

(A)—(L)—(B)    I wherein
(B) is a therapeutic drug;
(L) is a linker which forms linkage groups with rifamycin derivative (A) and therapeutic drug (B), wherein said linker (L) is described by any of formulas XXI–XXV:

—(Z$^1$)$_o$—(Y$^1$)$_u$—(Z$^2$)$_s$—(R$_{11}$)—(Z$^3$)$_t$—(Y$^2$)$_v$—(Z$^4$)$_p$—  ,    (XXI)

(XXII)

(XXIII)

(XXIV)

, and (XXV)

—(Y$^3$)—(Z$^5$)$_w$—(R$_{14}$)$\overset{X_4}{=}$(R$_{15}$), wherein
Z$^1$, Z$^2$, Z$^3$, and Z$^4$ are each, independently, selected from O, S, and NR$_{12}$;
Z$^5$ is selected from O, S, or NR$_{16}$;
R$_{12}$ is hydrogen or an alkyl group;
R$_{16}$ is hydrogen or an alkyl group;
R$_{15}$ is selected from hydrogen, alkyl, or heteroalkyl;
Y$^1$, Y$^2$, and Y$^3$ are each, independently, selected from carbonyl, thiocarbonyl, sulphonyl, and phosphoryl;
o, p, s, t, u, v, and w are each, independently, 0 or 1;
R$_{11}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —(CH$_2$CH$_2$O)$_q$CH$_2$CH$_2$— in which q is 1 to 4, or a chemical bond linking —(Z$^1$)$_o$—(Y$^1$)$_u$—(Z$^2$)$_s$— to —(Z$^3$)$_t$—(Y$^2$)$_v$—(Z$^4$)$_p$;
R$_{13}$ represents a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —(CH$_2$CH$_2$O)$_n$CH$_2$CH$_2$— in which n is 1 to 4, or a chemical bond linking two nitrogens or two carbonyls;
R$_{14}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —(CH$_2$CH$_2$O)$_n$CH$_2$CH$_2$— in which n is 1 to 4, or a chemical bond linking —(Y$^3$)—(Z$^5$)$_w$— to the hydrazone carbon; and
X$_4$ is a hydrazone resulting from the condensation reaction of a drug B containing a hydrazide group and the precursor to linker XXV in which X$_3$ is the oxygen atom of a ketone or aldehyde; and
(A) is a rifamycin derivative of formula II:

II wherein each methine proton, methylene proton, and methyl proton of formula II is optionally substituted by —OH or —OR*;
R represents a hydrogen atom, a hydroxyl group or —OR*;
R$_1$ represents a hydrogen atom, an acetyl group, or R*;

ring G is selected from formulas III–XI:

III

[Structure: phenoxazine/phenothiazine-type tricyclic with C=O at position 1, X₁ at position linking rings, R₂ and R₃ substituents]

IV

[Structure: cyclohexadienone with H₁ at position 4, C=O at position 1]

V

[Structure: benzene fused with pyrazole-type ring, C=O, NH, N–H₂]

VI

[Structure: benzimidazole with C=O, R₃ substituent on imidazole carbon]

VII

[Structure: fused tricyclic benzimidazole-pyridine type with C=O, R₂, R₃ substituents]

VIII

[Structure: 1,4-bis(OR') benzene]

IX

[Structure: benzene with OR' at positions 1 and 4, H₁ substituent at position 3]

X

[Structure: benzimidazole with OR' group, N–R₄, R₃ on imidazole C]

XI

[Structure: benzimidazole isomer with OR' group, N–R₄, R₃ on imidazole C]

R' represents a hydrogen atom or R*;
X₁ represents an oxygen atom or a sulfur atom;
H₁ represents an oxygen atom, N—R₃ or R*;
H₂ represents a group expressed by formulas XII or XIII:

XII

[Structure: carbon with two R₄ groups]

XIII

[Structure: cyclohexane with R₆, R₇, X₂ substituents and gem-dimethyl]

R₂ represents a hydroxyl group, a sulfhydryl group, a hydrogen atom, or an alkyl group having 1 to 3 carbon atoms;

R₃ represents a hydrogen atom, an alkyl group having 1 to 10 carbon atoms, or a group expressed by one of formulas XIV–XVI:

XIV

[Structure: –N(R₅)(R₅)]

XV

[Structure: –(CH₂)_g–CH with 1,3-dioxolane]

XVI

[Structure: piperazine-type ring with R₆, R₇, X₂]

each R₄ is, independently, a hydrogen atom or an alkyl group having 1 to 7 carbon atoms;
each R₅ is, independently, an alkyl group having 1 to 7 carbon atoms, or two of R₅ in combination form a 3–8 membered cyclic system;

g represents an integer between 1 and 3;

$R_6$ and $R_7$ are each, independently, a hydrogen atom or an alkyl group having 1 to 3 carbon atoms;

$X_2$ represents an oxygen atom, a sulfur atom, a carbonyl group, or a group expressed by one of formulas XVII–XIX:

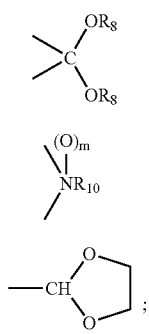

XVII

XVIII

XIX $R_8$ and $R_9$ are each, independently, a hydrogen atom, or an alkyl group having 1 to 3 carbon atoms, or $R_8$ and $R_9$, in combination with each other, represent —$(CH_2)_k$—;

k represents an integer between 1 and 4;

m represents 0 or 1;

$R_{10}$ represents a hydrogen atom, an alkyl group having 1 to 6 carbon atoms, or —$(CH_2)_n X_3$;

n represents an integer between 1 and 4;

$X_3$ represents an alkoxy group having 1 to 3 carbon atoms, a vinyl group, or an ethynyl group; and R* is a bond in a linkage group between (A) and (L).

2. The compound of claim 1, wherein (A) is a rifamycin derivative of formula XX:

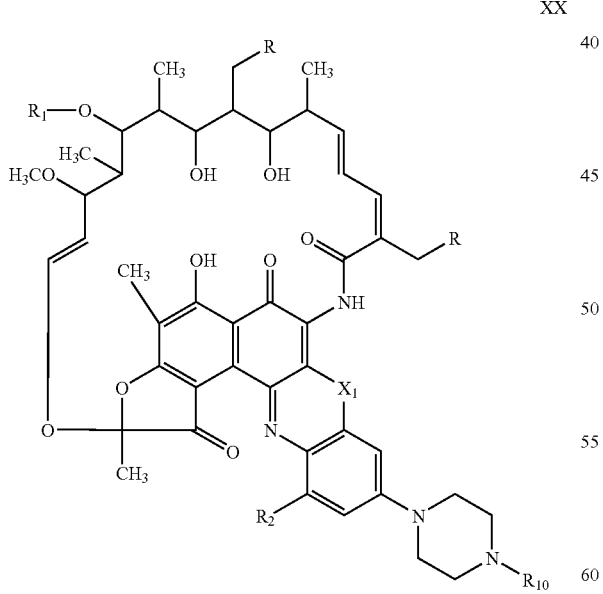

XX wherein

R represents a hydrogen atom, a hydroxyl group or —OR*;

$X_1$ represents an oxygen atom or a sulfur atom;

$R_1$ represents a hydrogen atom, an acetyl group, or R*;

$R_2$ represents a hydroxyl group, a sulfhydryl group, a hydrogen atom, or an alkyl group having 1 to 3 carbon atoms;

$R_{10}$ represents a hydrogen atom, an alkyl group having 1 to 6 carbon atoms, or —$(CH_2)_n X_3$;

n represents an integer between 1 and 4;

$X_3$ represents an alkoxy group having 1 to 3 carbon atoms, a vinyl group, or an ethynyl group; and R* is a bond in a linkage group formed with (L).

3. The compound of claim 2, wherein $X_1$ represents an oxygen atom;

$R_2$ represents a hydroxyl group or a sulfhydryl group; and $R_{10}$ is selected from the group consisting of methyl, ethyl, iso-propyl, n-propyl, iso-butyl, (S)-sec-butyl, and (R)-sec-butyl.

4. A compound of formulas LXVI:

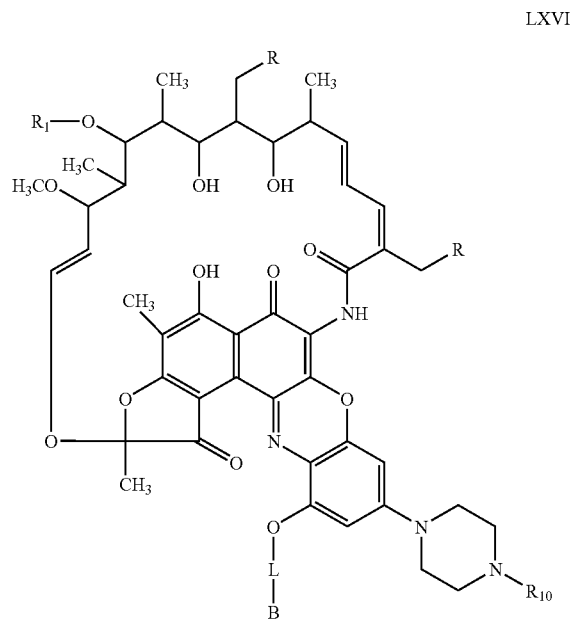

LXVI wherein R represents a hydrogen atom or a hydroxyl group;

$R_1$ represents a hydrogen atom or an acetyl group;

$R_{10}$ represents a hydrogen atom, an alkyl group having 1 to 6 carbon atoms, or —$(CH_2)_n X_3$ in which n represents an integer between 1 and 4 and $X_3$ represents an alkoxy group having 1 to 3 carbon atoms, a vinyl group, or an ethynyl group;

(B) is a therapeutic drug; and (L) is a linker described by any of formulas XXI–XXV:

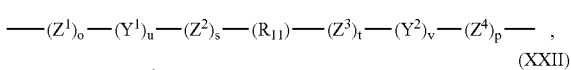

(XXI)

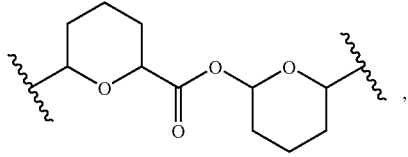

(XXII)

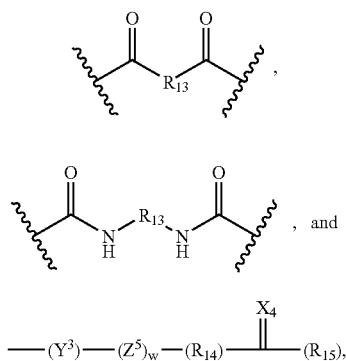

(XXIII)

(XXIV)

(XXV)

wherein $Z^1$, $Z^2$, $Z^3$, and $Z^4$ are each, independently, selected from O, S, and $NR_{12}$;

$Z^5$ is selected from O, S, or $NR_{16}$;

$R_{12}$ is hydrogen or an alkyl group;

$R_{16}$ is hydrogen or an alkyl group;

$R_{15}$ is selected from hydrogen, alkyl, or heteroalkyl;

$Y^1$, $Y^2$, and $Y^3$ are each, independently, selected from carbonyl, thiocarbonyl, sulphonyl, and phosphoryl;

o, p, s, t, u, v, and w are each, independently, 0 or 1;

$R_{11}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, $-(CH_2CH_2O)_qCH_2CH_2-$ in which q is 1 to 4, or a chemical bond linking $-(Z^1)_o-(Y^1)_u-(Z^2)_s-$ to $-(Z^3)_t-(Y^2)_v-(Z^4)_p$;

$R_{13}$ represents a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, $-(CH_2CH_2O)_nCH_2CH_2-$ in which n is 1 to 4, or a chemical bond linking two nitrogens or two carbonyls;

$R_{14}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, $-(CH_2CH_2O)_nCH_2CH_2-$ in which n is 1 to 4, or a chemical bond linking $-(Y^3)-(Z^5)_w-$ to the hydrazone carbon; and $X_4$ is a hydrazone resulting from the condensation reaction of a drug B containing a hydrazide group and the precursor to linker XXV in which $X_3$ is the oxygen atom of a ketone or aldehyde.

5. The compound of claims 1 or 4 wherein linker (L) is cleavable.

6. The compound of claim 5, wherein, upon cleavage of linker (L), the biological activity of (B) is substantially identical to biological activity of (B) when not linked to (A).

7. The compound of claims 1 or 4, wherein said linker (L) is described by formula XXI:

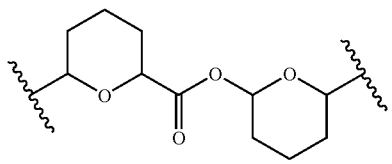

wherein $Z^1$, $Z^2$, $Z^3$, and $Z^4$ are each, independently, selected from O, S, and $NR_{12}$;

$R_{12}$ is hydrogen or an alkyl group;

$Y^1$ and $Y^2$ are each, independently, selected from carbonyl, thiocarbonyl, sulphonyl, and phosphoryl;

o, p, s, t, u, and v are each independently 0 or 1; and $R_{11}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, $-(CH_2CH_2O)_qCH_2CH_2-$ in which q is 1 to 4, or a chemical bond linking $-(Z^1)_o-(Y^1)_u-(Z^2)_s-$ to $-(Z^3)_t-(Y^2)_v-(Z^4)_p-$.

8. The compound of claims 1 or 4, wherein said linker (L) is described by one of formulas XXII–XXIV:

XXII

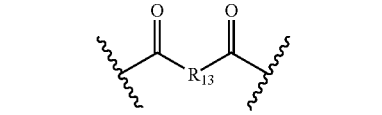

XXIII

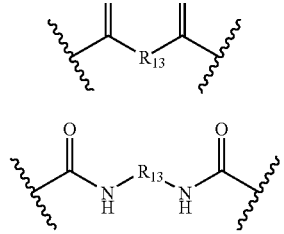

XXIV wherein $R_{13}$ represents a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, $-(CH_2CH_2O)_nCH_2CH_2-$ in which n is 1 to 4, or a chemical bond linking two nitrogens or two carbonyls.

9. The compound of claims 1 or 4, wherein said linker (L) is described by formula XXV:

XXV

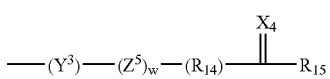

wherein $Z^5$ is selected from O, S, or $NR_{16}$;

$R_{16}$ is hydrogen or an alkyl group;

$R_{15}$ is selected from hydrogen, alkyl, or heteroalkyl;

Y³ is selected from carbonyl, thiocarbonyl, sulphonyl, and phosphoryl covalently bound to an oxygen atom of rifamycin derivative (A);

w is 0 or 1;

$R_{14}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_nCH_2CH_2$— in which n is 1 to 4, or a chemical bond linking —$(Y^3)$—$(Z^5)_w$— to the hydrazone carbon; and $X_4$ is a hydrazone resulting from the condensation reaction of a drug B containing a hydrazide group and the precursor to linker XXV in which $X_3$ is the oxygen atom of a ketone or aldehyde.

10. The compound of claims 1 or 4, wherein (B) is a radical derived from the group consisting of isoniazid, ethambutol, azithromycin, pyrazinamide, p-aminosalicylic acid, ethionamide, cycloserine, 4-pyridinemethanol, 2-ethyl-4-pyridinemethanol, isonicotinic acid, and 2-ethylisonicotinic acid.

11. A compound having the chemical structure of any one of formulas XXVI–XXXIV:

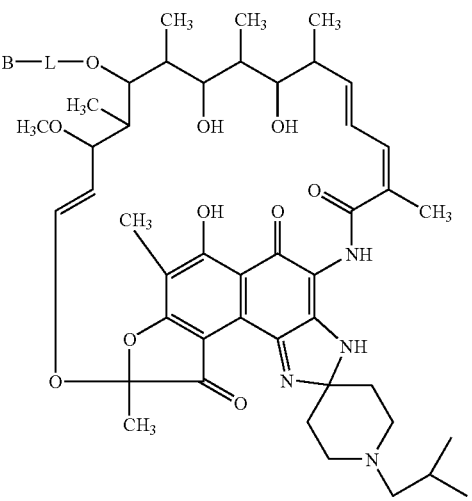

XXVIII

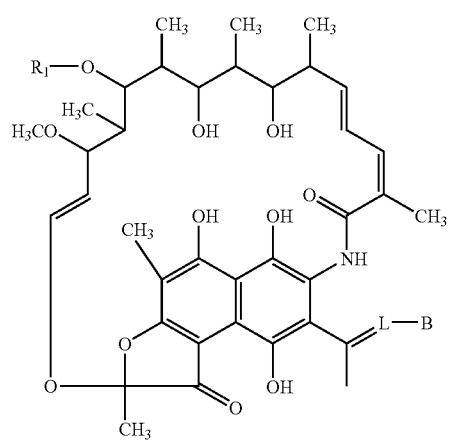

XXVI

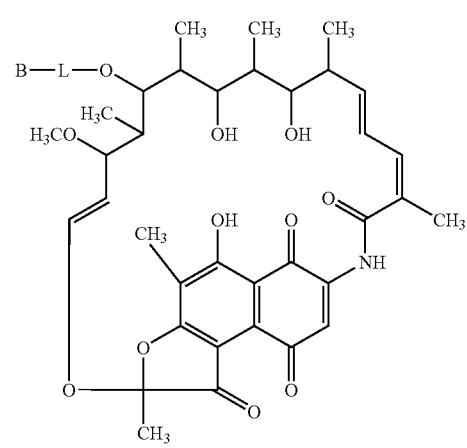

XXIX

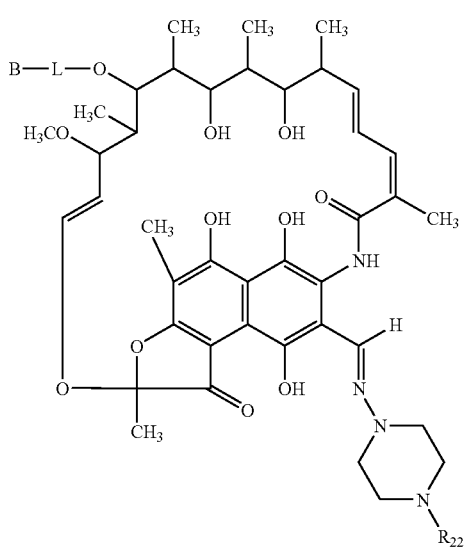

XXVII

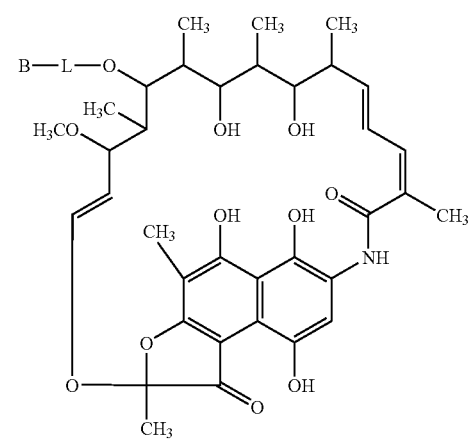

XXX

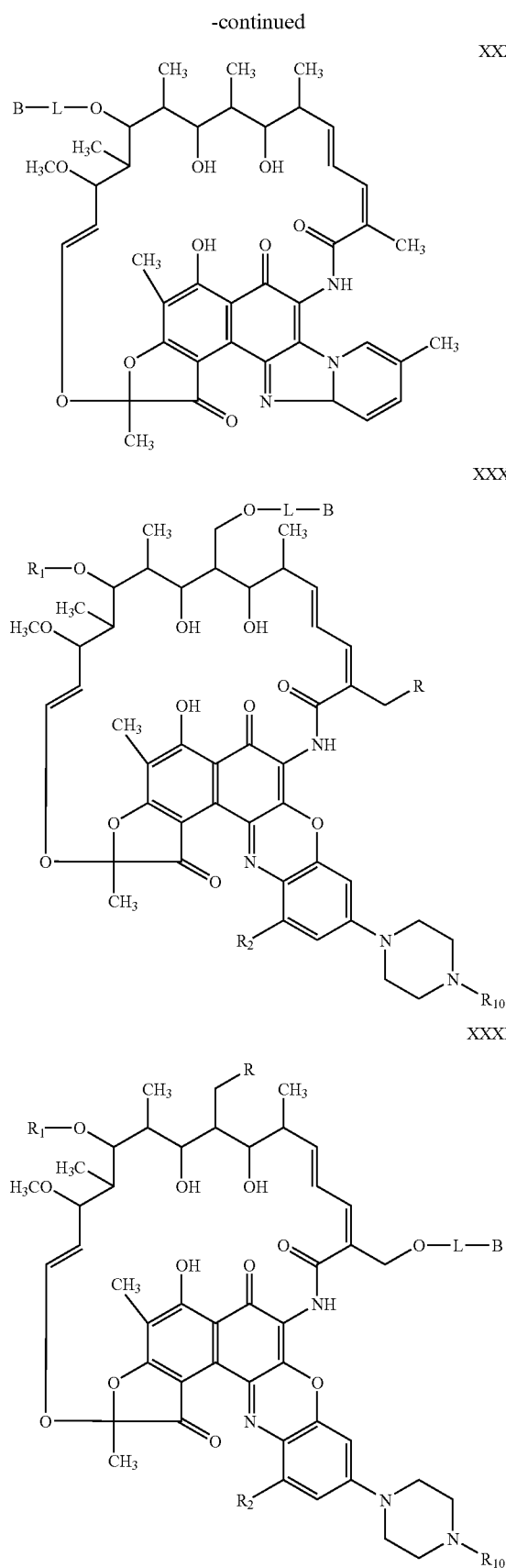
wherein L is a linker described by formulas XXI, XXII, XXIII, XXIV, or XXV:
$$—(Z^1)_o—(Y^1)_u—(Z^2)_s—(R_{11})—(Z^3)_t—(Y^2)_v—(Z^4)_p—\quad, \tag{XXI}$$
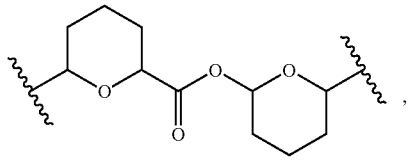
(XXII)

-continued

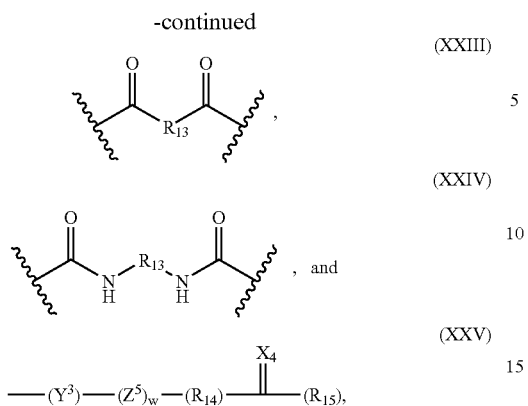
(XXIII)

(XXIV)

(XXV)

—(Y³)ₒ—(Z⁵)_w—(R₁₄)=(R₁₅), wherein
$Z^1$, $Z^2$, $Z^3$, and $Z^4$ are each, independently, selected from O, S, and $NR_{12}$;
$Z^5$ is selected from O, S, or $NR_{16}$;
$R_{12}$ is hydrogen or an alkyl group;
$R_{16}$ is hydrogen or an alkyl group;
$R_{15}$ is selected from hydrogen, alkyl, or heteroalkyl;
$Y^1$, $Y^2$, and $Y^3$ are each, independently, selected from carbonyl, thiocarbonyl, sulphonyl, and phosphoryl;
o, p, s, t, u, v, and w are each, independently, 0 or 1;
$R_{11}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_qCH_2CH_2$— in which q is 1 to 4, or a chemical bond linking —$(Z^1)_o$—$(Y^1)_u$—$(Z^2)_s$— to —$(Z^3)_t$—$(Y^2)_v$—$(Z^4)_p$;
$R_{13}$ represents a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_nCH_2CH_2$— in which n is 1 to 4, or a chemical bond linking two nitrogens or two carbonyls;
$R_{14}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_nCH_2CH_2$— in which n is 1 to 4, or a chemical bond linking —$(Y^3)$—$(Z^5)_w$— to the hydrazone carbon; and
$X_4$ is a hydrazone resulting from the condensation reaction of a drug B containing a hydrazide group and the precursor to linker XXV in which $X_3$ is the oxygen atom of a ketone or aldehyde;
B is selected from one of formulas XXXVI–XLII:

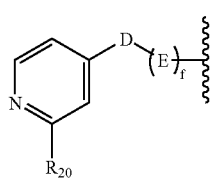
XXXVI

XXXVII

XXXVIII

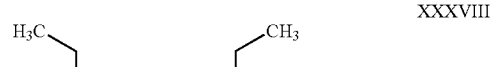
XXXIX

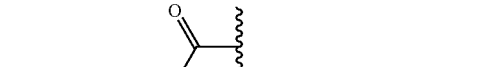
XL

XLI

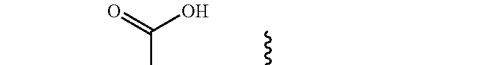
XLII

XLIII

-continued

XLIV

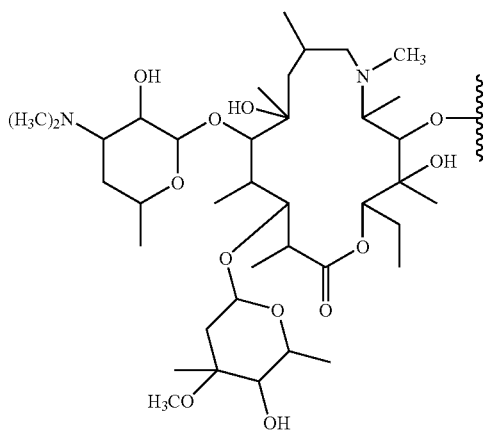

XLV

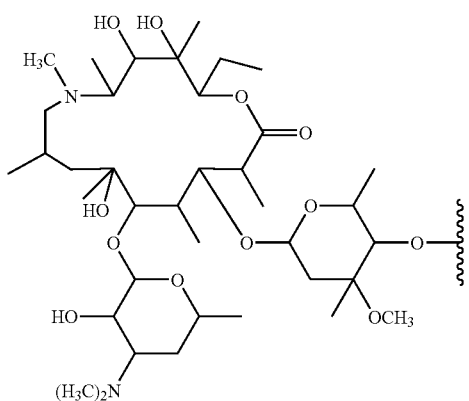

XLVI

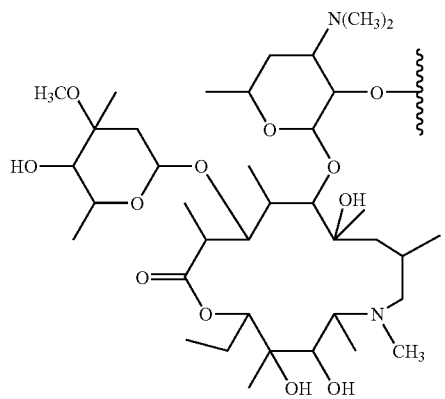

XLVII

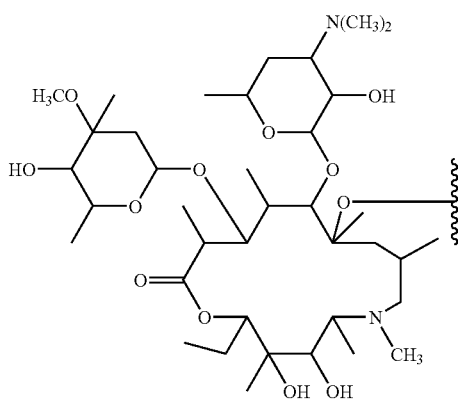

$R_1$ is H, or —C(O)CH$_3$;
$R_2$ represents a hydroxyl group or a sulfhydryl group;
$R_{10}$ is selected from the group consisting of methyl, ethyl, iso-propyl, n-propyl, iso-butyl, (S)-sec-butyl, and (R)-sec-butyl;
D is a carbonyl, thiocarbonyl, or methylene;
E is —NR$_{21}$, —O—, —S—, —NH—NH—, or —NH—N=;
f is 0 or 1;
$R_{20}$ is H or ethyl;
$R_{21}$ is H or alkyl; and
$R_{22}$ is methyl or cyclo-pentyl.

12. A method of increasing delivery of a therapeutic drug to a diseased cell, said method comprising linking said therapeutic drug to a rifamcyin derivative of formula II:

II

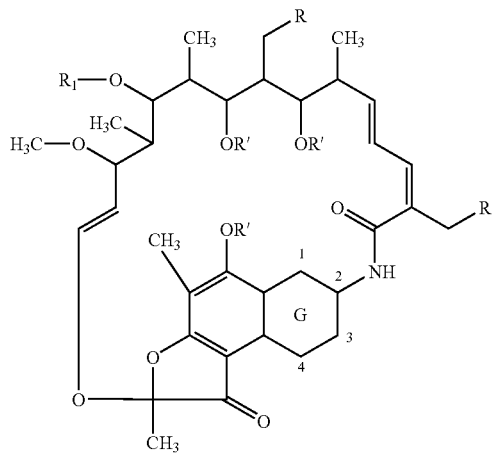

wherein each methine proton, methylene proton, and methyl proton of formula II is optionally substituted by —OH or —OR*;
R represents a hydrogen atom, a hydroxyl group or —OR*;
$R_1$ represents a hydrogen atom, an acetyl group, or R*;
ring G is selected from formulas III–XI:

III

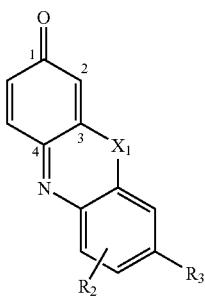

IV

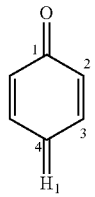

-continued

V
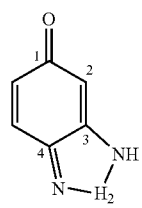

VI
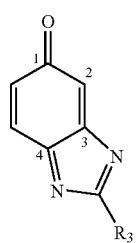

VII
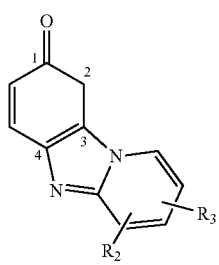

VIII
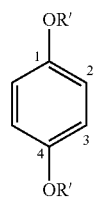

IX
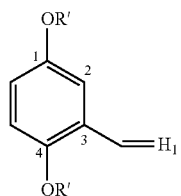

X
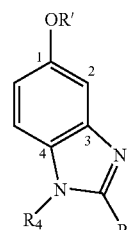

XI
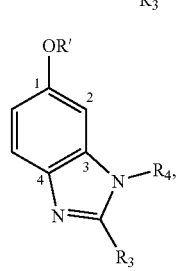

R' represents a hydrogen atom or R*;
$X_1$ represents an oxygen atom or a sulfur atom;
$H_1$ represents an oxygen atom, N—$R_3$ or R*;
$H_2$ represents a group expressed by formulas XII or XIII:

XII
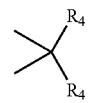

XIII
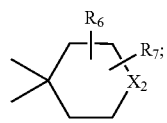

$R_2$ represents a hydroxyl group, a sulfhydryl group, a hydrogen atom, or an alkyl group having 1 to 3 carbon atoms;

$R_3$ represents a hydrogen atom, an alkyl group having 1 to 10 carbon atoms, or a group expressed by one of formulas XIV–XVI:

XIV
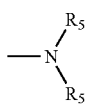

XV
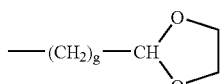

XVI
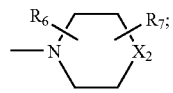

each $R_1$ is, independently, a hydrogen atom or an alkyl group having 1 to 7 carbon atoms;

each $R_5$ is, independently, an alkyl group having 1 to 7 carbon atoms, or two of $R_5$ in combination form a 3–8 membered cyclic system;

g represents an integer between 1 and 3;

$R_6$ and $R_7$ are each, independently, a hydrogen atom or an alkyl group having 1 to 3 carbon atoms;

$X_2$ represents an oxygen atom, a sulfur atom, a carbonyl group, or a group expressed by one of formulas XVII–XIX:

XVII
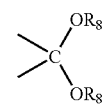

XVIII

XIX
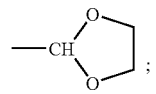

$R_8$ and $R_9$ are each, independently, a hydrogen atom, or an alkyl group having 1 to 3 carbon atoms, or $R_8$ and $R_9$, in combination with each other, represent —$(CH_2)_k$—;

k represents an integer between 1 and 4;

m represents 0 or 1;

$R_{10}$ represents a hydrogen atom, an alkyl group having 1 to 6 carbon atoms, or —$(CH_2)_n X_3$;

n represents an integer between 1 and 4;

$X_3$ represents an alkoxy group having 1 to 3 carbon atoms, a vinyl group, or an ethynyl group; and R* is a bond in a linkage group between said rifamycin derivative and a linker attached to said therapeutic drug, wherein said linker is degradable in vivo and is described by any of formulas XXI–XXV:

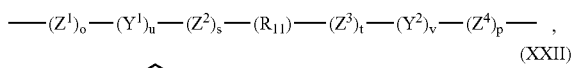
(XXI)

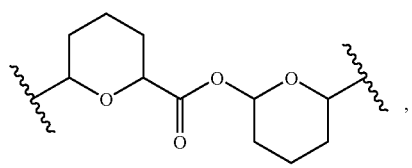
(XXII)

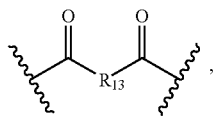
(XXIII)

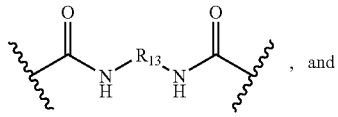
(XXIV)

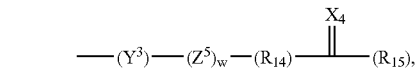
(XXV)

wherein $Z^1$, $Z^2$, $Z^3$, and $Z^4$ are each, independently, selected from O, S, and $NR_{12}$;

$Z^5$ is selected from O, S, or $NR_{16}$;

$R_{12}$ is hydrogen or an alkyl group;

$R_{16}$ is hydrogen or an alkyl group;

$R_{15}$ is selected from hydrogen, alkyl, or heteroalkyl;

$Y^1$, $Y^2$, and $Y^3$ are each, independently, selected from carbonyl, thiocarbonyl, sulphonyl, and phosphoryl;

o, p, s, t, u, v, and w are each, independently, 0 or 1;

$R_{11}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_q CH_2CH_2$— in which q is 1 to 4, or a chemical bond linking —$(Z^1)_o$—$(Y^1)_u$—$(Z^2)_s$— to —$(Z^3)_t$—$(Y^2)_v$—$(Z^4)_p$;

$R_{13}$ represents a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_n CH_2CH_2$— in which n is 1 to 4, or a chemical bond linking two nitrogens or two carbonyls;

$R_{14}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_n CH_2CH_2$— in which n is 1 to 4, or a chemical bond linking —$(Y^3)$—$(Z^5)_w$— to the hydrazone carbon; and $X_4$ is a hydrazone resulting from the condensation reaction of a drug B containing a hydrazide group and the precursor to linker XXV in which $X_3$ is the oxygen atom of a ketone or aldehyde.

13. The method of claim 12, wherein said drug is selected from the group consisting of isoniazid, ethambutol, azithromycin, pyrazinamide, p-aminosalicylic acid, ethionamide, cycloserine, 4-pyridinemethanol, 2-ethyl-4-pyridinemethanol, isonicotinic acid, and 2-ethyl-isonicotinic acid.

14. A pharmaceutical composition comprising an effective amount of a compound of claim 1, 4, or 11 or a suitable salt thereof, together with a pharmaceutically acceptable carrier or diluent.

15. A method of treating a bacterial infection in a mammal, said method comprising the step of administering to said mammal a pharmaceutical composition of claim 14 in an amount sufficient to treat said bacterial infection.

16. The method of claim 15, wherein said bacterial infection is caused by an obligate intracellular bacterium.

17. The method of claim 16, wherein said obligate intracellular bacterium is selected from the group consisting of *Anaplasma bovis, A. caudatum, A. centrale, A. marginale A. ovis, A. phagocytophila, A. platys, Bartonella bacilliformis, B. clarridgeiae, B. elizabethae, B. henselae, B. henselae phage, B. quintana, B. taylorii, B. vinsonii, Borrelia afzelii, B. andersonii, B. anserina, B. bissettii, B. burgdorferi, B. crocidurae, B. garinii, B. hermsii, B. japonica, B. miyamotoi, B. parkeri, B. recurrentis, B. turdi, B. turicatae, B. valaisiana, Brucella abortus, B. melitensis, Chlamydia pneumoniae, C. psittaci, C. trachomatis, Cowdria ruminantium, Coxiella burnetii, Ehrlichia canis, E. chaffeensis, E. equi, E. ewingii, E. muris, E. phagocytophila, E. platys, E. risticii, E. ruminantium, E. sennetsu, Haemobartonella canis, H. felis, H. muris, Mycoplasma arthriditis, M. buccale, M. faucium, M. fermentans, M. genitalium, M. hominis, M. laidawii, M. lipophilum, M. orale, M. penetrans, M. pirum, M. pneumoniae, M. salivarium, M. spermatophilum, Rickettsia australis, R. conorii, R. felis, R. helvetica, R. japonica, R. massiliae, R. montanensis, R. peacockii, R. prowazekii, R. rhipicephali, R. rickettsii, R. sibirica,* and *R. typhi.*

18. The method of claim 15, wherein said mammal is a human.

19. The compound of claim 7, wherein $R_{11}$ is a chemical bond linking —$(Z^1)_o$—$(Y^1)_u$—$(Z^2)_s$— to —$(Z^3)_t$—$(Y^2)_v$—$(Z^4)_p$—.

* * * * *

UNITED STATES PATENT AND TRADEMARK OFFICE
CERTIFICATE OF CORRECTION

| | | |
|---|---|---|
| PATENT NO. | : 7,122,525 B2 | Page 1 of 1 |
| APPLICATION NO. | : 10/302409 | |
| DATED | : October 17, 2006 | |
| INVENTOR(S) | : Michaelis et al. | |

It is certified that error appears in the above-identified patent and that said Letters Patent is hereby corrected as shown below:

Column 28, Line 64, replace "carboduimides" with --carbodiimides--.

Column 33, Line 26, replace "acid phosphoric" with --acid, phosphoric--.

Column 35, Line 9, replace "lewis acid" with --Lewis acid--.

Column 48, Line 53, replace "duimidazole" with --diimidazole--.

Column 62, Line 65, replace "formulas" with --formula--.

Column 63, Line 46, replace "leaving group see," with --leaving group) see,--.

Columm 67,
    Line 5, replace "rifalazil" with --Rifalazil--;
    Line 6, replace "rifalazil" with --Rifalazil--.

Column 71,
    Line 12, replace "rifalazil" with --Rifalazil--;
    Line 13, replace "rifalazil" with --Rifalazil--.

Signed and Sealed this

First Day of May, 2007

JON W. DUDAS
*Director of the United States Patent and Trademark Office*